US010605734B2

(12) United States Patent
Lafferty et al.

(10) Patent No.: US 10,605,734 B2
(45) Date of Patent: Mar. 31, 2020

(54) SYSTEMS AND METHODS FOR GENETIC SEQUENCING

(71) Applicant: LIFE TECHNOLOGIES CORPORATION, Carlsbad, CA (US)

(72) Inventors: William M. Lafferty, Encinitas, CA (US); Jonathan M. Rothberg, Guilford, CT (US); Keith G. Fife, Palo Alto, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 14/779,532

(22) PCT Filed: Apr. 2, 2014

(86) PCT No.: PCT/US2014/032604
§ 371 (c)(1),
(2) Date: Sep. 23, 2015

(87) PCT Pub. No.: WO2014/165554
PCT Pub. Date: Oct. 9, 2014

(65) Prior Publication Data
US 2016/0047747 A1    Feb. 18, 2016

Related U.S. Application Data

(60) Provisional application No. 61/835,428, filed on Jun. 14, 2013, provisional application No. 61/808,105, filed on Apr. 3, 2013.

(51) Int. Cl.
*G01N 21/64* (2006.01)
*C12Q 1/6874* (2018.01)

(52) U.S. Cl.
CPC ......... *G01N 21/648* (2013.01); *C12Q 1/6874* (2013.01); *G01N 21/6454* (2013.01); *G01N 2021/6441* (2013.01)

(58) Field of Classification Search
CPC ............ C12Q 1/6874; C12Q 2563/107; C12Q 2563/155; C12Q 2565/101;
(Continued)

(56) References Cited

U.S. PATENT DOCUMENTS 5,965,875 A * 10/1999 Merrill .............. H01L 27/14623
250/208.1
2007/0034777 A1 * 2/2007 Tuckerman ....... H01L 27/14618
250/208.1
(Continued)

FOREIGN PATENT DOCUMENTS

WO    2006/135782    12/2006
WO    2007/137060    11/2007
(Continued)

OTHER PUBLICATIONS

International Preliminary Report on Patentability for International Application No. PCT/US2014/032604 dated Oct. 6, 2015, 6 pages.
(Continued)

*Primary Examiner* — Sally A Merkling

(57) ABSTRACT

A device including a transparent layer defining a surface exposed to a flow volume and to secure a target polynucleotide template and a detector structure secured to the transparent layer and including a plurality of detectors to detect a signal emitted during nucleotide incorporation along the target polynucleotide template.

20 Claims, 20 Drawing Sheets

Specification includes a Sequence Listing.

(58) Field of Classification Search
CPC ........ C12Q 2565/607; C12Q 2565/629; C12Q 2565/632; G01N 2021/6441; G01N 21/6454; G01N 21/648; H01L 27/14621; H01L 27/14625; G02B 27/144; G02B 6/10; G02B 6/12004
See application file for complete search history.

(56) References Cited

U.S. PATENT DOCUMENTS

2009/0250615 A1    10/2009    Oldham et al.
2009/0305287 A1*  12/2009    Nordman ............. C12Q 1/6869
                                                           435/6.12

FOREIGN PATENT DOCUMENTS

| WO | 2008/076406 | 6/2008 |
| WO | 2009/056065 | 5/2009 |
| WO | 2009/091847 | 7/2009 |
| WO | 2010/002939 | 1/2010 |
| WO | 2010/111674 | 9/2010 |
| WO | 2010/141390 | 12/2010 |
| WO | 2011/090745 | 7/2011 |
| WO | 2011/091043 | 7/2011 |
| WO | 2012/031234 | 3/2012 |

OTHER PUBLICATIONS

International Search Report and Written Opinion for International Application No. PCT/US2014/032604 dated Jul. 11, 2014, 11 pages.

* cited by examiner

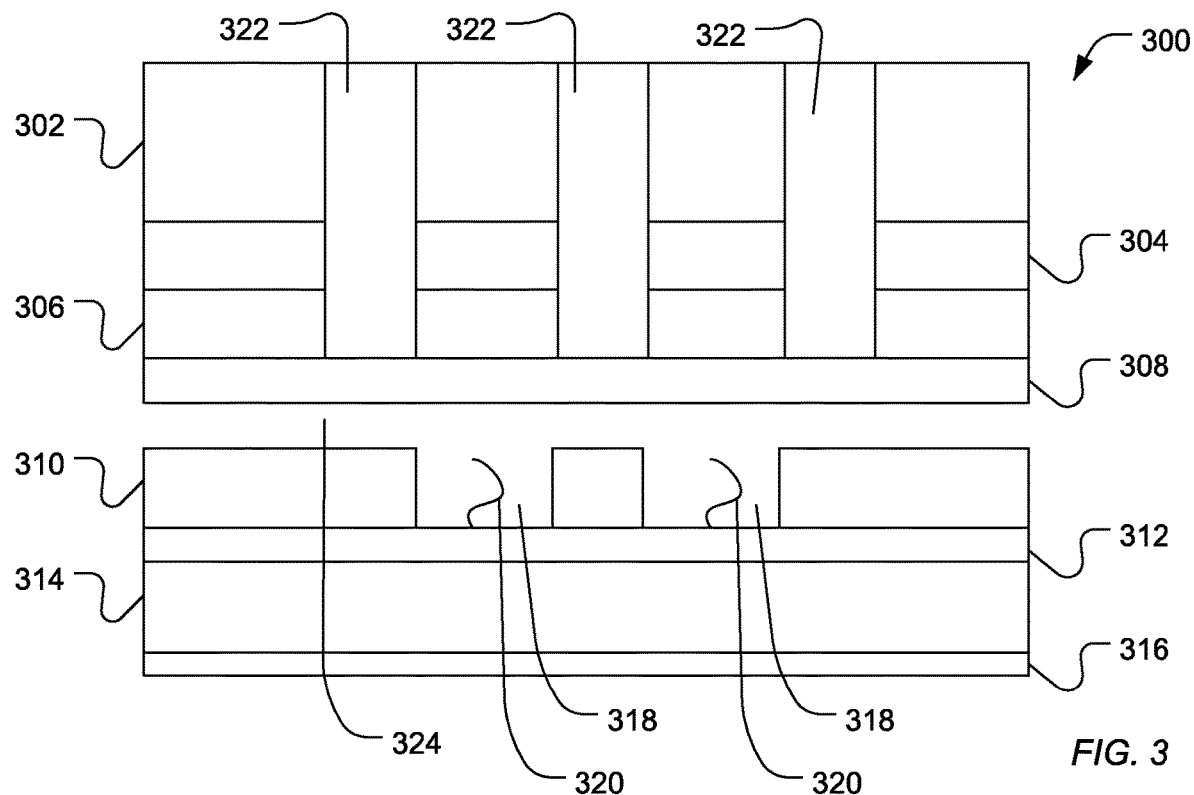
FIG. 3
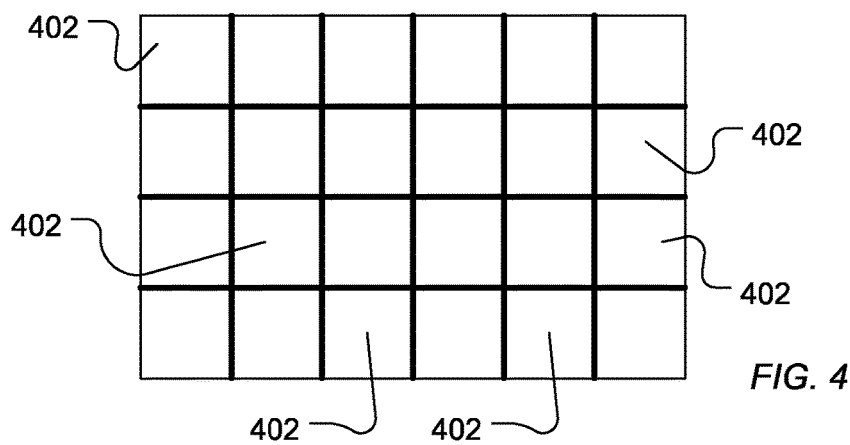
FIG. 4
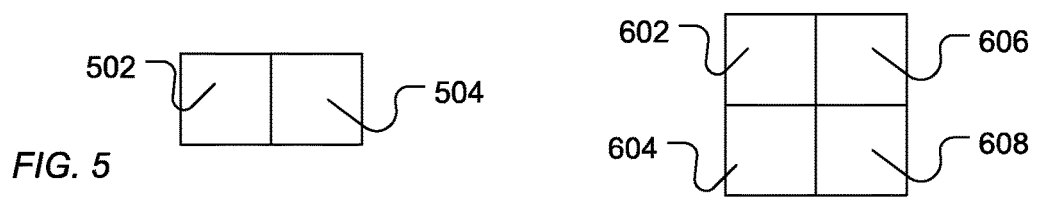
FIG. 5
FIG. 6

SYSTEMS AND METHODS FOR GENETIC SEQUENCING

CROSS-REFERENCE TO RELATED APPLICATION(S)

This application is a U.S. National Stage Application under 35 U.S.C. 371 of PCT Application No. PCT/US2014/032604, filed Apr. 2, 2014, which claims benefit of U.S. Provisional Application No. 61/808,105, filed Apr. 3, 2013, and claims benefit of U.S. Provisional Application No. 61/835,428, filed Jun. 14, 2013, each of which is incorporated herein by reference in its entirety.

FIELD OF THE DISCLOSURE

This disclosure, in general, relates to systems and methods for genetic sequencing.

BACKGROUND

Increasingly, genetic sequencing is being utilized in research and medicine. In particular, genetic sequencing is used to characterize, analyze, and manipulate characteristics of plants, for example, to improve productivity of food crops. Further, genetic sequencing is used in efforts to classify and characterize animals, including researching animal migration and species branching. In another example, genetic sequencing is used in medical research to identify genetic-based diseases, classify patient response to medicine or treatment, or determine characteristics indicating susceptibility to disease.

While many techniques are available for performing genetic sequencing, conventional techniques utilize extensive sample preparation, increasing costs associated with labor and consumables and introducing human error. Other techniques utilize large and expensive systems, increasing costs and lab space utilized by such techniques.

SUMMARY

In an embodiment, a system for genetic sequencing includes an integrated device having detectors for detecting signals indicating incorporation of a nucleotide during template-dependent nucleic acid synthesis along a target polynucleotide. The integrated device can further include a surface to which the target polynucleotide can be associated and defining a wall of a flow volume. The integrated device can further include an energy propagation layer or one or more filter layers. The system can include a fluidics system and a computational system in communication with the integrated device.

A method of genetic sequencing can include flowing nucleotides through a flow cell of an integrated device that includes detectors for detecting signals from the template-dependent incorporation of a complementary nucleotide. In some embodiments, the nucleotide includes an optically detectable label, and the method can further include providing excitation energy to the integrated device, the excitation energy either exciting a donor particle or molecule that energizes or excites the optically detectable moiety. Signals emitted during nucleotide incorporation are detected by the detector, leading to a determination of base identity for the incorporated nucleotide.

BRIEF DESCRIPTION OF THE DRAWINGS

The present disclosure may be better understood, and its numerous features and advantages made apparent to those skilled in the art by referencing the accompanying drawings.

FIG. 2 and FIG. 3 include illustrations of exemplary devices for performing genetic sequencing.

FIG. 4 includes an illustration of an exemplary pixel array.

FIG. 5, FIG. 6, FIG. 7, and FIG. 8 include illustrations of exemplary pixels.

The use of the same reference symbols in different drawings indicates similar or identical items.

DETAILED DESCRIPTION

Figure 1:
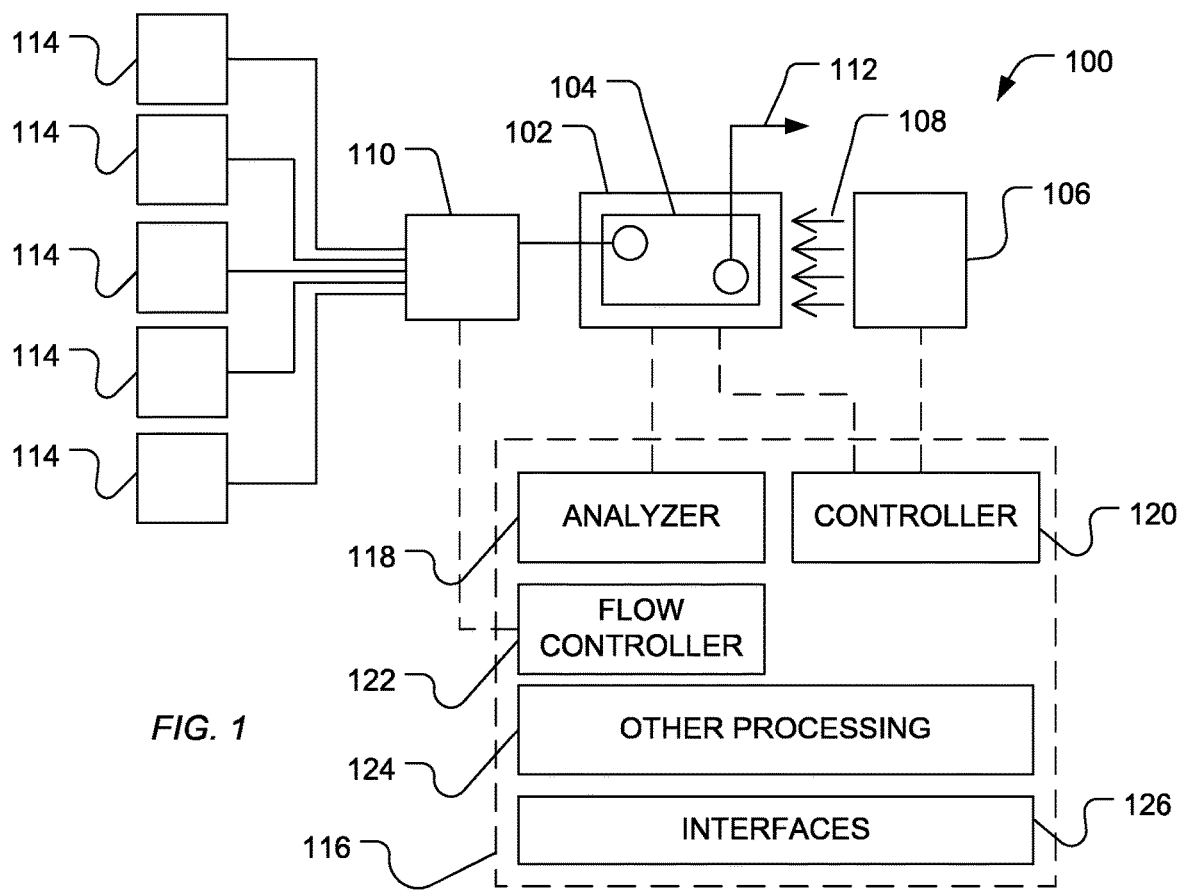
FIG. 1 includes an illustration of an exemplary system for genetic sequencing.

In an exemplary embodiment, a target polynucleotide is linked to a surface of a device and is exposed to nucleotides, such as labeled nucleotides. Signals indicative of nucleotide incorporation are detected by detectors integral to the device. Exemplary detectors can be pH sensors, heat detectors, photon detectors, or combinations thereof. The target polynucleotide can be linked to the surface directly or indirectly. For example, the target polynucleotide can couple with a probe bound to the surface or can be captured by an enzyme secured to the surface. In some embodiments, labels of labeled nucleotides fluoresce upon incorporation along the target polynucleotide, providing a fluorescent signal to be detected by detectors integral to the device.

In some embodiments, the disclosure relates generally to methods, as well as related compositions, systems, apparatuses and devices, for contacting a device with an enzymatic reaction, where the enzymatic reaction comprises a nucleic acid sequencing reaction. The nucleic acid sequencing reactions include any type of template-dependent sequence-by-synthesis method, including transient-binding reactions, optically-detectable reactions, energy transfer reactions (e.g., FRET), and dark nucleotide reactions (non-labeled nucleotides). In some embodiments, the device comprises an integrated device having detectors that detect signals from a nucleotide incorporation reaction, including any device described herein.

In an exemplary embodiment, a system includes an integrated device for detecting signals, e.g., fluorescence signals, indicative of nucleotide incorporation. In some embodiments, when a complementary optically labeled nucleotide is hybridized to, or is incorporated along a target polynucleotide, the label can emit an optically detectable signal. The signal from the label can be detected and used to determine base identity of the incorporated nucleotide. The system can include a fluidics system for feeding nucleotide solutions to the integrated device and can include computational systems for controlling the integrated device and for gathering data from the integrated device. The integrated device can further include a surface proximal to which a nucleotide is incorporated, for example, to extend a primer complementary to a target polynucleotide. The integrated device can further include detectors for detecting signals indicative of the nucleotide incorporation. Such signals can be emitted, for example, from fluorescent labels coupled to nucleotides to be incorporated and can result from fluorescence resonance energy transfer (FRET)-based fluorescence. Optionally, the integrated device can further include energy propagating layers for transferring energy to donors or a fluorescent dye, layers for filtering light to provide selectivity for a desired wavelength, and a lid to define a flow volume through which nucleotide solutions flow. Layers can include one or more substantially planar structures formed of materials having a desired physical, chemical, or optical property.

In an exemplary method, an integrated device is inserted into a system and coupled to communicate with a computational system and in fluid communication with a fluidics system. A target polynucleotide is applied at surface locations within the integrated device. Solutions including nucleotides modified with fluorescent dye are provided through the fluidics system to the integrated device. Fluorescent signals resulting from incorporation of nucleotides complementary to a target polynucleotide are measured by detectors forming a portion of the integrated device. Detected fluorescence is accessed by the computational device for further analysis.

In an example, FIG. 1 illustrates a system 100 for performing genetic sequencing. The system 100 includes an integrated device 102 including a flow cell 104 in fluid communication with a fluidics system. The fluidics system includes a plurality of reagent solution containers 114 in fluid communication with a valve structure 110, which is in fluid communication with a port of the flow cell 104 of the integrated device 102. Fluid flowing from the valve system 110 through the flow cell 104 passes to a waste port 112. The fluidics system is controlled by a flow controller 122 forming part of one or more computational systems 116. The flow controller 122 can selectively apply a reagent solution, such as a wash solution or one of one or more nucleotide solutions to the flow cell 104 of the integrated device 102. In an example, the integrate device 102 can incorporate a charge coupling device (CCD), a complementary metal oxide semiconductor (CMOS), or a digital signal processor. In a further example, the integrated device 102 can incorporate a capacitive transimpedence amplifier. In a further example, the integrate device 102 can include a photomultiplier tube.

The integrated device 102 can also be in communication with a controller 120 and an analyzer 118 of the computational systems 116. In addition, the computational systems 116 can include other processing systems 124 and interfaces 126, such as network interfaces and user interfaces. The computational systems 116 can be integrated into a single unit. Alternatively, the computational systems 116 can be remote from the remainder of the system, operating on a network, cloud, or other grouping of computational devices. In a further example, the controller 120 or other control circuitry can control temperature, wavelength fluorescent excitation power, pressure or other parameters.

The system 100 can further include an excitation source 106 to provide excitation energy 108 to the integrated device 102. For example, the excitation source 106 can provide laser light or electromagnetic energy to one or more layers of the integrated device 102. Such excitation energy 108 can provide energy to fluorescent dye or energy donors. Alternatively, such energy sources can be integrated into the integrated device 102. In a particular example, the controller 120 is in communication with the excitation device 106 and controls excitation of the integrated device 102 to selectively periodically excite donor particles or a dye, which provides energy to be emitted in response to nucleotide incorporation. In an example, the controller 120 can communicate both with the excitation source 106 and the integrated device 102 to provide fluorescent lifetime imaging. In another example, the excitation source 106 can interface with the integrated device 102 using a fiber optic faceplate. The excitation source 106 can be formed of light emitting diode (LED), such as an organic light emitting diode (OLED), or a LED of specific wavelength, such as a blue LED.

In a particular example, the reagent solutions 114 can include a wash solution, and a solution including four types of modified nucleotides, each type of nucleotide optionally modified with a different label having a different emission spectrum. The nucleotide solution can be applied to the integrated device 102. As nucleotides are incorporated to extend a primer complementary to the target polynucleotide, signals are emitted in a wavelength spectrum that corresponds with the incorporated nucleotide. The spectrum can be a narrow set of wavelengths or can be a set of wavelengths emitted by a dye or dyes associated with a type of nucleotide. Detectors within the integrated device 102 detect the signal and provide a series of signals to the analyzer 118 and other processing 124 to determine the sequence of one or more nucleotide bases that are incorporated to the extending nucleic acid molecule.

In another example, the reagent solution containers 114 can include a wash solution and a plurality of solutions that each includes a type of dye modified nucleotide, wherein each type of nucleotide is modified with a dye having the same or a different emission spectrum. The nucleotide solutions can be fed to the integrated device 102 sequentially. Fluorescent signals emitted as a result of nucleotide incorporation can be detected by detectors within the integrated device 102. Data associated with a series of detections can be provided to the analyzer 118 and other processing 124 for determining genetic sequence information.

In a particular example, a target polynucleotide is linked, directly or indirectly to a surface. Labeled nucleotides provide a signal upon incorporation that is detected by the integrated device 102 and provided to the analyzer 118. For example, a donor molecule or particle, such as a quantum dot (Qdot) nano-crystal, can be tethered to an enzyme, such as a DNA polymerase, without changing the functional properties of the enzyme. The donor molecule or particle absorbs light from a laser excitation source (e.g., source 106 or a source integrated with the device 102) and conditionally transfers energy to a labeled nucleotide depending on an incorporation event. Each of four nucleotides is terminally labeled with one of four different organic florescent dyes. Strands of the target polynucleotide are immobilized on a surface while the donor molecule or particle labeled enzyme binds to the primer-target complexes. The nucleotides are added to start the synthesis of DNA. When a nucleotide binds to the enzyme, due to close proximity to the donor molecule or particle, resonance energy is transferred to the nucleotide dye, which then emits its own light, for example, in the 600 nm-800 nm range. The light is collected and optionally spectrally separated and detected by one or more detectors associated with the location of the immobilized target polynucleotide. The label of the labeled nucleotide can be cleaved when the enzyme incorporates the nucleotide. Since the energy transfer occurs in the vicinity of the donor molecule or particle, the signal is spatially confined to the enzyme and the nucleotides in solution are rarely caused to emit light. This spatial separation of emissions keeps the background noise low. A second signal that indicates base incorporation comes from a measured decrease in intensity from the donor molecule or particle itself as it transfers energy to the nucleotide label.

In an exemplary embodiment, various features of the stimulation and detection system are integrated to increase performance and lower the cost of the system. The system is highly scalable, potentially achieving billions of simultaneous single molecule DNA sequencing runs on a single low cost substrate.

Figure 2:
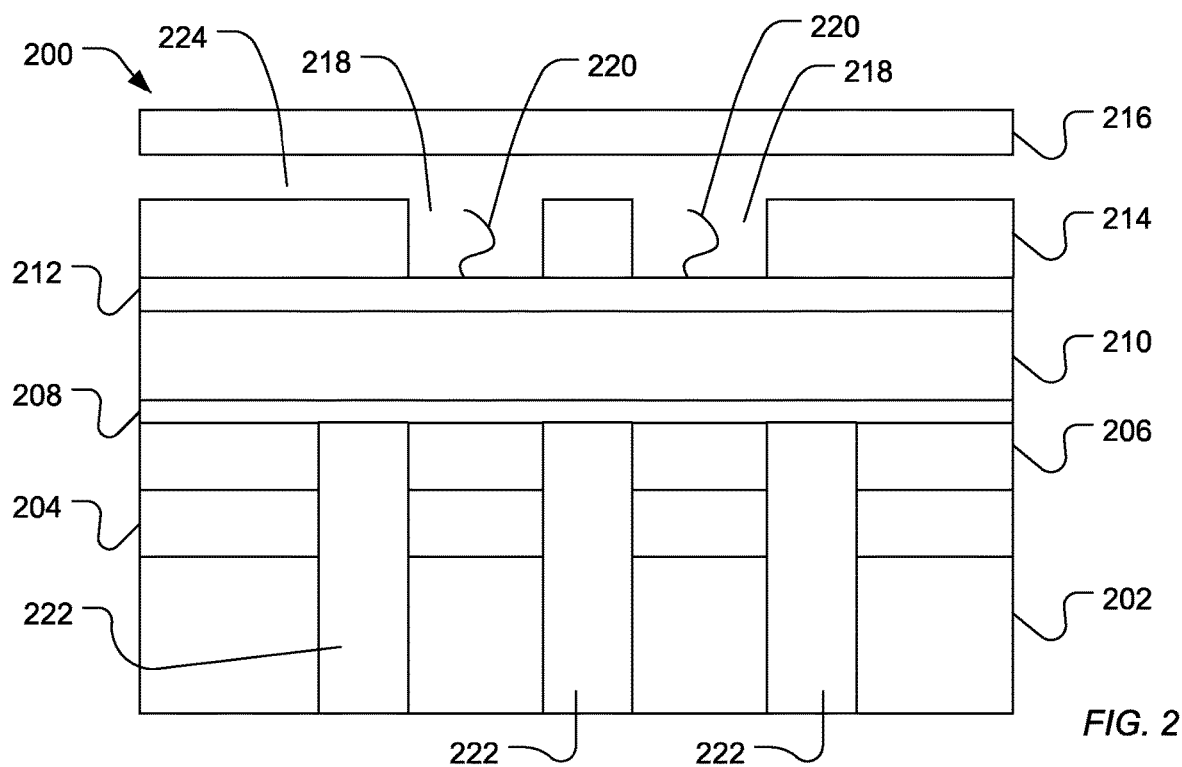

FIG. 2 includes an illustration of exemplary integrated device 200 in which detectors are formed within a substrate 202, such as a CMOS substrate. Optionally, the substrate 202 is created from a semiconductor material in which the excitation source is integrated along with the detecting elements. A flow volume 224 is defined between a lid 216 and a surface layer 212. Target polynucleotides 220 are coupled, directly or indirectly, to the surface layer 212 in regions defined over detectors defined within the layer 202. In particular, the target polynucleotides 220 can be captured proximal to specific treated areas of the surface 212 or within wells 218 defined by a well structure 214. For example, the target polynucleotide can be bound directly to the surface layer 212. In another example, the target polynucleotide can be captured by a complementary primer that is bound to the surface layer 212. In a further example, the target polynucleotide can be captured by an enzyme bound to the surface layer 212. In some embodiments, the target polynucleotide can be bound to a bead. In some embodiments, the substrate can be a planar substrate with a bead array or a substrate with wells, with the beads located in the wells. Optionally, the surface layer 212 can be formed of a fiber optic plate, a transparent ceramic, such as silica or alumina based materials, or like surfaces. Discrete sites on the surface layer 212 to which target polynucleotides are coupled can correspond with detectors within the substrate 202.

In an example, a functional semiconductor substrate is fabricated using complementary metal oxide semiconductor (CMOS) processing. Various implants are used to form photodiodes and transistors specific for detecting the incorporation events that can occur at very low intensity. When photons from the incorporation event fall onto the CMOS substrate, electron-hole pairs are created. In the case of a p-type substrate, holes are drained into the substrate, while the electrons are confined in potential wells until they are readout by proper circuitry containing transistors, electrodes or relevant parasitic structures. Although electron confinement is discussed, all similar principles are applied to hole confinement and readout. In a particular example, electron-hole pairs can be created at a depth in the silicon substrate that is dependent on wavelength of the radiation. For example, blue photons create electron-hole pairs near the surface of the silicon, while red photons create a majority of electron-hole pairs deeper than a few microns into the substrate. In an embodiment described in more detail below, a single pixel can be created in close proximity to the polymerase in which the "color" of the light can be differentiated by using multiple confinement wells at different depths within the substrate. For example, the single pixel can include at least two confinement wells, such as at least three confinement wells, but generally less than 10 confinement wells. The confinement wells can have a depth of not greater than 5 micrometers, such as not greater than 3 micrometers. In particular, a shallow confinement well can be centered around 1 micrometer depth and a deep confinement well can be centered around 2 micrometers depth. The number of electrons captured in each confinement well indicates which base is incorporated. The confinement well for the secondary signal (photons coming directly from the Qdot) can also be designed with selective sensitivity, most likely near the surface. A well capacity for the secondary signal can be created specifically for the parameters of the system. The wavelengths using the high levels of sensitivity can be designed to reduce surface states. If the secondary signal is large relative to the colored signals, a surface diode can be used, which normally has a higher dark current level, but is acceptable for sufficiently large signals. The other confinement wells can be "buried" with pinning implants to eliminate surface defect induced dark current. A CCD collection electrode may also be combined along with photodiode implants, creating a hybrid CCD/photodiode pixel. Such a configuration has advantages when different well capacities are used between the primary and secondary signals.

Optionally, the integrated device 200 includes an energy propagation layer 210, such as a layer that provides for total internal reflection (TIRF) or that provides for energy propagation creating an evanescent wave proximal to the target polynucleotides 220. In an example, the energy propagation layer 210 propagates energy, such as photonic energy, along a path that is generally parallel (e.g., TIRF) to the surface 212. In a particular example, an evanescent wave is produced by the propagation of energy in the energy propagation layer 210. The energy propagation layer 210 can include a transparent layer through which light or other electromagnetic energy is transmitted. Such a transparent layer can be formed of a transparent ceramic, such as silicon dioxide or indium tin oxide, or can be formed of a transparent polymer, such as a polycarbonate or a transparent fluoropolymer. In another example, the energy propagation layer can be formed of a material conducive to carrying electromagnetic energy in a plane parallel to the surface layer 212. Such materials can include thin conductive layers, such as metal layers. In an alternative example, the surface layer 212 forms the energy propagating layer and total internal reflection is caused by a difference in the index of refraction between an aqueous solution and the layer (212 or 210). In a further alternative, an excitation energy source can be disposed above the target polynucleotide 220.

The device 200 can further include a layer 208 to facilitate total internal reflection within the energy propagation layer 210. The layer 208 can be reflective to wavelengths associated with the excitation energy propagated through the energy propagation layer 210. In another example, the layer can have an index of refraction different from that of the energy propagation layer 210 and causing reflection of the propagating energy at particular incident angles.

In another example, the integrated device 200 can include a layer 206 to filter excitation energy propagating within the layer 210. In particular, the filter layer 206 can include materials that selectively permit transmission of wavelengths associated with fluorescent signals from dye of the modified nucleotides, but are at least partially opaque to wavelengths associated with excitation energy. For example, the filter layer 206 can include GaAs, polysilicon, CdS, CdSe, or a combination thereof.

In an additional example, the integrated device 200 can include a filter layer 204 to further filter fluorescent signals resulting from nucleotide incorporation into component spectra to be detected by detectors within the layer 202. An exemplary filter layer material includes doped silicon dioxide, doped zirconia, or another predominantly transparent material doped with a coloring agent.

Optionally, crosstalk prevention structures 222 can be provided that extend through one or more layers towards the energy propagation layer 210, defining pixels and preventing crosstalk of fluorescent signals between pixels. The crosstalk prevention structures 222 can extend through the filter layers, such as filter layers 204 or 206, and optionally within the substrate 202.

During operation, solutions including one or more nucleotides modified with fluorescent dyes can flow through the flow volume 224 and may or may not be incorporated to extend a primer along a target polynucleotide 220. Excitation energy can be provided through the energy propagation layer 210 which excites the fluorescent dye or optionally donor particles in proximity to fluorescent dye being incorporated along the target polynucleotide 220. During incorporation, the fluorescent dye of modified nucleotides fluoresces, and such fluorescence is detected by detectors within the substrate 202. Optionally, excess excitation energy is filtered by filter layer 206 and the fluorescence can be separated into different spectrum by the filter layer 204 to be detected by different detectors formed within the substrate 202. While the filter layer 206 for filtering excitation energy is illustrated as being further from the detector than the filter layer 204, the position of such filter layers can be reversed when both are included within the integrated device 200. Fluorescent signals from adjacent wells or regions on the surface structure 212 can be blocked by the crosstalk prevention structures 222.

FIG. 3 includes an illustration of another exemplary integrated device 300. A layer 302 in which detectors are defined is provided on an opposite side of the flow volume 324 from the surface 312 to which target polynucleotides 320 are proximal. The integrated device 300 can further include an energy propagation layer 314 and associated reflective layer 316. The energy propagation layer 314 can provide evanescent wave energy to facilitate fluorescence of modified nucleotides being incorporated along the target polynucleotide 320. The target polynucleotide 320 can be coupled, directly or indirectly, to specific locations on the surface layer 312 or can optionally be confined by wells 318 defined by a well structure 310, as described above. A transparent lid layer 308 can, with the surface layer 312, define the flow volume 324. The integrated device 300 can further include a filter layer 306 to filter excitation energy and can include a filter layer 304 to filter fluorescent spectrum into various detection spectrum, as described above. The integrated device 300 can further include crosstalk prevention structures 322 extending through one or more of the filter layers 306 or 304 and optionally into the layer 302 into which the detectors are formed.

In operation, nucleotide solutions including nucleotides modified with fluorescent dyes flow through the flow volume 324 and may be incorporated into or along a polynucleotide target 320. The dye associated with the nucleotide can be energized by a donor particle that is energized by an evanescent wave or can be energized by the evanescent wave itself. The evanescent wave can be provided by the energy propagation layer 314. Fluorescent signals resulting from the incorporation of the nucleotide along the target polynucleotide 320 can pass through the flow cavity 324 and the lid layer 308 and optionally through filters 304 or 306 for filtering excitation energy and separating fluorescence into various detectable spectrums by the detectors defined within the layer 302. Fluorescence from adjacent target polynucleotides can be prevented from impinging on other detectors by the crosstalk prevention structures 322.

The crosstalk prevention structures, such as 222 or 322, can be formed of reflective material or material that is opaque to the wavelength of excitation energy or the fluorescence spectra. For example, the crosstalk prevention structures 222 or 322 can be formed of metal, such as aluminum, copper, titanium, gold, silver, platinum, or any combination thereof. In another example, the crosstalk prevention structures 222 or 322 can be formed of polysilicon or doped polysilicon having a thickness sufficient to limit transmission of photons across the structure 222 or 322. When the optical detectors are electronic in nature, the crosstalk prevention structures can also be insulative.

As illustrated in FIG. 2 or FIG. 3, layers can be secured to one another directly or indirectly, such as through intermediate layers or by adhesives. For example, the surface layer 212 is indirectly secured to the substrate 202, by one or more optional layers, such as filter layers 204 or 206 or the propagation layer 210. In another example, the substrate 202 can be directly secured to a filter layer 204 by forming the filter layer 204 on the substrate using semiconductor processing techniques. In further examples, the different layers can be thermally bonded together, in particular, without intervening adhesive layers.

As illustrated in FIG. 4, detectors defined within a substrate can be grouped as pixels, such as pixels 402. Each pixel 402 can include one or more detectors arranged adjacent to each other within a horizontal plane or arranged to overlie one another and extending into a substrate. As illustrated in FIG. 4, pixels can be arranged within defined squares. Alternatively, pixels of other shapes and various orientations can be formed.

For example, FIG. 5 illustrates a top view of an exemplary pixel including a first detector 502 and a second detector 504 side-by-side in a plane. Each detector 502 or 504 may be responsive to different wavelength spectrum resulting from fluorescent signals of different dye. In another example, each of the detectors 502 or 504 can be similar in nature detecting a broad spectrum of wavelengths and having different filters associated with each detector 502 or 504.

Similarly, FIG. 6 illustrates a top view of a four detector pixel including exemplary detectors 602, 604, 606 and 608. As with the detectors of FIG. 5, the detectors are arranged adjacent each other when viewed from the top view. The detectors may each be configured to detect different wavelengths spectrum. In another example, the detectors can each be broad-spectrum detectors associated with different filters selective to the emission spectrum of particular dye. When using a dark nucleotide, the pixel can optionally have fewer than four detectors.

Figure 7:
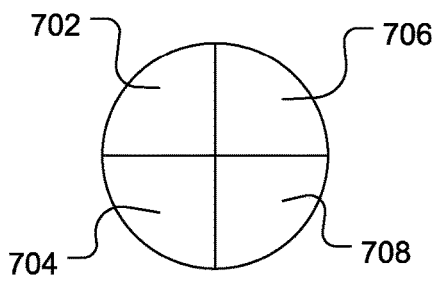

While FIG. 5 and FIG. 6 illustrate rectilinear shaped detectors, the detectors can alternatively be formed in various shapes. For example, FIG. 7 illustrates an exemplary circular pixel including quarter circle shaped detectors 702, 704, 706, or 708. When viewed from the top view, such detectors are adjacent one another, for example, directly adjacent or separated by an opaque divider or insulator. The detectors 702, 704, 706, or 708 can each be configured to detect a different wavelength spectrum or can be configured to detect a broad spectrum of wavelengths and be associated with different filters selective to the emission spectrum of particular dye.

Figure 8:
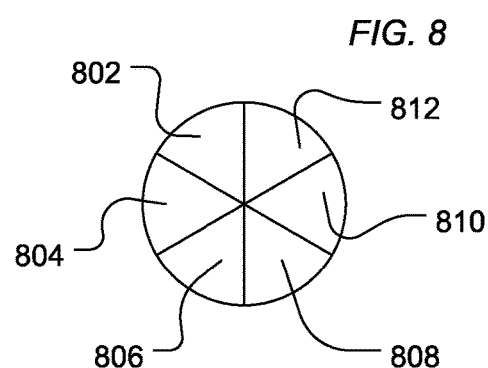

FIG. 8 illustrates a top view of an exemplary circular pixel including six detectors 802, 804, 806, 808, 810 and 812. Pixels can be formed to include four detectors for detecting four different wavelength spectrum associated with the fluorescence from four different dyes, each associated with a different type of nucleotide. In a further example, a five or six detector system can be defined which further includes detectors for excitation energy or background noise.

Figure 9:
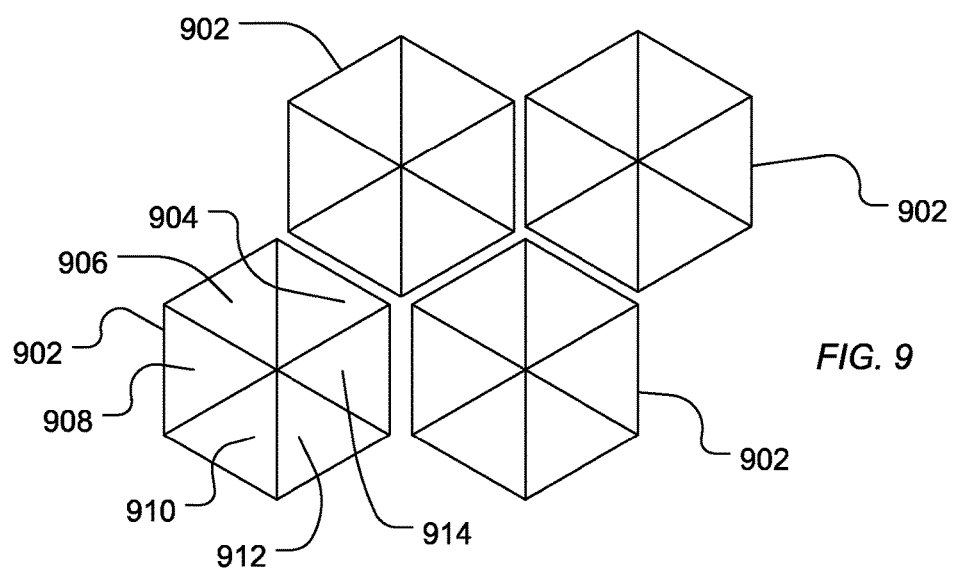
FIG. 9 includes an illustration of an exemplary pixel array.

FIG. 9 illustrates an alternative system that includes polygonal pixels 902. Such polygonal pixels 902 can include four or more detectors, such as detectors 904, 906, 908, 910, 912, or 914. The detectors can be selective to a particular spectrum associated with a particular dye or can detect wavelengths associated with excitation energy or background noise. Alternatively, additional detectors may be utilized in the above configurations for enhancing the detection area associated with wavelength spectrum of dye that is more difficult to detect than fluorescence from other alternative dye. In further examples of the above pixel configurations, an emitter, such as a light emitting diode can be incorporated into each pixel.

Figure 10:
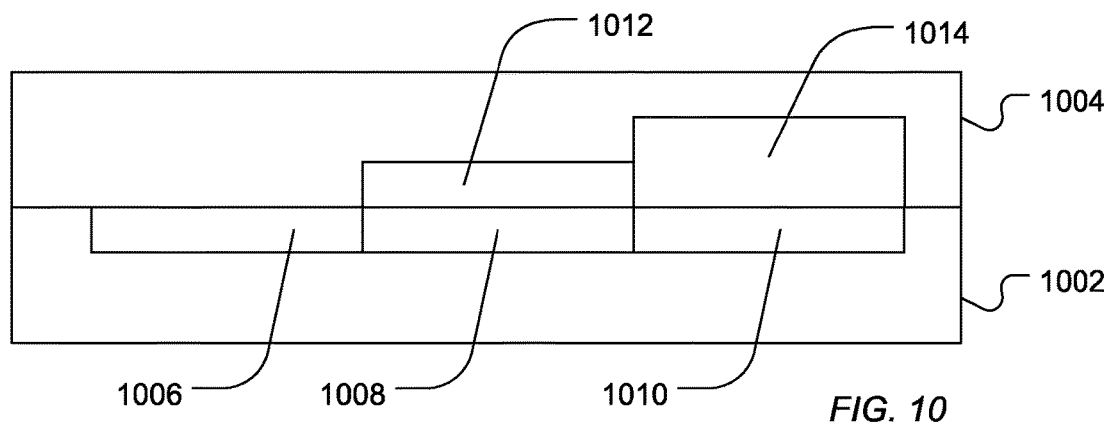
FIG. 10 and FIG. 11 include illustrations of exemplary pixels.

In an example, one or more layers can be provided that filter specific wavelengths from the emitted signal. In such an example, generic detectors can be utilized underlying different filters and resulting in the detection of different wavelengths of light within the various detectors. In particular example, layers of various thickness of material that is semi-opaque to fluorescence emitted by the fluorescent dyes can be utilized to filter fluorescent light before it impinges various detectors. For example, as illustrated in FIG. 10, a layer 1002 can include detectors 1006, 1008, or 1010. In an example, the layer 1002 is a polysilicon layer or gallium arsenide layer in which detectors 1006, 1008, and 1010 and associated circuitry are formed. Structures of different thickness are formed over different detectors and are formed of material that is semi-opaque or provides resistance to photons of different wavelengths. For example, different thicknesses of polysilicon, gallium arsenide or other semi-transparent ceramics or polymers can be applied over the layer 1002 including the detectors 1006, 1008, 1010. For example, the detector 1006 can be free of a structure, where as the detector 1008 can be associated with a structure 1012 having a first thickness and the detector 1010 can be associated with the structure 1014 having a different thickness. Such structures 1012 and 1014 can be embedded within a transparent material, such as a silicon dioxide, zirconium dioxide, indium tin oxide or other transparent material. Owing to the nature of the penetration of photons of different wavelengths, wavelengths that are more red in nature can penetrate the structure 1014, activating the detector 1010, wavelengths that are green in nature can penetrate structure 1012 and activate the detector 1008. In a further example, wavelengths that are more blue in nature can activate the detector 1006 while other wavelengths penetrate through the detector 1006 without activating it. While red, green and blue are described to illustrate the nature of the technique, the technique can be extended to other wavelengths by adjusting layer thickness. In such a manner, the nature of the wavelengths that result in a reading within a detector 1006, 1008, or 1010 is a function of the thickness of the associated structure, such as structure 1012 or structure 1014.

In a particular example, the thickness of the polysilicon is adjusted for each color. For example, a thick polysilicon layer absorbs blue and green but may allow the majority of red photons to pass through. A pixel with no polysilicon layer may allow all colors to pass through. In the simplest form, two pixels, one containing a polysilicon layer and one without a polysilicon layer, can be used to differentiate four different nucleotide incorporation events. These absorption layers can be implemented at the silicon substrate or after backend metal layers are processed along with the dielectric layers. Employing absorption layers in both the frontend of the process and the backend of the process gives additional options for selectivity.

Figure 11:
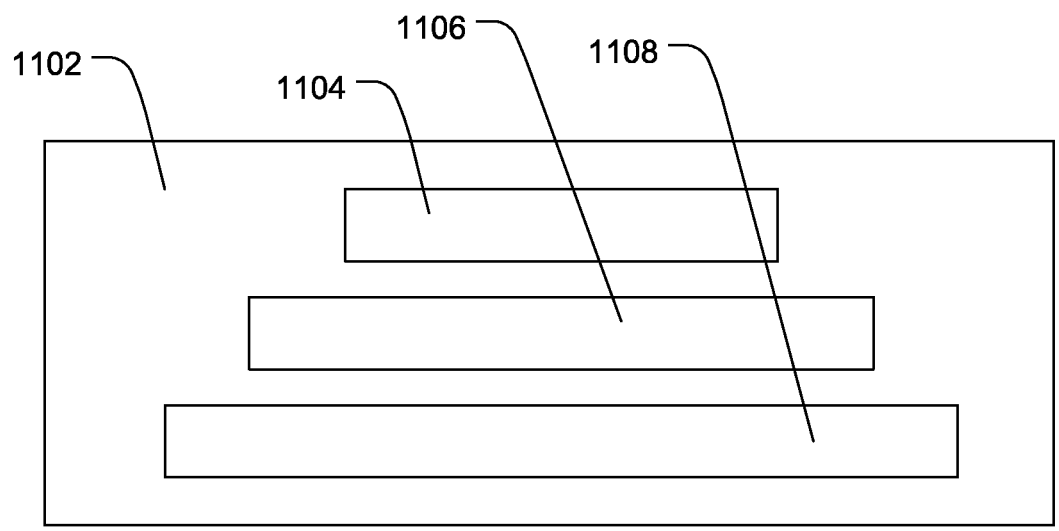

In an alternative example, illustrated in FIG. 11, a cross-section of a semiconducting structure 1102 illustrates detectors 1104, 1106, 1108 disposed over one another. Fluorescent signals of different wavelengths penetrate the cross-section of the semiconductor structure 1102 to differing levels resulting in the activation of the detectors 1104, 1106, or 1108 depending upon the nature of the wavelength of the signal passing through the semiconductor material 1102. In particular, longer wavelength spectrum activate deeper detectors where as shorter wavelength spectrum are prevented from passing further into the semiconductor material and activate more shallow detectors. Such is particularly the case for features formed within polysilicon or similar semiconductor materials. Alternatively, a combination of the structures of FIG. 10 and FIG. 11 can be used to detect multiple wavelengths using less area.

Figure 12:
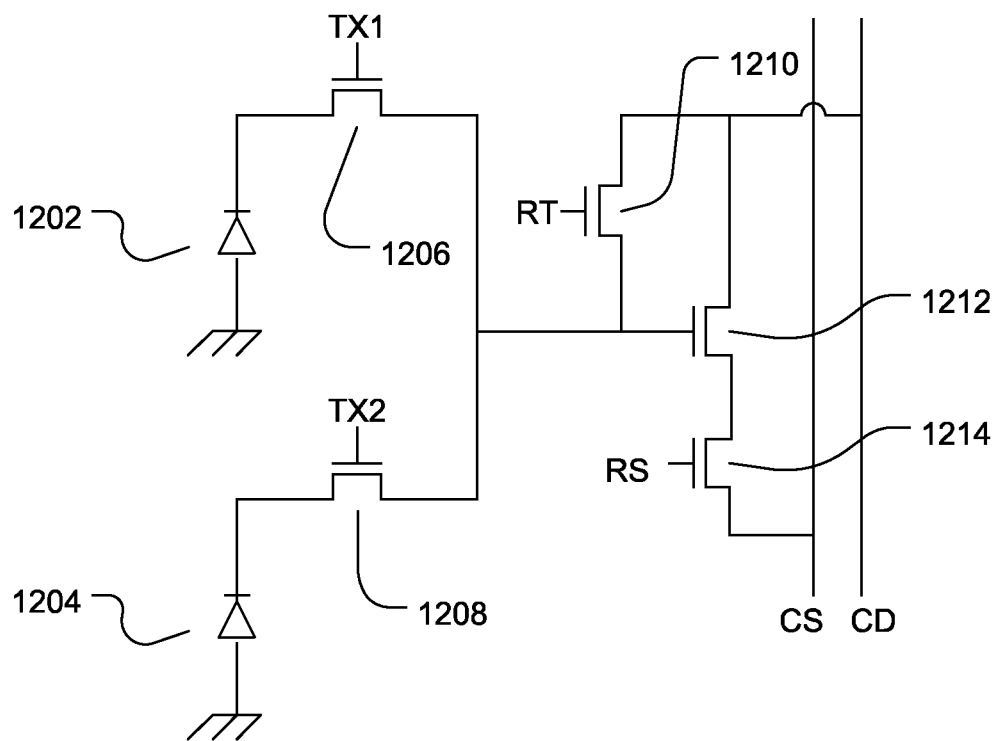
FIG. 12 includes an illustration of exemplary circuit diagram.

FIG. 12 includes an illustration of exemplary circuitry for detecting charge within two levels of a CMOS device. Each diode 1202 or 1204 is fully depleted during charge transfer. A pixel first transfers the shallow charge from 1202 by activating TX1 (1206). The floating diffusion is reset with RT (1210). Correlated double sampling is used to remove thermal noise. The deep charge is transferred by activating the TX2 (1208). Three samples can be used for removal of thermal noise. Such a circuit configuration can, for example, be used in conjunction with exemplary device cross-sections illustrated in FIG. 13 and FIG. 14.

Figure 13:
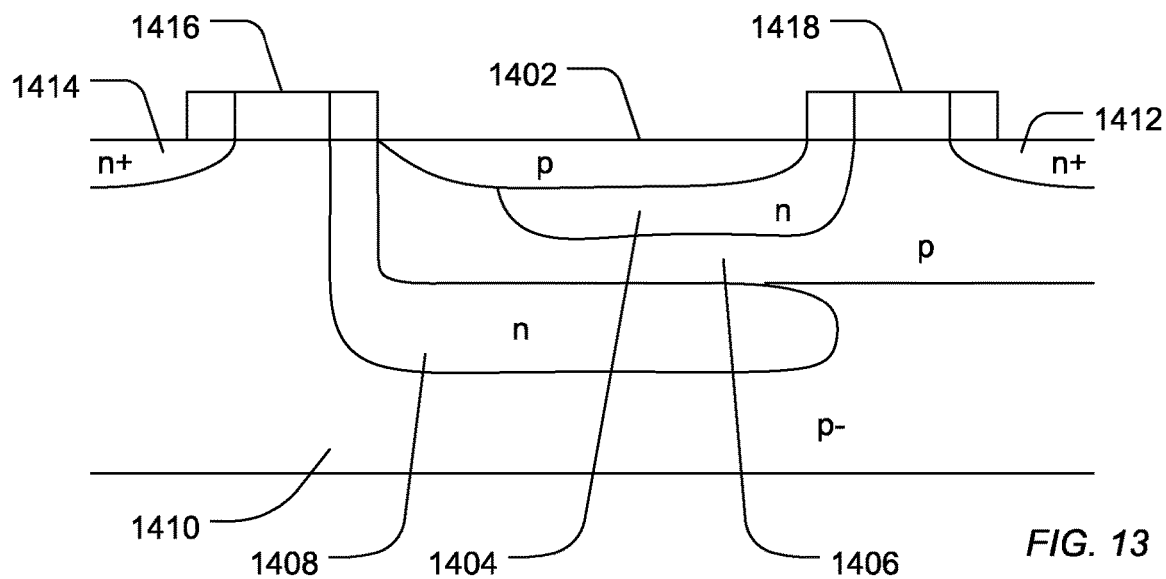
FIG. 13 and FIG. 14 include illustrations of exemplary detectors formed in a substrate.

FIG. 13 includes an illustration of exemplary double pinned photodiode. After polysilicon 1410 deposition, a deep implant 1408 is formed, patterned and annealed. The deep implant 1408 can also be formed at the beginning of the CMOS in processes using lower energy. Compensating implant 1406 reduces the size of the deep implant and creates a barrier between the deep implant 1408 and the shallow implant 1404. The shallow implant 1404 is self aligned to the second electrode 1418. After silicon nitride gate spacers are formed, a p-type layer 1402 is implanted and annealed.

In an alternative example, the deep implant 1508 is not self aligned with the polysilicon and is made with a single energy and dose. The native p-epitaxy region 1510 forms the barrier between the shallow junction and a narrow junction.

The pixel is read with the shallow junction first being fully depleted before the deep junction charge is transferred. A p-type implant 1506 at an electrode 1518 creates a sufficient barrier to prevent charge transfer from the deep junction to the floating diffusion 1512. Since the epitaxy region 1510 is lightly doped, it is depleted easily to the depth of the deep implant 1508. When the electrode 1516 is switched to high potential, the electrons in the deep implant are transferred to the floating diffusion 1514. Consequently electrons in the shallow junction 1504 may also be transferred during the cycle. For this reason, the shallow junction should be empty first. Alternatively, the shallow junction can be pulled back sufficient distance from the electrode 1516, which may decrease the quantum efficiency of the shallow junction.

Figure 15:
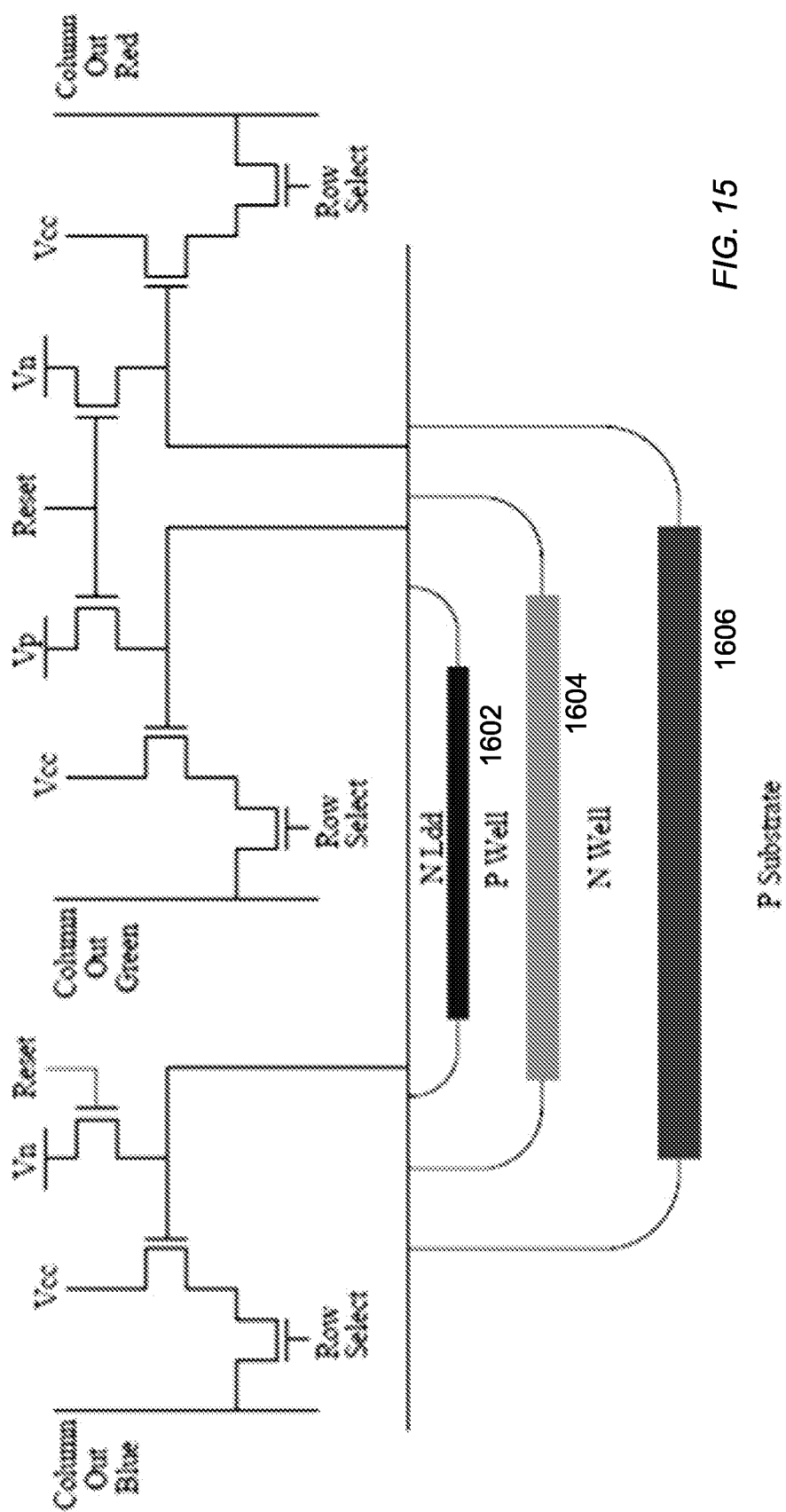
FIG. 15 includes an illustration of exemplary circuit diagram and substrate.

FIG. 15 illustrates a further exemplary construction in which regions 1602, 1604, or 1606 each include associated circuitry for selectively detecting charge within the layers and thus providing spectral selection based on the depth of the layers within the CMOS device. In an example, each well can be reset to a type specific charge when reset is selected. In particular, p-type wells can be reset to Vp, or n-type wells can be reset to Vn. In response to a row select, each color can be read through a separate column channel.

Figure 16:
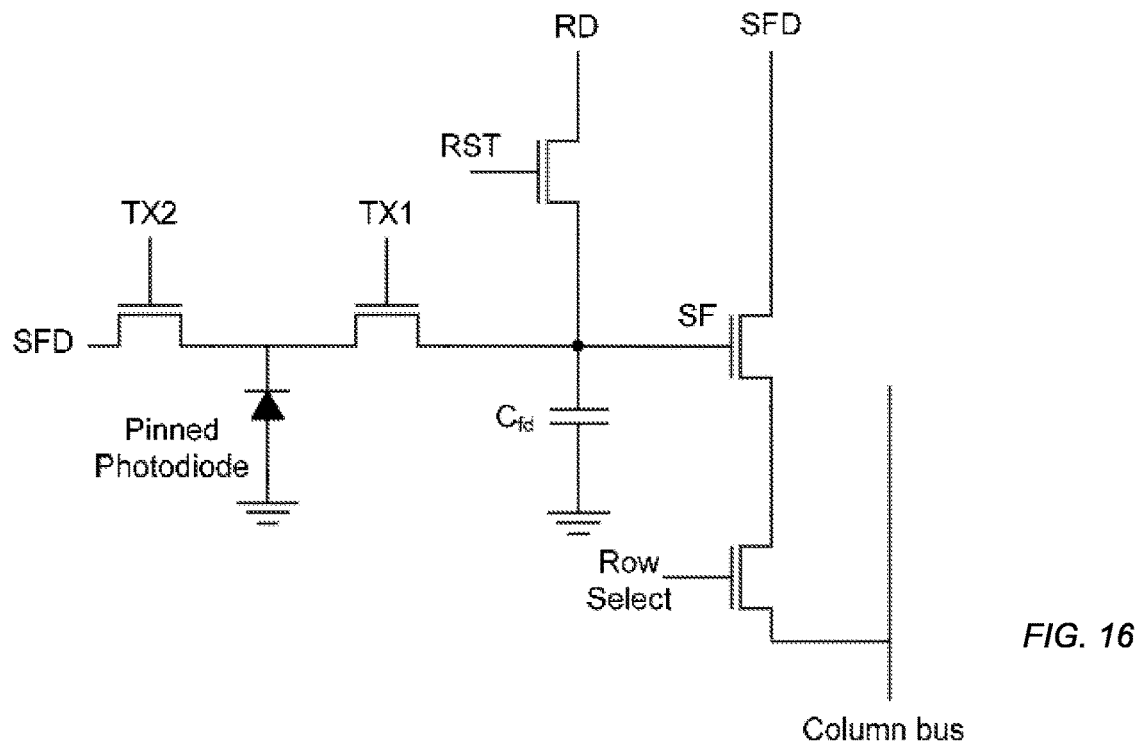
FIG. 16 and FIG. 17 include illustrations of exemplary circuit diagrams.

FIG. 16 illustrates an alternative circuitry utilizing a single pinned diode. Such architecture provides a low noise. The photodiode can be charged by activating TX2 when TX1 is off and can be read by activating TX1 when TX2 is off. Charge from the photodiode is transferred to the node and activates the transistor associated with SF. A resulting signal is provided to the column bus when the associated row is selected. The capacitor $C_{fd}$ can be reset by activating RST.

Figure 17:
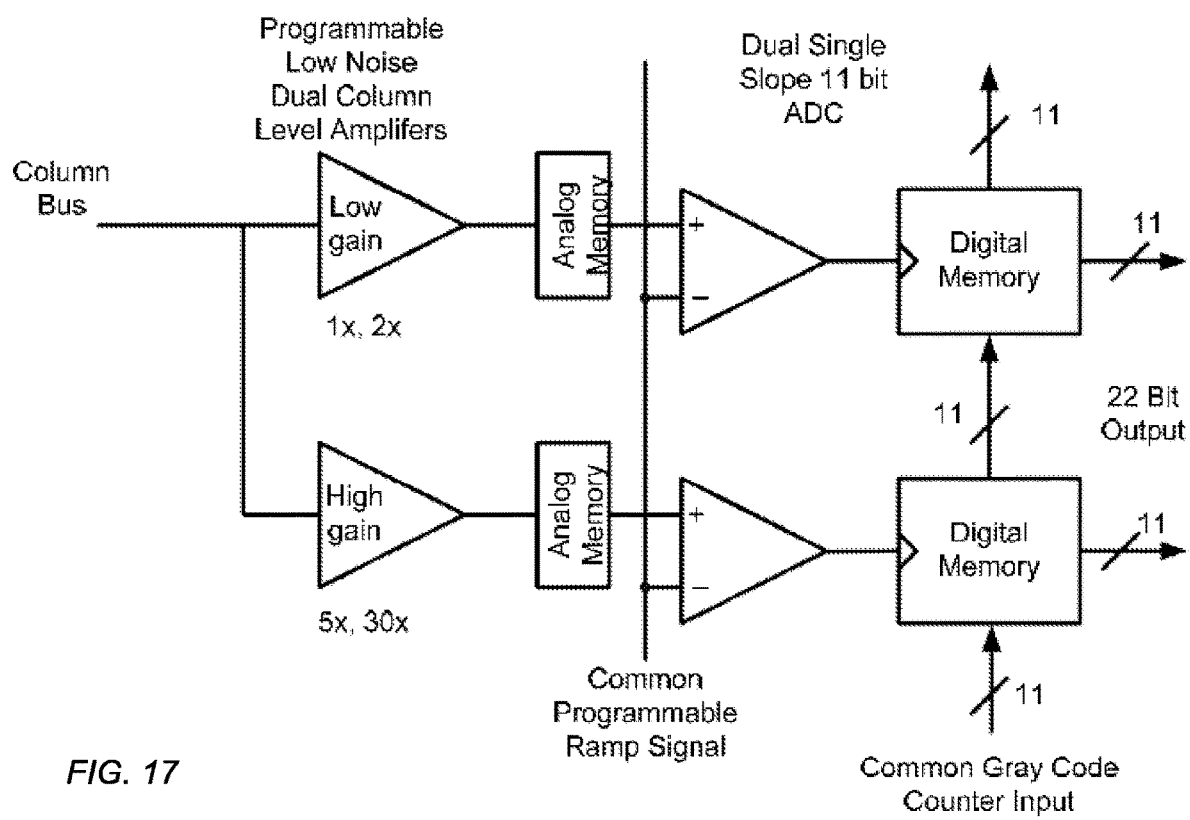

FIG. 17 includes an illustration of an exemplary structure for extracting data from the system. Data enters from a column bus and passed through a low gain or a high gain filter. The data is digitized and stored in a digital memory for output. When using the high gain path, the system can deliver as much as 200 frames per second (fps) or more (e.g., 120 fps to 1028 fps) and provides a dynamic range of 8 bits or higher (e.g., 8 bits to 32 bits).

Figure 18:
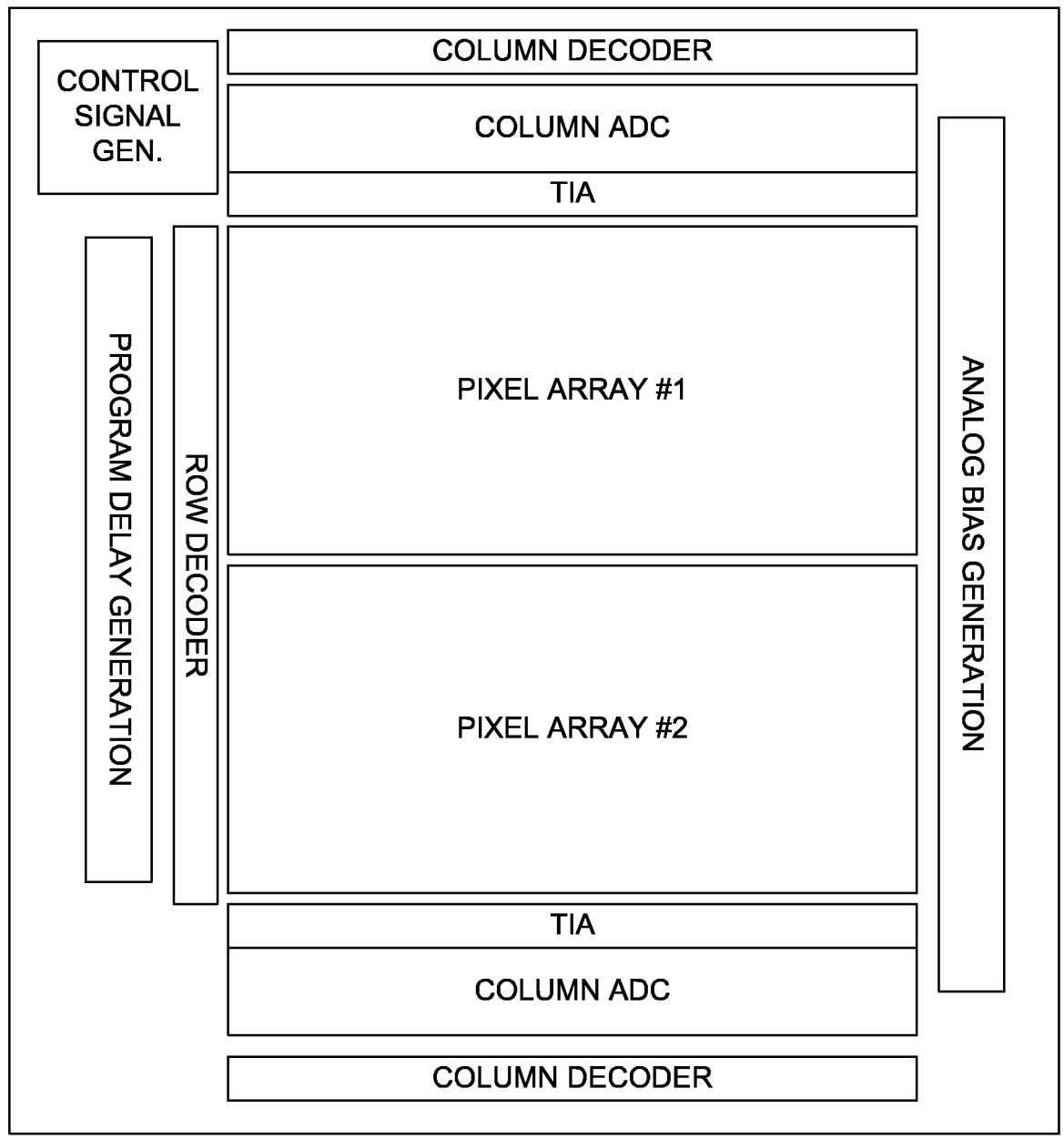
FIG. 18 and FIG. 19 include illustrations of exemplary chip architectures.
Figure 19:
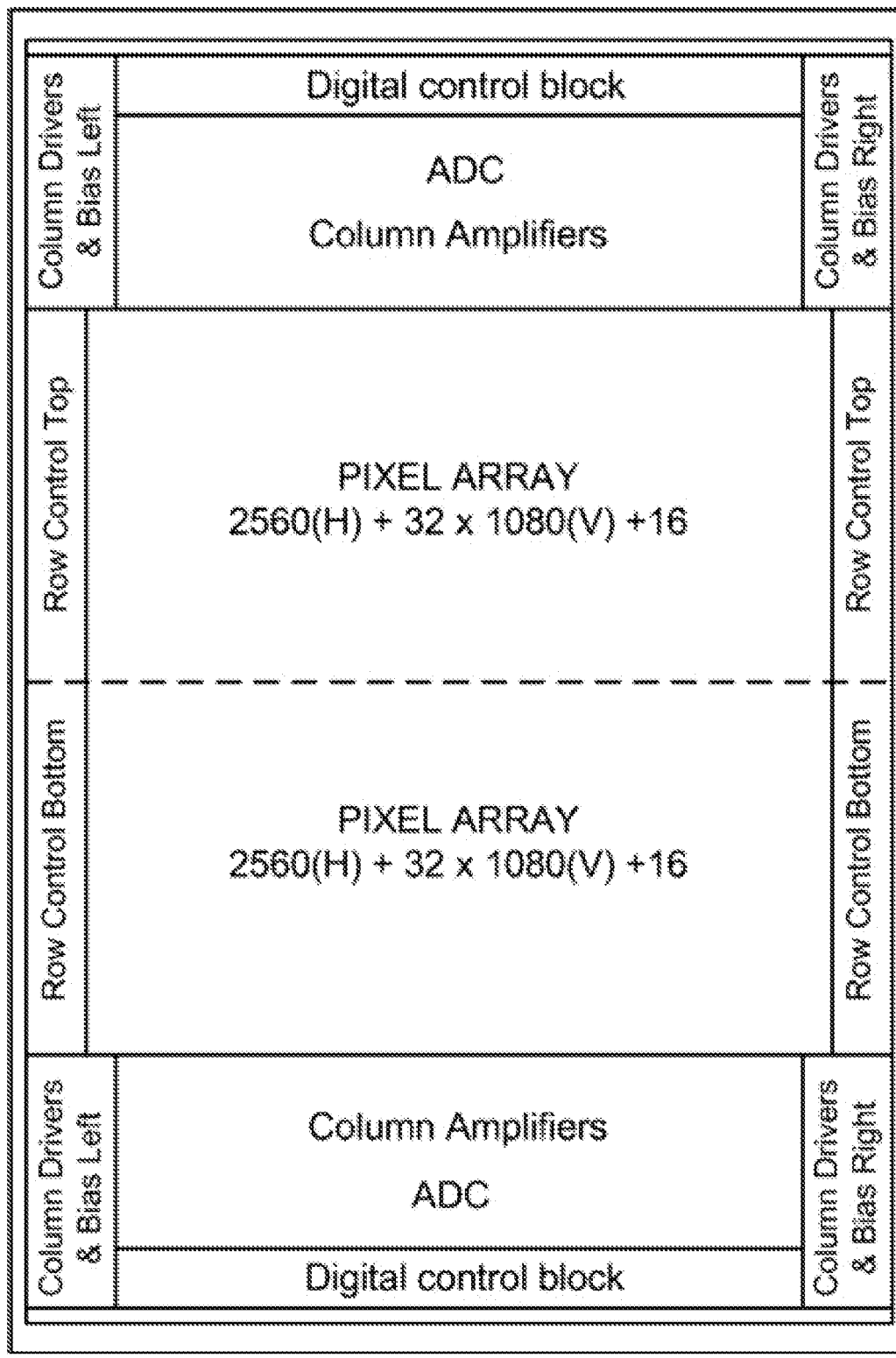

FIG. 18 and FIG. 19 illustrated chip architectures for use by the integrated device and the circuitry of the integrated device. Each architecture includes more than one pixel array, such as first and second pixel arrays, each associated with column amplifiers and column analog-to-digital converters. In addition, the architecture includes column decoders. By splitting the pixel array into one or more units, and accessing the units separately more data can be collected through the array. In a particular example, the multi-array combination can include as many as 300 M or more detectors having a pixel size of 3 µm or less, such as less than 2 µm. Pixel arrays can be arranged in multiples of 2160×2560 or higher aspect ratios. Further, such CMOS integrated devices can access the data at greater than 200 frames per second and 8 bits and an RN of 2 e– at 200 fps. When using four detectors per pixel, the chip may include at least 75 million pixels with a data flow rate of 270 GB per hour.

Figure 14:
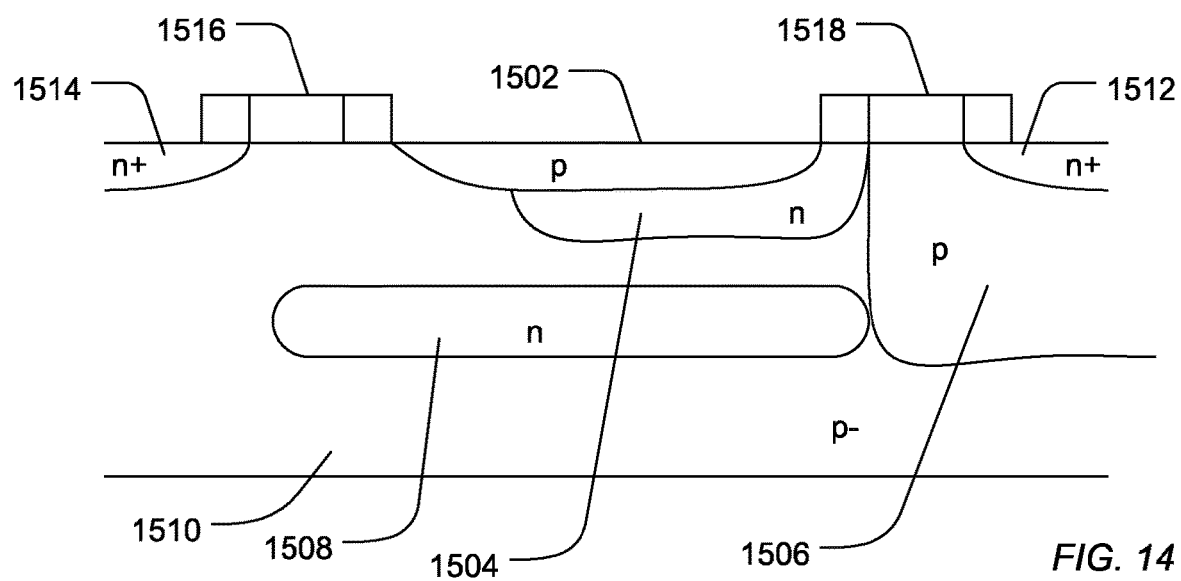

Since the incorporation events occur asynchronously over the course of the DNA synthesis, a high frame rate is used to capture incorporation events. It is advantageous to reduce the data at each incorporation site to build high density systems. The data at each site can be limited to the color of the nucleotide and whether or not the event is a true incorporation, utilizing 3 bits. For example:

000—no incorporation
001—no incorporation
010—no incorporation
011—no incorporation
100—Red labeled nucleotide
101—Orange labeled nucleotide
110—green labeled nucleotide
111—yellow labeled nucleotide A mapping of these bits to the depth of the confined photo charge within two confinement wells can be used with the confinement wells illustrated, for example, in FIG. 13 or FIG. 14. To provide three bits from each incorporation site, comparison thresholds may be implemented within the circuitry local to the incorporation site. The bit that determines whether an incorporation has occurred or not can come from the secondary signal or from a decision rule based on the total intensity within a pixel. Since the photodiodes at each incorporation site act as a memory, the required frame rate can be fast enough that two incorporation events cannot occur within a frame interval.

Figure 20:
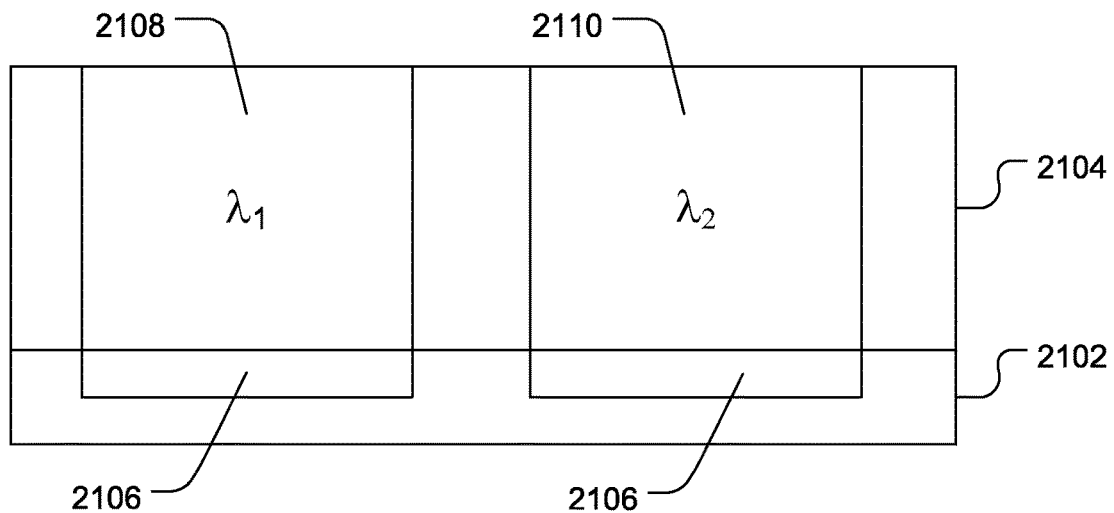
FIG. 20 includes a cross-section illustration of exemplary filter layer.

In addition or alternatively, the system can include filters that filter fluorescence into various wavelengths to be provided to different detectors. Although the spectral content of the primary signal can be separated by confining the photogenerated electrons at multiple depths within silicon, other methods may also be effective. Pigment or dye based organic color filters can be patterned above each pixel using photolithography methods. At least two different colors can be used to differentiate between four labeled nucleotides. Absorption filtering may also be effective by fabricating polysilicon layers above each pixel as shown above in FIG. 10. Regarding patterned color filters, FIG. 20 illustrates a cross-section of a device including a CMOS device layer 2102 including detectors 2106. A filter layer 2104 includes doped regions 2108 and 2110, each doped with a different dopant so that the region 2108 or 2110 are selective for a different wavelength spectrum ($\lambda_1$ or $\lambda_2$). In such a manner, similar detectors 2106 can be utilized to detect different wavelength spectrum based on the filtering of associated regions 2108 or 2110.

Figure 21:
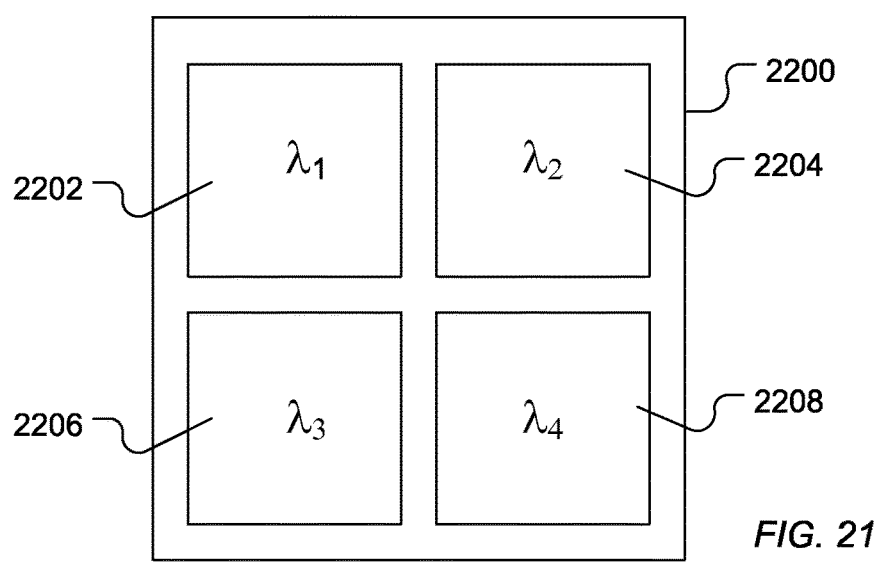
FIG. 21 includes a plan view illustration of an exemplary filter.

FIG. 21 illustrates a top view of a similar system. Within the filter layer 2200, regions 2202, 2204, 2206, or 2208 can filter different wavelength spectrum $\lambda_1$, $\lambda_2$, $\lambda_3$, or $\lambda_4$. Detectors residing underneath such a filter 2200 can detect different wavelength spectrum.

Figure 22:
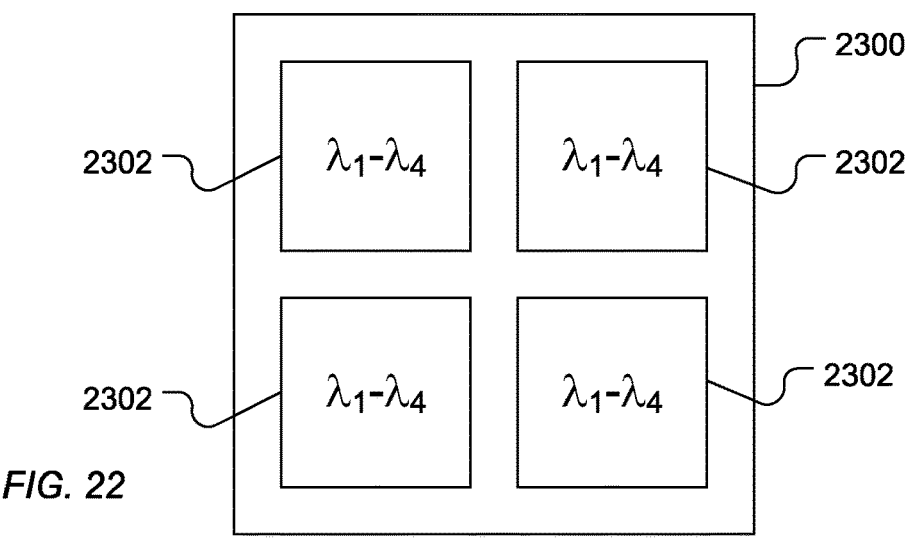
FIG. 22 includes a plan view illustration of exemplary excitation energy filter.

An additional filter layer can be provided that filters excitation energy but permits the wavelength spectra emitted from fluorescent dye to pass through the filter. For example, FIG. 22 illustrates a top view of a set of filter regions within a filter layer 2300. Each filter region 2302 permits passage of the wavelength spectrum $\lambda_1$-$\lambda_4$ associated with fluorescence signals from dye while being spectrally selective against wavelengths associated with excitation energy. While the filter layer 2300 is illustrated as being subdivided into regions 2302 that are spectrally selective, a uniform filter layer can be provided that is spectrally selective for the wavelengths emitted by different fluorescent dye associated with nucleotide incorporation.

Figure 23:
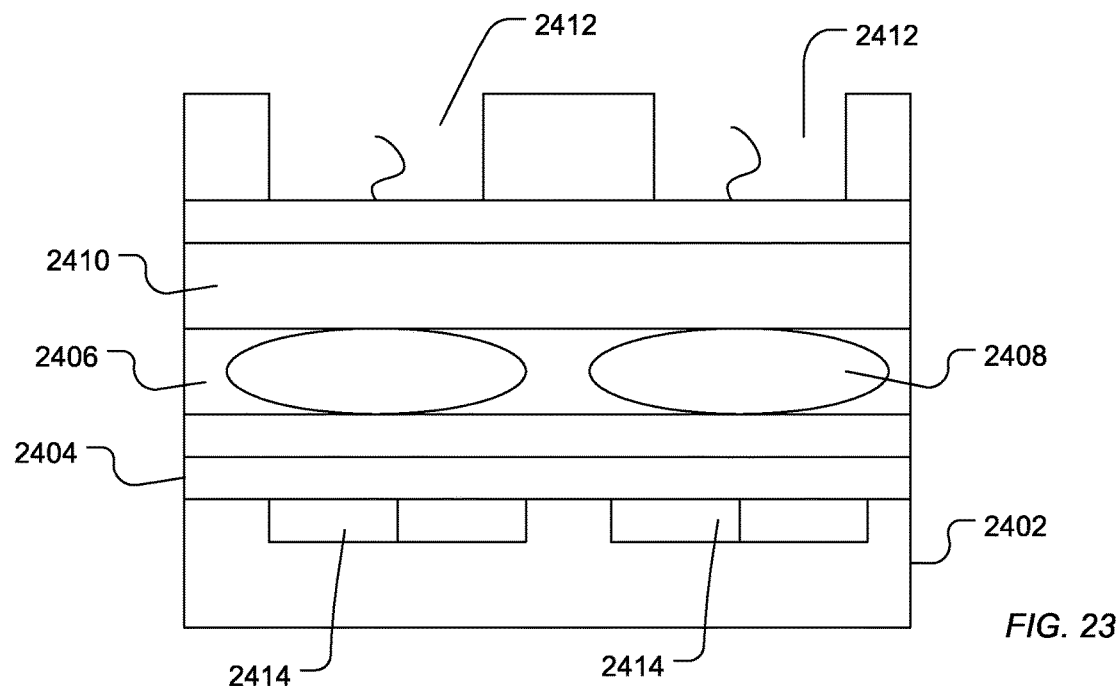
FIG. 23 includes an illustration of exemplary integrated device.

Optionally, a microlens configuration can be utilized to focus emitted fluorescence onto detectors. For example, the integrated device can include a layer incorporating microlenses. As illustrated in FIG. 23, a CMOS layer 2402 that includes detectors 2414 can be situated on an opposite side of a microlens layer 2406 from regions 2412 in which fluorescence occurs as a result of nucleotide incorporation. For example, the integrated device can include an energy propagation layer 2410. A microlens layer 2406 can be disposed below the energy propagation layer 2410 and filter layers 2404 can be disposed between the microlens layer 2406 and the detector layer 2402. The microlens layer 2406 can include microlenses 2408 aligned between the regions 2412 and the detectors within the detector layer 2402.

Figure 24:
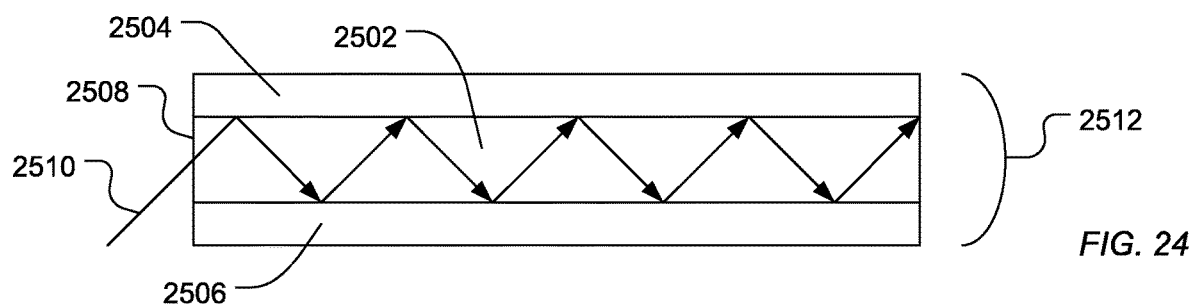
FIG. 24 and FIG. 25 include illustrations of exemplary excitation layers.

Energy propagation layers that provide total internal reflection of excitation energy can be used to provide an evanescent wave within the solution. Such evanescent waves can energize donors which donate energy to fluorescent dye or can energize the fluorescent dye itself. In a particular example, excitation light can be received from an external source. For example, as illustrated in FIG. 24, energy propagation layer 2502 can be positioned between two reflective layers 2504 and 2506. Such layers 2504 or 2506 can act as reflective layers based on a difference in refraction index relative to the energy propagation layer 2502. Alternatively, the layer 2504 may be absent and reflection can result from a difference in refractive index with an aqueous solution. An external source 2510 provides light through a surface 2508 which undergoes total internal reflection. Optionally, a mirrored surface 2512 is provided which reflects propagating light, further containing the light within the layer 2502 and preventing the light from exiting the integrated device. The propagation of the light 2510 within the layer 2502 creates an evanescent wave that energizes donors or fluorescent dye in proximity to the layer 2504.

Figure 25:
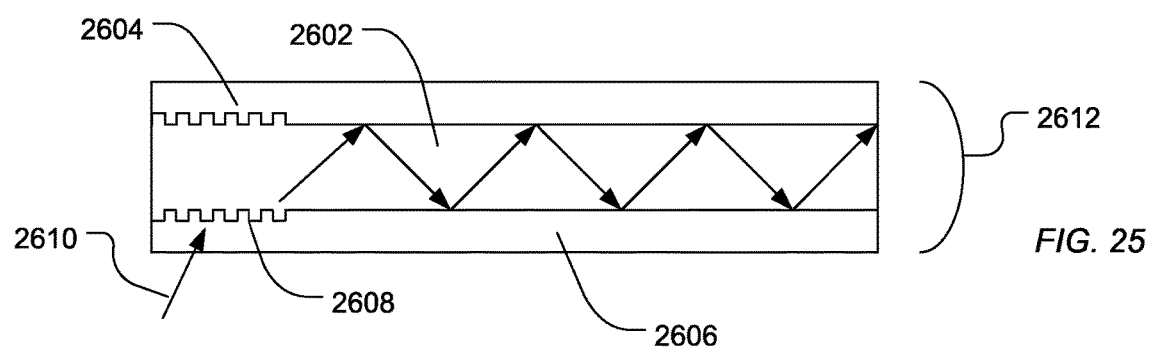

In another example illustrated in FIG. 25, the energy propagation layer 2602 is optionally positioned between the reflective layers 2604 and 2606. External excitation energy 2610 is applied to a refractive grating 2608, altering the path of the light to angles that result in total internal reflection within the layer 2602. As with FIG. 24, optional mirrored surface 2612 can prevent the light from exiting the energy propagation layer 2602.

Figure 26:
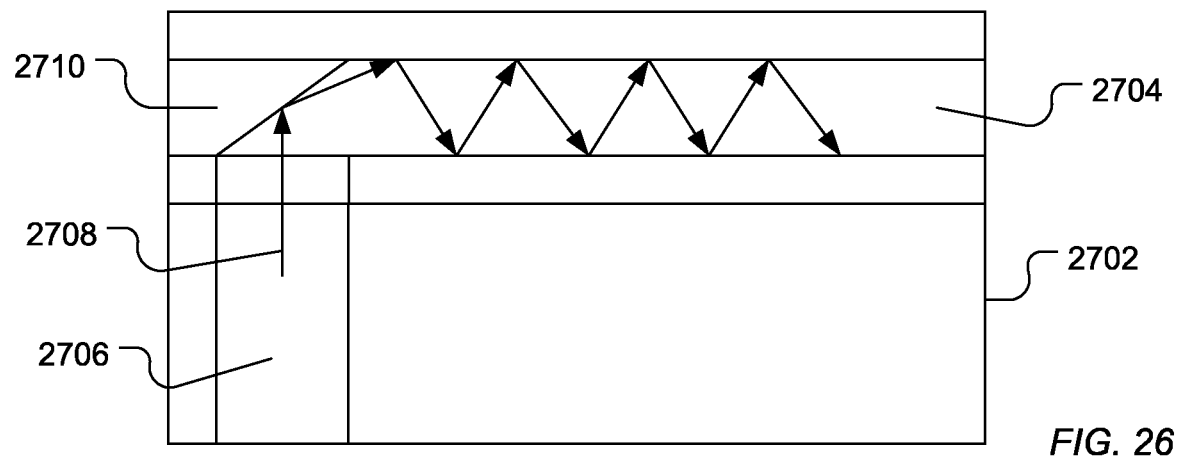
FIG. 26, FIG. 27, and FIG. 28 include illustrations of exemplary integrated devices.

In a further example, an energy source, such as a light emitting diode (LED) or other energy source, can be integrated within the device. For example, as illustrated FIG. 26, the integrated device 2702 can include an energy propagation layer 2704. An energy source, such as a LED device 2706, emits energy 2708 which is reflected or refracted based on a structure 2710 and propagates through the energy propagation layer 2704. The structure 2710 can be a refractive grating, reflective surface, or other structures for facilitating total internal reflection within the energy propagation layer 2704. Instead of using an external light source, the CMOS substrate, if advantageous, can be designed to emit its own light source.

In a particular example, light emitting diodes (LEDs) are created at each pixel location working on the principle of hot carrier direct recombination. The light source is modulated in conjunction with the readout of the photodiodes to tune the system for response. Since the light source can be bound to the silicon substrate, and local to the incorporation site, the donor molecule or particle may be removed, because the light source interacts with the labeled nucleotides that are bound to the polymerase during the incorporation, keeping the background noise low, while simplifying the system. The light source can be constantly modulated while the photodiodes are readout during the off-cycles. If a label lights up and is detected by the pixels at the incorporation site, it most likely comes from a nucleotide that is incorporated into the DNA. Therefore, if the polymerase is bound to the pixel and the light source is local to every pixel, then direct stimulus of the labeled nucleotide can be used and effectively detected.

Figure 27:
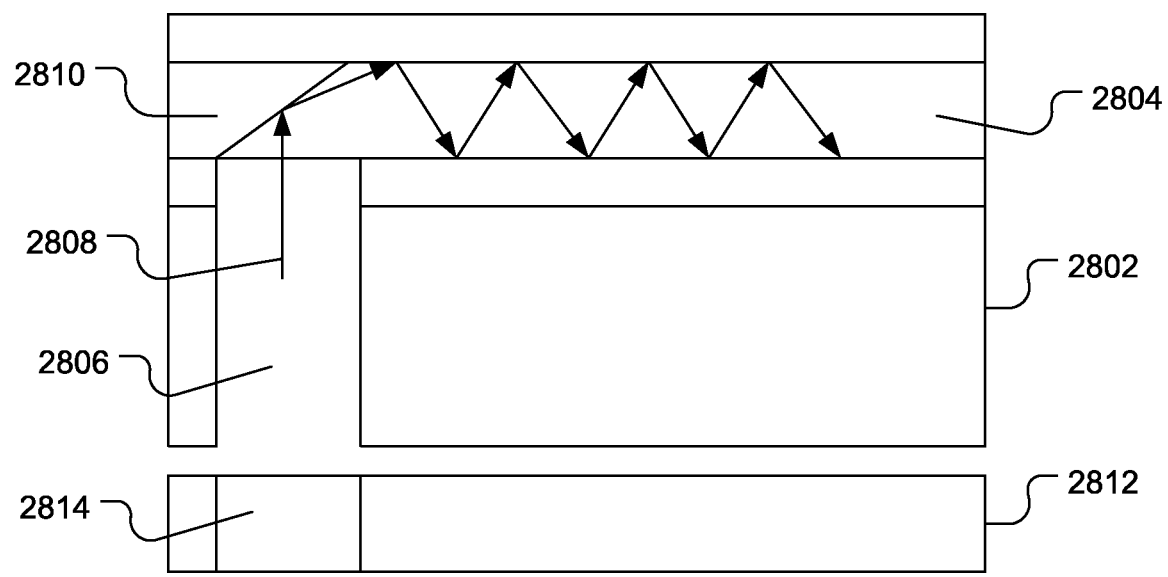

In a further alternative illustrated in FIG. 27, an integrated device 2802 can include a via or opening 2806 through which energy 2808 can be transmitted. Alternatively, the via or opening 2806 can be filled with a transparent material. The energy can be refracted or reflected by structure 2810 causing total internal reflection within the energy propagation layer 2804. In an example, the structure 2810 includes a refraction grating or a reflective surface. In such an example, an interface 2812 interfacing with the device 2802 can include a light source 2814. Such a light source can be an LED built-in to the interface 2810 or can be an optical fiber or light pipe aligned in the interface with the via 2806 of the device 2802 to provide light or energy 2808 to the energy propagation layer 2804. In particular, the interface 2812 can be formed as part of the system, for example, illustrated in FIG. 1, which accepts a sequencing device incorporating the integrated device 2802.

Figure 28:
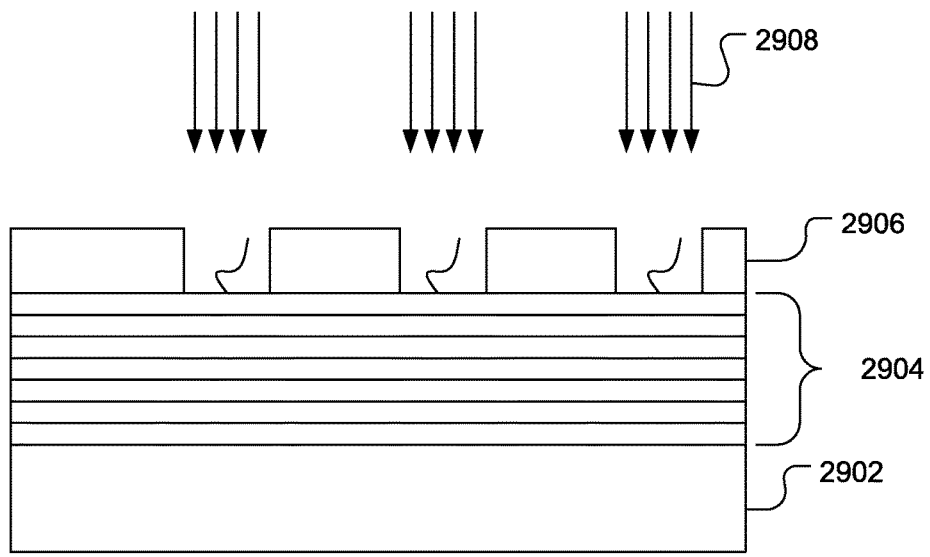

In a further alternative, excitation energy can be provided from an external source directly to the donor particles or dye without propagating to a detector. For example, FIG. 28 illustrates an exemplary device in which excitation energy 2908 is provided to the surface layer 2906. Such excitation energy is prevented from impinging detectors within the CMOS layer 2902 by an interference filter including multiple layers of material having different indexes of refraction. For example, such an interference filter 2904 can include alternating layers of silicon dioxide and silicon nitride or other similar materials. The thickness of such alternating layers can provide reliable selectivity for fluorescent signal wavelengths and filter wavelengths associated with excitation energy. For example, alternating layers of silicon dioxide and silicon nitride can be selectively formed to permit transmission of fluorescent light associated with signals resulting from nucleotide incorporation while preventing transmission of excitation light. In such a way, excitation light can be provided from an external source without an energy propagation layer while still being prevented from interfering with detection of the fluorescent emissions.

Figure 29:
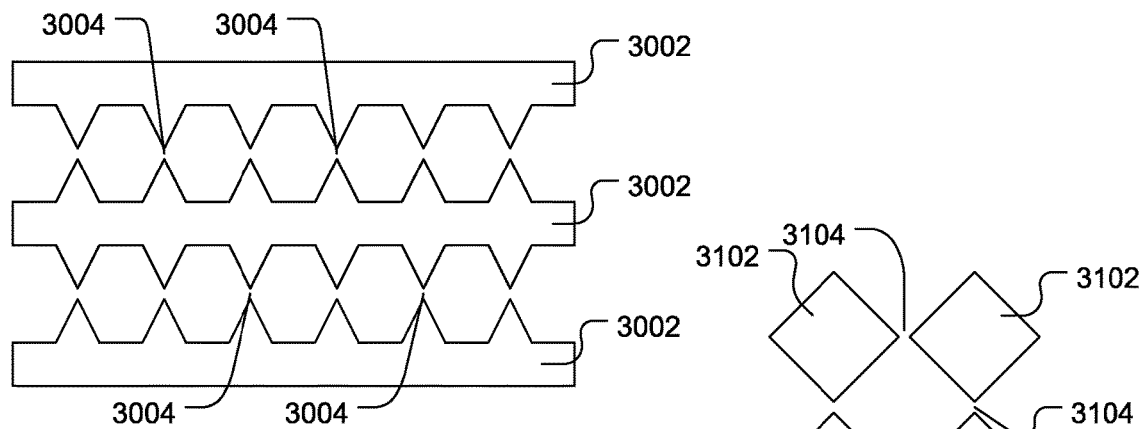
FIG. 29, FIG. 30, and FIG. 31 includes illustrations of exemplary evanescent wave focusing structures.
Figure 30:
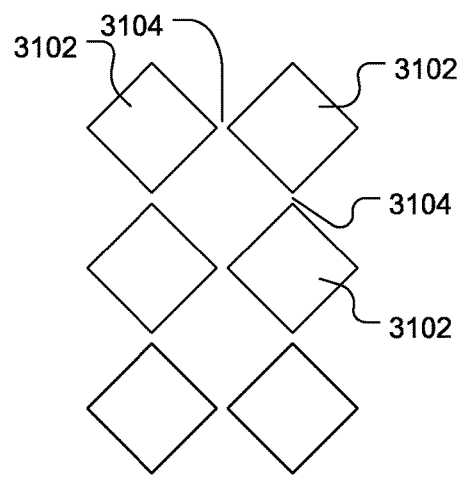
Figure 31:
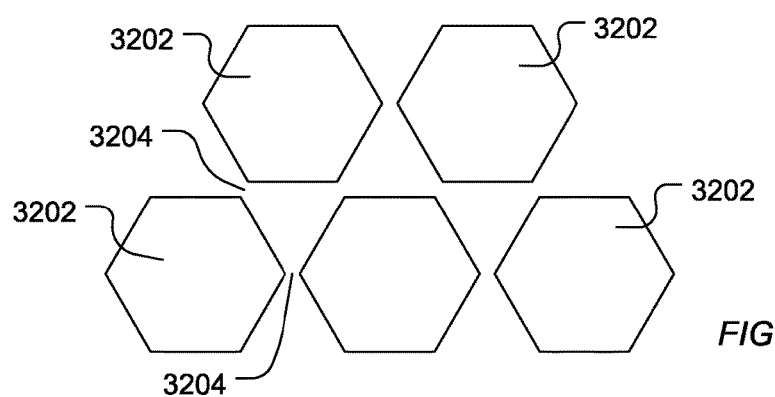

In another example, when a wave or energy propagation layer is utilized, additional structures can be formed proximal to the energy propagation layer to enhance the evanescent wave within particular regions. For example, conductive structures can be formed that provide edges and points configured to enhance or concentrate such evanescent waves within small regions. As illustrated in FIG. 29, structures 3002 can be formed having points converging on regions 3004. Such regions when positioned above an energy propagating layer provide an enhanced evanescent wave for exciting donor particles or molecules or dye molecules. Similarly other patterns can be formed, such as the pattern illustrated in FIG. 30 including squares 3102 defining proximity regions 3104 or as illustrated in FIG. 31 including polygons 3202 defining regions 3204 that have an enhanced evanescent wave.

Many types of florescent labels may be used and some may have advantages over others depending on the stimulator that is integrated within the silicon substrate. For example, a local RF signal may be generated at each incorporation site. The RF power may be absorbed by the label and emitted as visible light sensed by the detection pixels.

Figure 32:
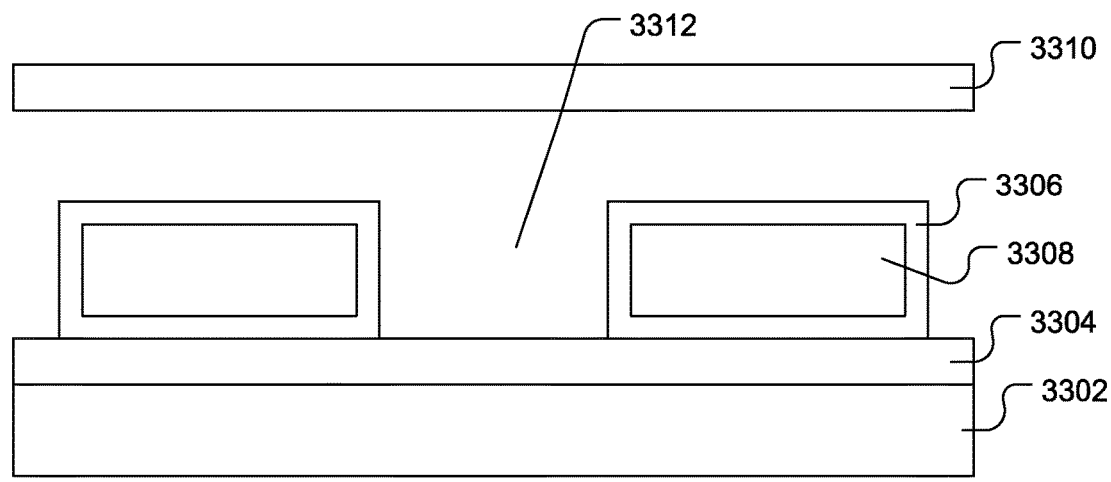
FIG. 32 includes an illustration of an exemplary device.

A target polynucleotide can be localized, linked or otherwise secured to a surface such as through hybridization to a complementary primer, or can be captured by an enzyme secured to the surface. The surface can be formed of transparent or semitransparent material permitting the transmission of fluorescent emission to a detector. In an example, the flow of target polynucleotides into regions to be detected can be controlled by electromagnetic potential or charge. In an example illustrated in FIG. 32, the device includes a transparent electrode 3304 overlying other layers 3302 and defining a surface in proximity to which nucleotides can be incorporated along a target polynucleotide. For example, the electrode layer 3304 can be formed of indium tin oxide (ITO), flouring doped tin oxide, doped zinc oxide (e.g., aluminum doped zinc oxide), poly(3,4-ethylenedioxythiophene) (PEDOT) and similar polymers, carbon nanotube networks, grapheme, or combinations thereof. In an example, an electrode of opposite charge can be formed within a layer 3310 defining a flow volume over the system. A potential difference between the electrodes 3304 and the electrode 3310 can drive polynucleotides into a flow region 3312 associated with a detector. In another example, an electrode 3308 can be defined within a well structure. The electrodes 3308 can be surrounded by dielectric layer 3306. Such an electrode 3308 can, for example, be formed of a doped polysilicon which is oxidized on an outer surface to provide the insulating layer 3306. Such an electrode structure 3308 can be utilized along with the electrode 3304 or the electrode 3310 to drive polynucleotides into a well structure or region 3312 or to stretch or compress such polynucleotides.

Figure 33:
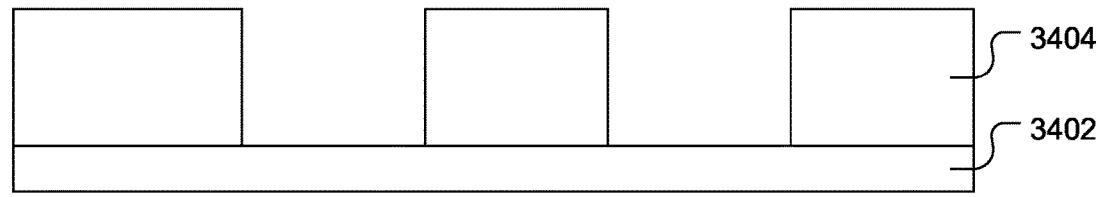
FIG. 33 and FIG. 34 include illustrations of exemplary surfaces for securing a polynucleotide sample.

As illustrated in FIG. 33, wells can be defined over a surface 3402 using a well structure 3404. In particular, the well structure 3404 can be formed of material that assists with total internal reflection in the propagation layer. For example, the well structure 3404 can be formed of a polymeric material having an index of refraction similar to that of water. In an example, the polymeric material includes Cytop®. In another example, the well structure 3404 can be formed of a material that is reflective, such as a metallic material including aluminum, copper, titanium, gold, silver, platinum, or a combination thereof.

Figure 34:
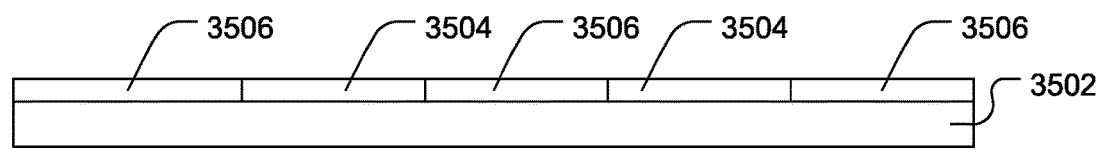

In another example, pad regions can be formed on a surface to which polynucleotides or enzymes can be selectively attached. As illustrated in FIG. 34, pads 3504 can be applied over a layer 3502. In between the pads 3504 can be a polymer material 3506 that prevents attachment of polynucleotide species or enzymes. For example, the pads 3504 can be formed of titanium, zirconium, gold, or other materials. In a further example, the pads 3504 can be formed of metallic surfaces, such as gold, silicon, copper, titanium, and aluminum; metal oxides, such as silicon oxide, titanium oxide, and iron oxide; plastics, such as polystyrene, and polyethylene; zeolites, or other materials. In an example, the polymer includes polyethylene glycol.

Figure 35:
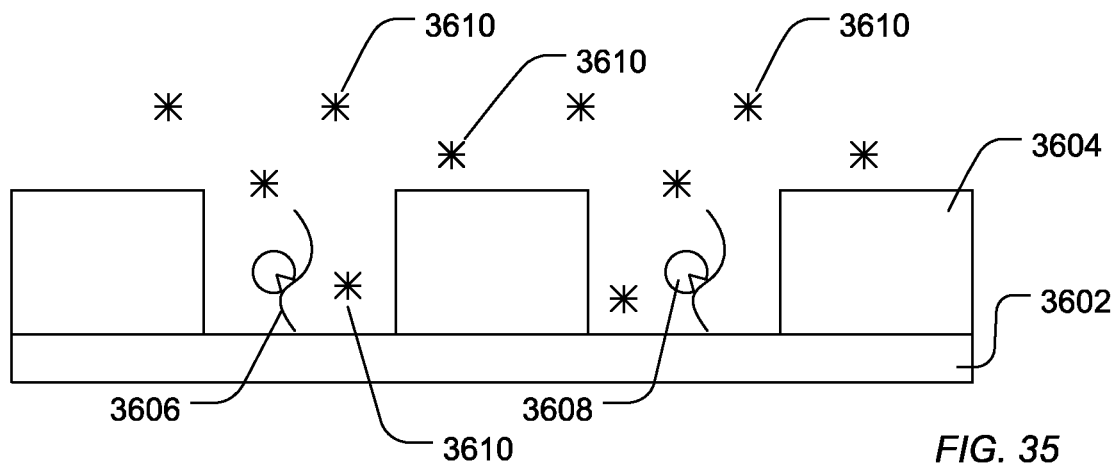
FIG. 35, FIG. 36, and FIG. 37 include illustrations of exemplary systems for fluorescent detection of nucleotide incorporation.

Depending on the nature the system, the template polynucleotide can be linked (e.g., covalently or non-covalently) to the surface. Alternatively, an enzyme (e.g., a polymerase or other template-binding enzyme) can be tethered to the surface and can capture polynucleotides. In FRET-based systems, the enzyme can be associated with a donor particle. For example, as illustrated in FIG. 35, the template polynucleotide 3606 can be attached to a surface 3602 within wells defined by a well structure 3604. A polymerase enzyme 3608 can access the template polynucleotide 3606 and incorporate fluorescent dye modified nucleotides 3610 into a nascent nucleic acid molecule (e.g., an extending primer) in a template-dependent fashion. In another example illustrated in FIG. 36, the enzyme 3708 can be attached to a donor particle or molecule 3710. When incorporating a dye modified nucleotide 3712 complementary to a corresponding nucleotide within the template polynucleotide 3706, the donor particle or molecule can provide energy to the dye of the dye modified nucleotide 3712 causing fluorescence.

Figure 37:
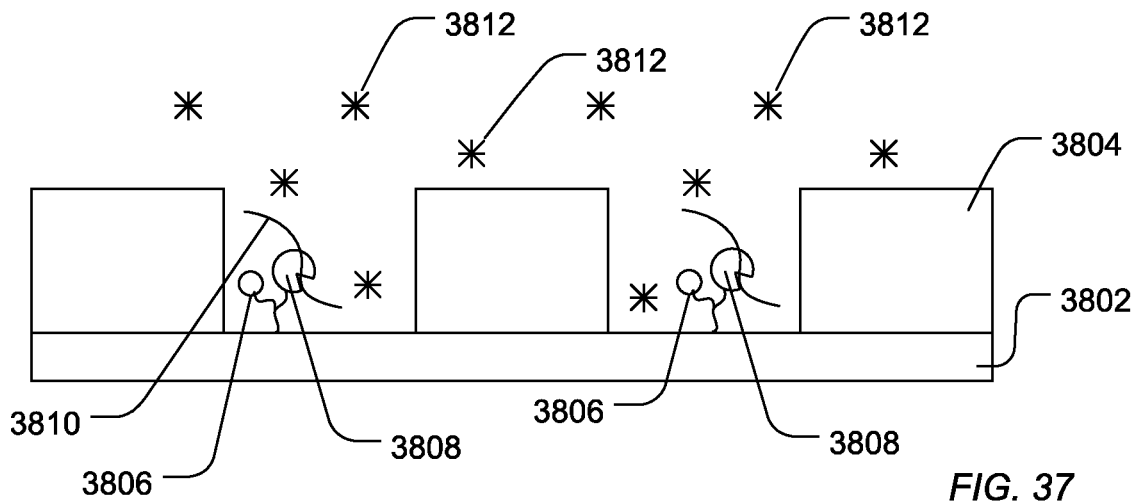

In a further example illustrated in FIG. 37, an enzyme 3808 and associated donor particle or molecule 3806 can be tethered to a surface 3802 within a well defined within the structure 3804. Target polynucleotides 3810 can be bound by the enzyme 3808, and can serve as templates for incorporation of dye modified nucleotides 3812 by the enzyme 3808. When incorporated, the dye of the dye modified nucleotide 3812 can fluoresce, providing an indication of the incorporation.

Surface binding of the template polynucleotide or of the enzyme can be facilitated using a molecular recognition layer bound to the surface. The surfaces to which the molecular recognition layer is bound can be treated with a layer of chemicals prior to attaching probes to enhance the binding or to inhibit non-specific binding during use. For example, glass surfaces can be coated with self-assembled monolayer (SAM) coatings, such as coatings of as aminoalkyl silanes, or of polymeric materials, such as acrylamide and proteins.

Probes can be attached covalently. A number of different chemical surface modifiers can be added to the surface to attach the probes. Examples of chemical surface modifiers include N-hydroxy succinimide (NHS) groups, amines, aldehydes, epoxides, carboxyl groups, hydroxyl groups, hydrazides, hydrophobic groups, membranes, maleimides, biotin, streptavidin, thiol groups, nickel chelates, photoreactive groups, boron groups, thioesters, cysteines, disulfide groups, alkyl and acyl halide groups, glutathiones, maltoses, azides, phosphates, and phosphines.

In some embodiments, surfaces that are reactive to probes comprising amines are used. Examples of such surfaces include NHS-esters, aldehyde, epoxide, acyl halide, and thio-ester. Most proteins, peptides, glycopeptides, etc. have free amine groups, which react with such surfaces to link them covalently to these surfaces. Nucleic acid probes with internal or terminal amine groups can also be synthesized. Thus, nucleic acids can be bound (e.g., covalently or non-covalently) to surfaces using similar chemistries.

The surfaces to which the probes are bound need not be reactive towards amines, but can be easily converted into amine-reactive surfaces with coatings. Examples of coatings include amine coatings (which can be reacted with bis-NHS cross-linkers and other reagents), thiol coatings (which can be reacted with maleimide-NHS cross-linkers, etc.), gold coatings (which can be reacted with NHS-thiol cross linkers, etc.), streptavidin coatings (which can be reacted with bis-NHS cross-linkers, maleimide-NHS cross-linkers, biotin-NHS cross-linkers, etc.), and BSA coatings (which can be reacted with bis-NHS cross-linkers, maleimide-NHS cross-linkers, etc.). Alternatively, the probes, rather than the open surface, can be reacted with specific chemical modifiers to make them reactive to the respective surfaces.

A number of other multi-functional cross-linking agents can be used to convert the chemical reactivity of one kind of surface to another. These groups can be bifunctional, trifunctional, tetra-functional, and so on. They can also be homo-functional or hetero-functional. An example of a bi-functional cross-linker is X-Y-Z, where X and Z are two reactive groups, and Y is a connecting linker. Further, if X and Z are the same group, such as NHS-esters, the resulting cross-linker, NHS—Y—NHS, is a homo-bi-functional cross-linker and would connect an amine surface with an amine-group containing molecule. If X is NHS-ester and Z is a maleimide group, the resulting cross-linker, NHS—Y-maleimide, is a hetero-bi-functional cross-linker and would link an amine surface (or a thiol surface) with a thio-group (or amino-group) containing probe. Cross-linkers with a number of different functional groups are widely available. Examples of such functional groups include NHS-esters, thio-esters, alkyl halides, acyl halides (e.g., iodoacetamide), thiols, amines, cysteines, histidines, di-sulfides, maleimide, cis-diols, boronic acid, hydroxamic acid, azides, hydrazines, phosphines, photoreactive groups (e.g., anthraquinone, benzophenone), acrylamide (e.g., acrydite), affinity groups (e.g., biotin, streptavidin, maltose, maltose binding protein, glutathione, glutathione-S-transferase), aldehydes, ketones, carboxylic acids, phosphates, hydrophobic groups (e.g., phenyl, cholesterol), etc. Such cross-linkers can be reacted with the surface or with the probes or with both, in order to conjugate a probe to a surface. Other alternatives include thiol reactive surfaces such as acrydite, maleimide, acyl halide and thio-ester surfaces.

Such surfaces can covalently link proteins, peptides, glycopeptides, etc., via a (usually present) thiol group. Nucleic acid probes containing pendant thiol-groups can also be easily synthesized.

Alternatively, one can modify surfaces with molecules such as polyethylene glycol (PEG), e.g. PEGs of mixed lengths. Other surface modification alternatives (such as photo-crosslinkable surfaces and thermally cross-linkable surfaces) can be used.

Figure 36:
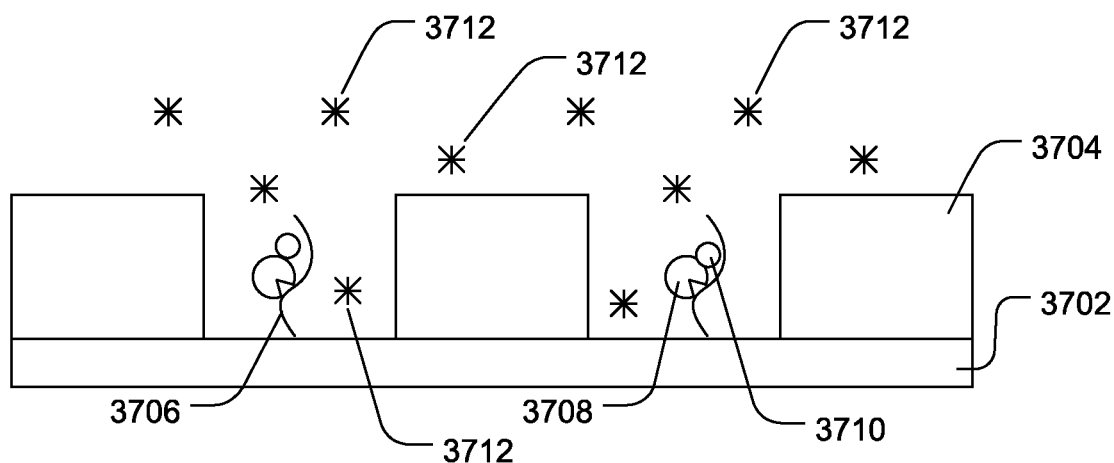

The examples of FIG. 35, FIG. 36, or FIG. 37 illustrate molecules secured to a surface within a well. Alternatively, one or more copies of the target polynucleotide can be secured to a bead or particle. The bead or particle including the target polynucleotide can be disposed over a pixel. In a particular example, synchronous sequencing can be performed using one nucleotide at a time. In such an example, alternative dyes, such as solvatochromatic dyes or dyes sensitive to pH, can be used to provide an optical signal indicating incorporation of a type of nucleotide. The bead or particle may or may not be placed within a well.

In another example, beads or particles can be used to deposit capture molecules at locations, limiting depositions over a pixel by size exclusion based on the size of the bead. Such limited deposition can be used with the device of FIG. 34, for example.

In another example, the length of a signal indicative of a nucleotide that is next in the sequence can be extended by capturing the nucleotide and causing it to emit the signal while preventing incorporation of the nucleotide. In an example, an inhibiting agent can prevent incorporation of the modified nucleotide. An exemplary inhibiting agent includes divalent metal ions, such as calcium, scandium, titanium, vanadium, chromium, iron, cobalt, nickel, copper, zinc, gallium, germanium, arsenic, and selenium ions. In another example, functionality on the nucleotide can prevent incorporation of the modified nucleotide.

In either case, the enzyme can capture the next complementary nucleotide. Modified functionality of the nucleotide can emit a signal, such as a fluorescent signal. As a result of inhibiting the incorporation of the modified nucleotide, the length of the signal can be extended. Subsequently, a complementary nucleotide can be incorporated along the sequence. For example, the inhibiting agent can be washed away, permitting incorporation of the modified nucleotide. In another example, a complementary nucleotide modified with functionality to prevent incorporation can be washed away and replaced with a similar modified nucleotide having functionality that permits incorporation.

In an example, modified nucleotides can be provided sequentially. In another example, the modified nucleotides can be provided in groups of two, three, or four types of nucleotides. For example, when nucleotides are supplied separately and sequentially, the functionalities modifying the nucleotides can provide a similar signal, such as a similar wavelength of emission. Such signals, when the modified nucleotides are incorporated, are separated by time allowing identification of the nucleotide.

Figure 38:
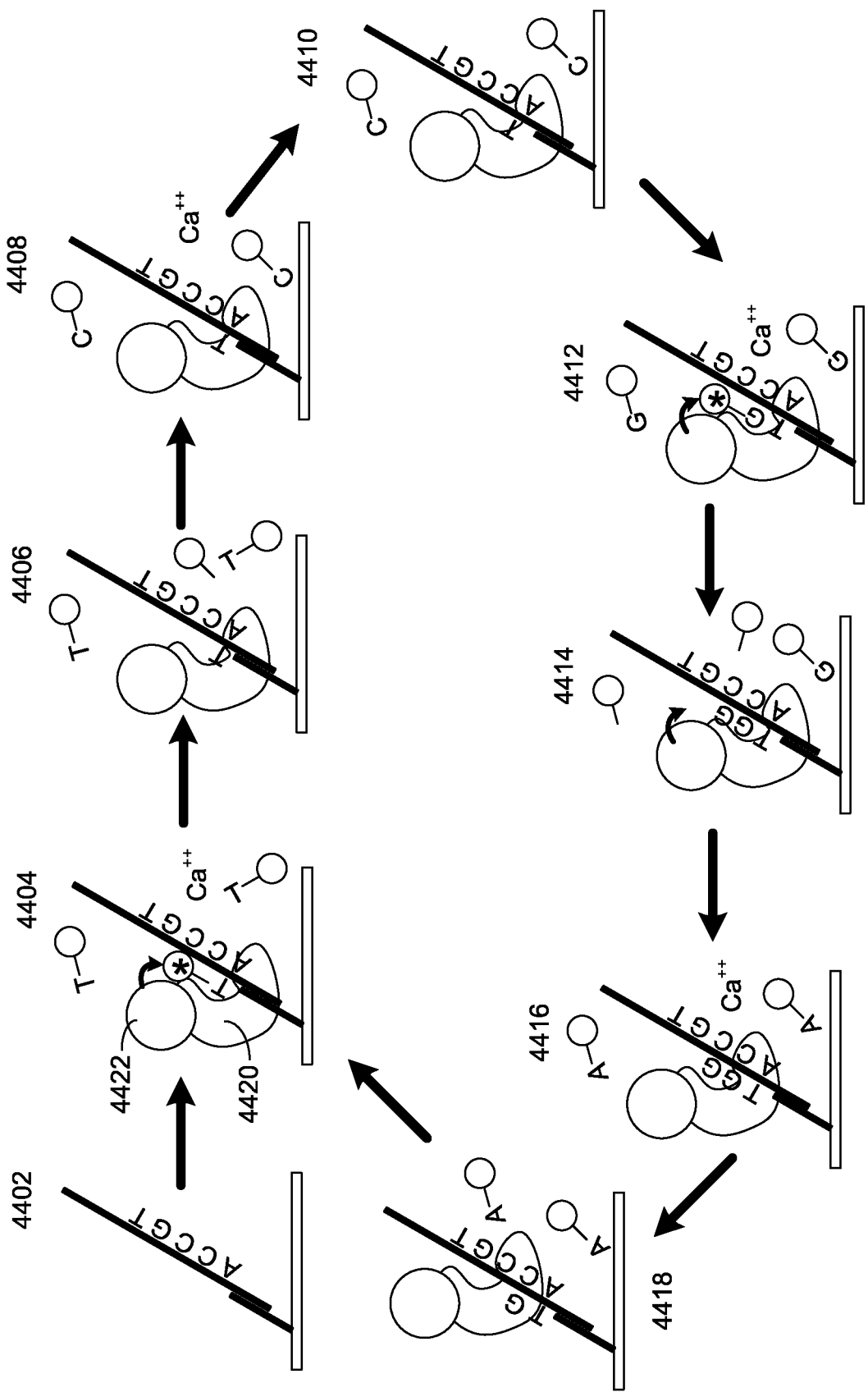
FIG. 38, FIG. 39, and FIG. 40 include illustrations of sequencing schemes.

For example, as illustrated in FIG. 38, a target polynucleotide can be captured over a sequence detecting device, as illustrated at 4402. As illustrated at 4404, a type of nucleotide can be provided along with an inhibiting agent, such as calcium ions. The complementary nucleotide (e.g., T) is captured by the enzyme 4420 and caused to fluoresce in an exemplary FRET-based system 4422. When the inhibiting agent is washed from solution as illustrated at 4406, the T nucleotide is permitted to incorporate, cleaving the emitting functional group. Other types of modified nucleotides can be fed to solution along with inhibiting agent, as illustrated at 4408. When the inhibiting agent is washed solution, as illustrated at 4410, the other non-complementary types of nucleotides fail to emit a signal or be incorporated. Subsequently, as illustrated in 4412, a complementary modified nucleotide is captured by the enzyme in the presence of an inhibiting agent and emits a signal. Even when the sequence includes an adjacent nucleotide of the same type, a single modified nucleotide is captured. As illustrated at 4414, when the inhibiting agent is removed, the complementary modified nucleotide can be incorporated. When in the presence of a homopolymer or adjacent nucleotides of the same type, the modified nucleotide can be incorporated more than once, emitting more than one signal or a signal having greater amplitude. As illustrated at 4416 and 4418, subsequent modified nucleotides can be provided that are not complementary to the target sequence. Such non-complementary modified nucleotides do not fluoresce and are not incorporated even in the absence of the inhibiting agent. As a result of delayed incorporation, the signal length is longer and provides for improved detection.

Alternatively, each type of nucleotide (e.g., A, T, C, or G) can be modified to emit a different signal, such as a signal of a different wavelength. For example, when two types of modified nucleotides flow together through a flow cell, each of the two types of modified nucleotides can be modified with a functionality that emits a different wavelength from the other type of modified nucleotide. As such, the nucleotide being incorporated can be identified based on the different wavelength of emissions, for example. In an example, when a modified A-type nucleotide is provided simultaneously with a modified T-type nucleotide, the modified A-type nucleotide can be modified to provide a distinctly different wavelength from the modified T-type nucleotide. Similarly, when C and G-type modified nucleotides are supplied together, each type of modified nucleotide can include functionality that emits at a different wavelength from the other type of nucleotide.

In a further example, four types of modified nucleotide can be provided in solution simultaneously. In such an example, each of the modified types of modified nucleotides can emit different signals, such as that at different wavelengths. Alternatively, one type of nucleotide (i.e., a dark nucleotide) of the four may not be modified to emit a signal. In such an example, the inhibiting agent can be intermittently fed to the flow volume to inhibit incorporation and increase the signal length of the nucleotide to be incorporated. When the inhibiting agent is removed from the chamber, incorporation can proceed. In another example, one incorporatable modified nucleotide can be fed to the flow volume simultaneously with three other unincorporatable modified nucleotides. Solutions including a select incorporatable modified nucleotide (e.g., A, T, C or G) can be fed simultaneously to the flow volume with three other unincorporatable types of modified nucleotides. Such solutions can be fed sequentially or one after the other.

Figure 39:
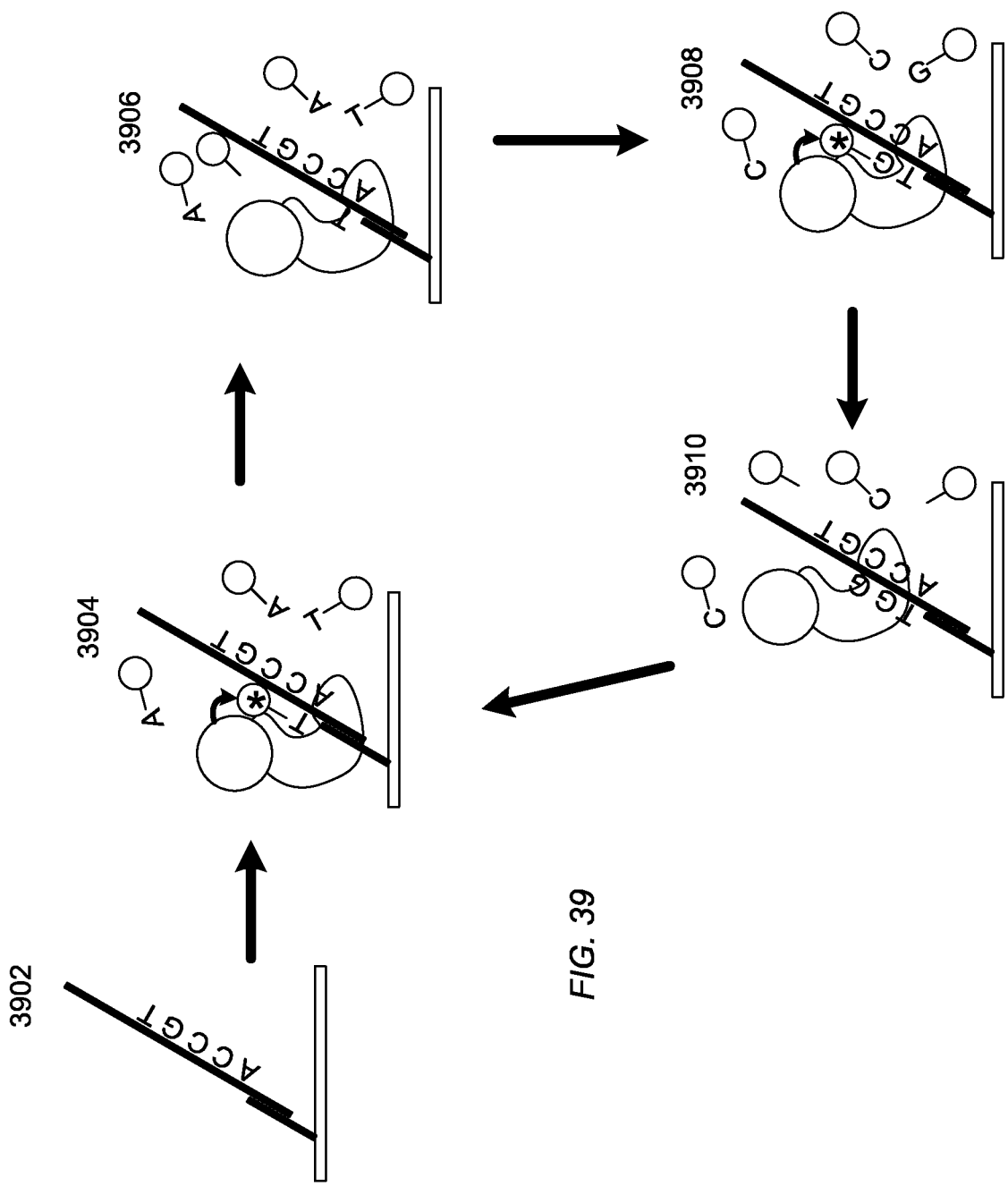

In another example illustrated in FIG. 39, a target polynucleotide or template is captured, as illustrated at 3902. Modified nucleotides may be provided in pairs. Each modified nucleotide of the pair emits a different signal, such as at different wavelengths. As such, incorporation of one type of modified nucleotide relative to the other type of nucleotide can be identified based on the emitted signal. As illustrated at 3904, the complementary nucleotide (e.g., T) is captured and caused to fluoresce. The capture can be performed in the presence of an inhibiting agent. Subsequently, the complementary nucleotide (e.g., T) is incorporated (e.g., upon removal of the inhibiting agent), while another type of modified nucleotide (e.g., A) is not captured and does not fluorescence, as illustrated at 3906. As illustrated at 3908, two other types of modified nucleotides can be provided, such as, for example, C-type and G-type modified nucleotides. The complementary modified nucleotide (e.g., G) can be captured and caused to fluoresce, followed by incorporation, as illustrated at 3910. Capturing can be performed in the presence of an inhibiting agent. In the presence of a homopolymer section or a section including adjacent nucleotides of the same type, the complementary modified nucleotide is incorporated more than once, providing more than one signal or a higher amplitude signal and leaving the non-complementary nucleotide in solution without fluorescing or being incorporated. For example, incorporation along a homopolymer section can provide a scaled brightness indicative of the number of repeats within the homopolymer section. In such an example, the polymerase captures the correct base, causing extended signal emission when in the presence of an inhibiting agent. Alternatively, the method can be performed in the presence of four types of modified nucleotides, each emitting a distinct signal.

Figure 40:
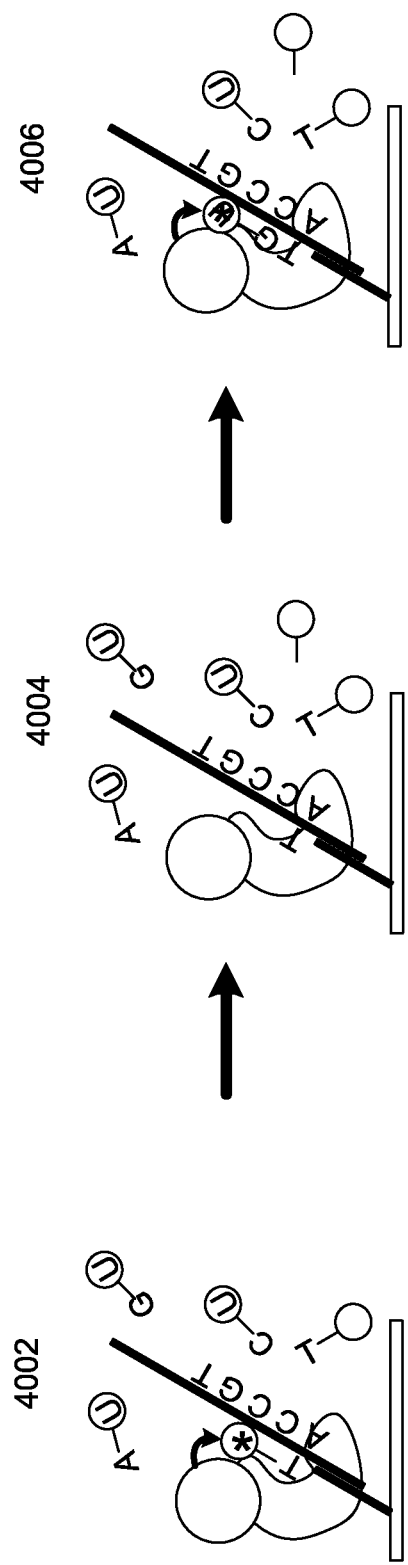
Figure 41:
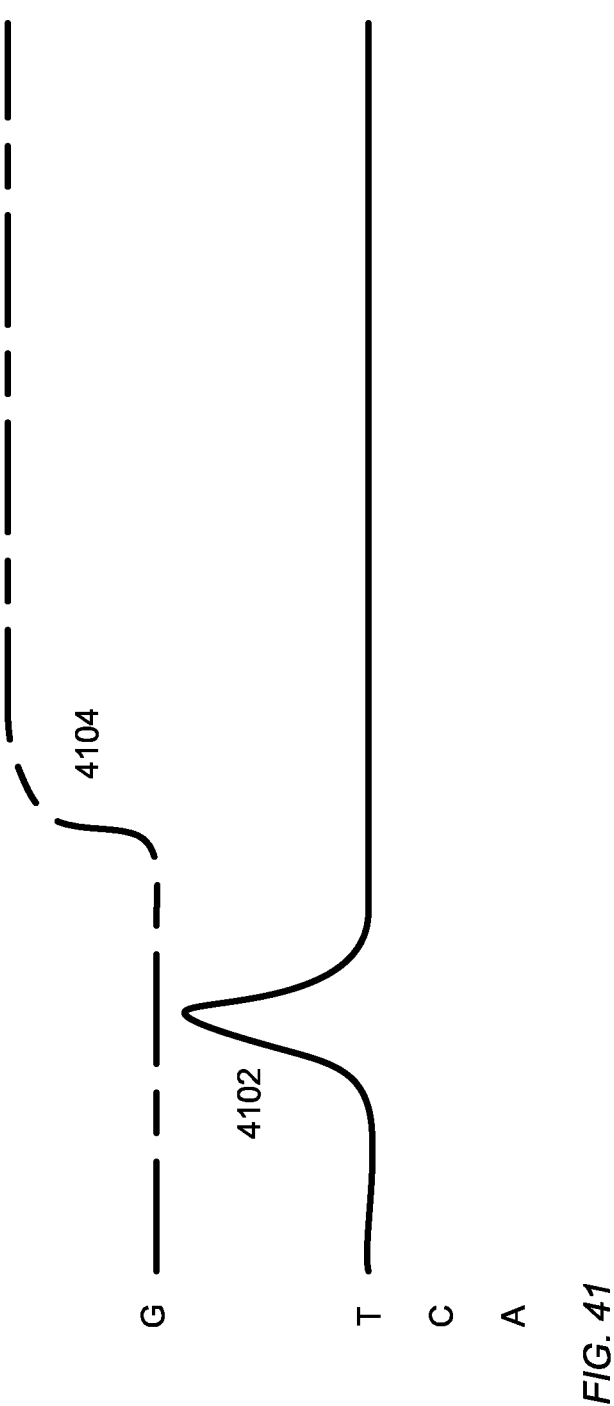
FIG. 41 includes a graph illustration of an exemplary signal response during sequencing.

In a further example illustrated in FIG. 40, a mixture of modified nucleotides can be provided simultaneously in which one of the types of nucleotide is able to be incorporated while the remaining types of nucleotides are modified to prevent incorporation. As such, complementary incorporatable nucleotides can be incorporated, while subsequent complementary unincorporatable nucleotides can temporarily emit a signal, providing a preliminary indication as to which modified nucleotide is complementary to the adjacent nucleotide in the sequence. As illustrated at 4002, for example, the complementary T-type nucleotide can be captured and fluoresce. Optionally, such capture can be performed in the presence of an inhibiting agent. As illustrated at 4004, the complementary nucleotide is incorporated releasing the modified florescent functionality. The next complementary nucleotide can be captured by the enzyme and caused to fluoresce. But, such a next complementary nucleotide can be modified to prevent incorporation. As such, the unincorporatable modified nucleotide (e.g., G) emits a signal indicative of which nucleotide is complementary to the next position in the sequence, but is not incorporated. FIG. 41 illustrates an exemplary signals resulting from the incorporation of a nucleotide and the capture of an unincorporated nucleotide. For example, the first captured incorporatable nucleotide (e.g., T) emits a short signal, as illustrated at 4102. A subsequently captured unincorporatable modified nucleotide (e.g., G) emits a long signal 4104 indicative of its being complementary to the sequence, yet is unable to be incorporated. As the solutions are washed through the system, such an unincorporated nucleotide provides preliminary indication as to which nucleotide is next in the sequence, which is confirmed when a subsequent solution including an incorporatable modified nucleotide of the same type is fed to the system and emits a signal. Alternatively, more than one incorporatable modified nucleotide can be included in a solution with one or more unincorporatable modified nucleotides.

Modified nucleotides can be labeled or modified to provide the ability to provide a signal in response to incorporation and optionally, to adjust whether the nucleotide or analog thereof can be incorporated.

In one embodiment, the labeled nucleotide can include 3-10 or more phosphate groups. In an example, the labeled nucleotide can be adenosine, guanosine, cytidine, thymidine or uridine, or any other type of labeled nucleotide. In another example, the label can be an energy transfer acceptor reporter moiety. In particular, the label can be a fluorescent dye. The polymerase can be contacted with more than one type of labeled nucleotide (e.g., A, G, C, or T/U, or others). Each type of labeled nucleotide can be operably linked to a different reporter moiety to permit nucleotide identity. Each type of labeled nucleotide can be operably linked to one type of reporter moiety. In an example, the labeled nucleotides are operably linked at the terminal phosphate group with a reporter moiety. In another example, the labeled nucleotides are operably linked at the base moiety with a reporter moiety. In another embodiment, the labeled nucleotide can be a non-incorporatable nucleotide. The non-incorporatable nucleotide can bind to the polymerase and template nucleic acid molecule which is base-paired to a polymerization initiation site, in a template-dependent manner, but does not incorporate. Different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Typically, for direct excitation of the reporter moiety, the length of the transient binding time of a complementary nucleotide can be longer or more frequent compared to that of a non-complementary nucleotide. Typically, for FRET-based excitation and detection of the reporter moieties, the transient binding time of a complementary nucleotide can be of longer duration compared to that of a non-complementary nucleotide.

In one embodiment, the polymerase can be operably linked to an energy transfer donor (e.g., fluorescent dye or nanoparticle). In an example, the labeled nucleotide comprises an energy transfer acceptor moiety (e.g., fluorescent dye). For example, the energy transfer donor and acceptor can be a FRET pair. The signal (or change in the signal) from the energy transfer donor or acceptor can be used to detect the presence of the transiently-bound nucleotide. In a particular example, the signal emitted by the transiently-bound nucleotide can be a FRET signal.

In one embodiment, the excitation source can be electromagnetic radiation. The excitation source can be a laser. The signal, or the change in the signal, can be optically detectable. In an example, the polymerase has an active site. The active site can be enzymatically-active. The labeled nucleotide can bind the active site, thereby bringing the polymerase and labeled nucleotide in close proximity with each other. The polymerase may be labeled or unlabeled. In one embodiment, the signal or change in the signal can be a fluorescent signal resulting from direct excitation of the label which is operably linked to the transiently-bound labeled nucleotide or to the labeled polymerase. In one embodiment, the energy transfer donor or acceptor moieties can fluoresce in response to direct excitation. These fluorescence responses can be a signal or change in a signal. In an example, the energy transfer acceptor moiety can fluoresce in response to energy transferred from a proximal excited energy transfer donor moiety. These fluorescence responses can be a signal or change in a signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. The energy transfer signal generated by proximity of the donor moiety to the acceptor moiety can remain unchanged. In another example, the energy transfer signal generated by proximity of the donor moiety to the acceptor moiety results in changes in the energy transfer signal. The changes in the signal or the energy transfer signal from the donor or acceptor moiety can include changes in the: intensity of the signal; duration of the signal; wavelength of the signal; amplitude of the signal; polarization state of the signal; duration between the signals; or rate of the change in intensity, duration, wavelength or amplitude. The change in the signal or the energy transfer signal can include a change in the ratio of the change of the energy transfer donor signal relative to change of the energy transfer acceptor signals. The signal or the energy transfer signal from the donor can increase or decrease. In another example, the signal or the energy transfer signal from the acceptor can increase or decrease. The signal or the energy transfer signal associated with nucleotide transient-binding can include: a decrease in the donor signal when the donor is proximal to the acceptor; an increase in the acceptor signal when the acceptor is proximal to the donor; an increase in the donor signal when the distance between the donor and acceptor increases; or a decrease in the acceptor signal when the distance between the donor and acceptor increases.

In an example, unincorporatable or non-incorporatable nucleotides or analogs thereof may or may not have a structure similar to that of a native nucleotide which may include base, sugar, and phosphate moieties.

The non-incorporatable nucleotides can bind the polymerase/template complex in a template-dependent manner, or can act as a universal mimetic and bind the polymerase/template complex in a non-template-dependent manner. The non-incorporatable nucleotides can be a nucleotide mimetic of incorporatable nucleotides, such as adenosine, guanosine, cytidine, thymidine or uridine nucleotides. The non-incorporatable nucleotide includes any compound having a nucleotide structure, or a portion thereof, which can bind a polymerase.

For example, the non-incorporatable nucleotides can have the general structure:

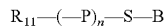

Where B can be a base moiety, such as a hetero cyclic base which includes substituted or unsubstituted nitrogen-containing heteroaromatic ring. Where S can be a sugar moiety, such as a ribosyl, riboxyl, or glucosyl group. Where n can be 1-10, or more. Where P can be one or more substituted or unsubstituted phosphate or phosphonate groups. Where R11, if included, can be a reporter moiety (e.g., a fluorescent dye). In one embodiment, the non-incorporatable nucleotide having multiple phosphate or phosphonate groups, the linkage between the phosphate or phosphonate groups can be non-hydrolyzable by the polymerase. The non-hydrolyzable linkages include, but are not limited to, amino, alkyl, methyl, and thio groups. Non-incorporatable nucleotide tetraphosphate analogs can have alpha-thio or alpha boreno substitutions.

The phosphate or phosphonate portion of the non-incorporatable nucleotide can have the general structure:

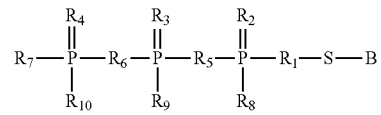

where B can be a base moiety and S can be a sugar moiety. Where any one of the R1-R7 groups can render the nucleotide non-hydrolyzable by a polymerase. Where the sugar C5 position can be CH2, CH2O, CH═, CHR, or CH2. Where the R1 group can be O, S, CH═, CH(CN), or NH. Where the R2, R3, and R4, groups can independently be O, BH3, or SH. Where the R5 and R6 groups can independently be an amino, alkyl, methyl, thio group, or CHF, CF2, CHBr, CCl2, O—O, or —C≡C—. Where the R7 group can be oxygen, or one or more additional phosphate or phosphonate groups, or can be a reporter moiety. Where R8 can be SH, BH3, CH3, NH2, or a phenyl group or phenyl ring. Where R9 can be SH. Where R10 can be CH3, N3CH2CH2, NH2, ANS, N3, MeO, SH, Ph, F, PhNH, PhO, or RS (where Ph can be a phenyl group or phenyl ring, and F can be a fluorine atom or group). The substituted groups can be in the S or R configuration.

The non-incorporatable nucleotides can be alpha-phosphate modified nucleotides, alpha-beta nucleotide analogs, beta-phosphate modified nucleotides, beta-gamma nucleotide analogs, gamma-phosphate modified nucleotides, caged nucleotides, or di-nucleotide analogs.

In one aspect, nucleotides are compounds that can bind selectively to, or can be polymerized by, a polymerase. Typically, but not necessarily, the polymerase selectively binds the nucleotide and catalyzes polymerization of the nucleotide onto a nucleic acid strand (e.g., nucleotide incorporation). Such nucleotides include not only naturally-occurring nucleotides but also any analogs, regardless of their structure, that can bind selectively to, or can be polymerized by, a polymerase. While naturally-occurring nucleotides typically comprise base, sugar and phosphate moieties, the nucleotides of the present disclosure can include compounds lacking any one, some or all of such moieties.

The nucleotides can be operably linked to a reporter moiety (e.g., labeled nucleotides) or can be un-labeled nucleotides. The nucleotides also include non-incorporatable nucleotides, and terminator nucleotides (e.g., chain terminating nucleotides and reversible terminator nucleotides). The nucleotides can be nucleotide polyphosphate molecules. Examples of nucleotide polyphosphate molecules and nucleoside polyphosphate molecules include ribonucleotides, deoxyribonucleotides, ribonucleotide polyphosphate molecules, deoxyribonucleotide polyphosphate molecules, peptide nucleotides, nucleoside polyphosphate molecules, metallonucleosides, phosphonate nucleosides, and modified phosphate-sugar backbone nucleotides, and any analogs or variants of the foregoing.

The nucleotides typically comprise a chain of phosphorus atoms comprising three, four, five, six, seven, eight, nine, ten or more phosphorus atoms. In some embodiments, the phosphorus chain can be attached to any carbon of a sugar ring, such as the 2, 3, or 5' carbon. The phosphorus chain can be linked to the sugar with an intervening O or S. One or more phosphorus atoms in the chain can be part of a phosphate group having P and O. In another example, the phosphorus atoms in the chain can be linked together with intervening O, NH, S, methylene, substituted methylene, ethylene, substituted ethylene, CNH2, C(O), C(CH2), CH2CH2, or C(OH)CH2R (where R can be a 4-pyridine or 1-imidazole). In one embodiment, the phosphorus atoms in the chain can have side groups having O, BH3, or S. In the phosphorus chain, a phosphorus atom with a side group other than O can be a substituted phosphate group. The phosphate groups include analogs, such as phosphoramidate, phosphorothioate, phosphorodithioate, and O-methyl-phosphoroamidite groups. At least one of the phosphate groups can be substituted with a fluoro or chloro group. The phosphate groups can be linked to the sugar moiety by an ester or phosphoramide linkage.

The nucleotides typically comprise a hetero cyclic base which includes substituted or unsubstituted nitrogen-containing parent heteroaromatic ring which is commonly found in nucleic acids, including naturally-occurring, substituted, modified, or engineered variants, or analogs of the same. The base is capable of forming Watson-Crick or Hoogstein hydrogen bonds with an appropriate complementary base. Exemplary bases include, but are not limited to, purines and pyrimidines such as: 2-aminopurine, 2,6-diaminopurine, adenine (A), ethenoadenine, N6-2-isopentenyladenine (6iA), N6-2-isopentenyl-2-methylthioadenine (2ms6iA), N6-methyladenine, guanine (G), isoguanine, N2-dimethyl-guanine (dmG), 7-methylguanine (7mG), 2-thiopyrimidine, 6-thioguanine (6sG), hypoxanthine and O6-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thio-thymine (4sT), 5,6-dihydrothymine, O4-methylthymine, uracil (U), 4-thiouracil (4sU) and 5,6-dihydrouracil (dihy-drouracil; D); indoles such as nitroindole and 4-methylin-dole; pyrroles such as nitropyrrole; nebularine; inosines; hydroxymethylcytosines; 5-methycytosines; base (Y); as well as methylated, glycosylated, and acylated base moieties; and the like.

The nucleotides typically comprise a suitable sugar moiety, such as carbocyclic moiety, acyclic moieties, and other suitable sugar moieties. The sugar moiety may be selected from the following: ribosyl, 2'-deoxyribosyl, 3'-deoxyribosyl, 2',3'-dideoxyribosyl, 2',3'-didehydrodideoxyribosyl, 2'-alkoxyribosyl, 2'-azidoribosyl, 2'-aminoribosyl, 2'-fluo-roribosyl, 2'-mercaptoriboxyl, 2'-alkylthioribosyl, 3'-alkoxy-ribosyl, 3'-azidoribosyl, 3'-aminoribosyl, 3'-fluororibosyl, 3'-mercaptoriboxyl, 3'-alkylthioribosyl carbocyclic, acyclic and other modified sugars.

Provided herein are labeled nucleotides which can bind in a template-dependent manner, to a nucleic acid-dependent polymerase. In practicing the methods provided herein, the incorporation of the labeled nucleotides can be inhibited by any reaction condition which permits transient binding of a nucleotide (e.g., complementary or non-complementary) to a polymerase, and inhibits nucleotide incorporation, including: (1) reaction conditions and reagents (e.g., temperature, pH, ionic strength, divalent cations, or time); (2) modified polymerases; (3) modifications of the nucleotide which inhibit incorporation; or (4) non-extendible polymerization initiation site.

The labeled nucleotide can bind the polymerase, which is bound to a base-paired template nucleic acid molecule and polymerization initiation site. The polymerase can interrogate the labeled nucleotide for complementarity with the template nucleotide on the template molecule. The transient-binding time of the complementary labeled nucleotide can be longer compared to the transient-binding time of the non-complementary labeled nucleotide.

The labeled nucleotides comprise a nucleotide operably linked to at least one reporter moiety at any position of the base or sugar, or any of the phosphate groups (alpha, beta, gamma, any phosphate group distal to the sugar moiety, or a terminal phosphate group).

The labeled nucleotide can be a non-incorporatable nucleotide or a terminator nucleotide which is operably linked to at least one reporter moiety. The reporter moiety can be a fluorescent dye, energy transfer dye, or any other type of reporter moiety. The labeled nucleotide can be operably linked to different types of reporter moieties. The same type or different types of reporter moieties can be operably linked to different types of nucleotides, for example, to permit base distinction or identification. A linear or branched linker can be used to attach the nucleotide to the reporter moiety. An intervening linker can connect different reporter moieties to each other or to the nucleotide in any combination of linking arrangements. The labeled nucleotide can be incorporated by a naturally occurring, modified, or engineered nucleic acid-dependent polymerase. The labeled nucleotide can be resistant to degradation by 3'-5' exonuclease activity of the polymerase.

Useful linking schemes include attaching reporter moieties to oligonucleotides synthesized using phosphoramidate to incorporate amino-modified dT. In one embodiment, the reporter moiety (e.g., fluorophore) can be linked to the base of the nucleotide via a hexylacrylamide linker. In another embodiment, the reporter moiety (e.g., fluorophore) can be linked to the C5 position of the base (e.g., cytosine or uracil) via a hexylacrylamide linker (Molecular Probes, A32763 and A32771), or can be linked to the C5 position of the base (e.g., uracil) via a propargylamino linker. In yet another embodiment, the reporter moiety (fluorophore) can be linked to the N7 position of the base (e.g., guanosine) via a propargylamino linker.

Provided herein are one or more reporter moieties which are operably linked to the labeled nucleotides, terminator nucleotides, non-incorporatable nucleotides, nanoparticles, polymerases, template nucleic acid molecules, primer molecules, surfaces, or oligonucleotides.

The reporter moiety generates, or causes to generate, a detectable signal. Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. The reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other.

The reporter moieties may be selected so that each absorbs excitation radiation or emits fluorescence at a wavelength distinguishable from the other reporter moieties to permit monitoring the presence of different reporter moieties in the same reaction. Two or more different reporter moieties can be selected having spectrally distinct emission profiles, or having minimal overlapping spectral emission profiles.

In one aspect, the signals from the different reporter moieties do not significantly overlap or interfere, by quenching, colorimetric interference, or spectral interference.

The chromophore moiety may be 5-bromo-4-chloro-3-indolyl phosphate, 3-indoxyl phosphate, p-nitrophenyl phosphate, and derivatives thereof, or lactamase or peroxidase based chemistry.

The chemiluminescent moiety may be a phosphatase-activated 1,2-dioxetane compound. The 1,2-dioxetane compound includes disodium 2-chloro-5-(4-methoxyspiro[1,2-dioxetane-3,2'-(5-chloro-)tricyclo[3,3,1-13,7]-decan]-1-yl)-1-phenyl phosphate (e.g., CDP-STAR), chloroadamant-2'-ylidenemethoxyphenoxy phosphorylated dioxetane (e.g., CSPD), and 3-(2'-spiroadamantane)-4-methoxy-4-(3''-phosphoryloxy)phenyl-1,2-dioxetane (e.g., AMPPD).

The fluorescent moiety includes: rhodols; resorufins; coumarins; xanthenes; acridines; fluoresceins; rhodamines; erythrins; cyanins; phthalaldehydes; naphthylamines; fluorescamines; benzoxadiazoles; stilbenes; pyrenes; indoles; borapolyazaindacenes; quinazolinones; eosin; erythrosin; Malachite green; CY dyes (GE Biosciences), including Cy3 (and its derivatives) and Cy5 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (boron-dipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610 (N-succinimidyl ester), ATTO 635 (NHS ester); ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1,3-dichloro-9,9-dimethylacridin-2-one or any derivatives thereof) (Molecular Probes); QUASAR dyes (Biosearch); IRDYES dyes (LiCor) including IRDYE 700DX (NHS ester), IRDYE 800RS (NHS ester) and IRDYE 800CW (NHS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED (phosphoramidate), EPOCH YAKIMA YELLOW (phosphoramidate), EPOCH GIG HARBOR GREEN (phosphoramidate); Tokyo green; and CF dyes including CF 647 and CF555 (Biotium).

Quencher dyes may include: ATTO 540Q, ATTO 580Q, and ATTO 612Q (Atto-Tec); QSY dyes including QSY 7, QSY 9, QSY 21, and QSY 35 (Molecular Probes); and EPOCH ECLIPSE QUENCHER (phosphoramidate) (Glen Research). The fluorescent moiety can be a 7-hydroxycoumarin-hemicyanine hybrid molecule which is a far-red emitting dye.

The fluorescent moiety may be a fluorescence-emitting metal such as a lanthanide complex, including those of Europium and Terbium.

Provided herein are reporter moieties which can be energy transfer moieties, such as energy transfer pairs (e.g., donors and acceptors), which are operably linked to the labeled nucleotides, terminator nucleotides, non-incorporatable nucleotides, nanoparticles, polymerases, template nucleic acid molecules, primer molecules, surfaces, or oligonucleotides.

In one aspect, the energy transfer moiety can be an energy transfer donor, such as a nanoparticle or an energy transfer dye. In another aspect, the energy transfer moiety can be an energy transfer acceptor, such as an energy acceptor dye.

In one aspect, the energy transfer pair can be operably linked to the same molecule. In another aspect, the donor and acceptor can be operably linked to different molecules in any combination. For example, the donor can be linked to the polymerase, template molecule, or primer molecule, and the acceptor can be linked to the nucleotide (e.g., non-incorporatable nucleotide or terminator nucleotide), the template molecule, or the primer molecule.

The energy transfer donor is capable of absorbing electromagnetic energy (e.g., light) at a first wavelength and emitting excitation energy in response. The energy acceptor is capable of absorbing excitation energy emitted by the donor and fluorescing at a second wavelength in response.

The donor and acceptor moieties can interact with each other physically or optically in a manner which produces a detectable signal when the two moieties are in proximity with each other. A proximity event includes two different moieties (e.g., energy transfer donor and acceptor) approaching each other, or associating with each other, or binding each other.

The donor and acceptor moieties can transfer energy in various modes, including: fluorescence resonance energy transfer (FRET), scintillation proximity assays (SPA), luminescence resonance energy transfer (LRET), direct quenching, chemiluminescence energy transfer (CRET), bioluminescence resonance energy transfer (BRET), and excimer formation.

In one aspect, the energy transfer pair can be FRET donor and acceptor moieties. FRET is a distance-dependent radiationless transmission of excitation energy from a donor moiety to an acceptor moiety. For example, a donor moiety, in an excited state, transfers its energy to a proximal acceptor moiety by non-radiative dipole-dipole interaction or energy transfer not strictly following the Forster's theory, such as nonoverlapping energy transfer occurring when nonoverlapping acceptors are utilized. Typically, the efficiency of FRET energy transmission is dependent on the inverse sixth-power of the separation distance between the donor and acceptor, which is approximately 10-100 Angstroms. FRET is useful for investigating changes in proximity between or within biological molecules. FRET efficiency may depend on donor-acceptor distance r as $1/r6$ or $1/r4$. The distance where FRET efficiency is 50% is termed RO, also known as the Forster distance. RO is unique for each donor-acceptor combination and may be about 5 to 10 nm. The efficiency of FRET energy transfer can sometimes be dependent on energy transfer from a point to a plane which varies by the fourth power of distance separation.

In biological applications, FRET can provide an on-off type signal indicating when the donor and acceptor moieties are within proximity of each other. Additional factors affecting FRET efficiency include the quantum yield of the donor, the extinction coefficient of the acceptor, and the degree of spectral overlap between the donor and acceptor. Procedures are well known for maximizing the FRET signal and detection by selecting high yielding donors and high absorbing acceptors with the greatest possible spectral overlap between the two. The change in fluorescence from a donor (e.g., reduced fluorescence signal) during a FRET event, can be an indication of proximity between a donor and acceptor moiety.

The production of signals from FRET donors and acceptors can be sensitive to the distance between donor and acceptor moieties, the orientation of the donor and acceptor moieties, or a change in the environment of one of the moieties. For example, a nucleotide (e.g., non-incorporatable or terminator nucleotide) linked with a FRET moiety (e.g., acceptor) may produce a detectable signal when it approaches, associates with, or binds a polymerase linked to a FRET moiety (e.g., donor). In another example, a FRET donor and acceptor linked to one protein can emit a FRET signal upon conformational change of the protein. Some FRET donor/acceptor pairs exhibit changes in absorbance or emission in response to changes in their environment, such as changes in pH, ionic strength, ionic type (NO2, Ca+2, Mg+2, Zn+2, Na+, Cl−, K+), oxygen saturation, and solvation polarity.

The FRET donor or acceptor may be a fluorophore, luminophore, chemiluminophore, bioluminophore, or quencher. Accordingly, the FRET donor and acceptors may undergo fluorescence or other types of energy transfer with each other, including luminescence resonance energy transfer, bioluminescence resonance energy transfer, chemiluminescence resonance energy transfer, and similar types of energy transfer not strictly following the Forster's theory, such as the non-overlapping energy transfer when non-overlapping acceptors are utilized.

The energy transfer moiety can be a FRET quencher. Typically, quenchers have an absorption spectrum with large extinction coefficients, however the quantum yield for quenchers is reduced, such that the quencher emits little to no light upon excitation. Quenching can be used to reduce the background fluorescence, thereby enhancing the signal-to-noise ratio. In one aspect, energy transferred from the donor may be absorbed by the quencher which emits moderated (e.g., reduced) fluorescence. In another aspect, the acceptor can be a non-fluorescent chromophore which absorbs the energy transferred from the donor and emits heat (e.g., the energy acceptor is a dark quencher).

For an example, a quencher can be used as an energy acceptor with a nanoparticle donor in a FRET system. One exemplary method involves the use of quenchers in conjunction with reporters comprising fluorescent reporter moieties. In this strategy, certain nucleotides in the reaction mixture are labeled with a reporter comprising a fluorescent label, while the remaining nucleotides are labeled with one or more quenchers. Alternatively, each of the nucleotides in the reaction mixture is labeled with one or more quenchers. Discrimination of the nucleotide bases is based on the wavelength or intensity of light emitted from the FRET acceptor, as well as the intensity of light emitted from the FRET donor. If no signal is detected from the FRET acceptor, a corresponding reduction in light emission from the FRET donor indicates transient-binding of the nucleotide labeled with a quencher. The degree of intensity reduction may be used to distinguish between different quenchers.

Examples of fluorescent donors and non-fluorescent acceptor (e.g., quencher) combinations have been developed for detection of proteolysis and nucleic acid hybridization. FRET donors, acceptors and quenchers can be moieties that absorb electromagnetic energy (e.g., light) at about 300-900 nm, or about 350-800 nm, or about 390-800 nm.

Energy transfer donor and acceptor moieties can be made from materials which typically fall into four general categories, including: (1) organic fluorescent dyes, dark quenchers and polymers (e.g., dendrimers); (2) inorganic material such as metals, metal chelates and semiconductors nanoparticles; (3) biomolecules such as proteins and amino acids (e.g., green fluorescent protein and derivatives thereof); and (4) enzymatically catalyzed bioluminescent molecules. The material for making the energy transfer donor and acceptor moieties can be selected from the same or different categories.

The FRET donor and acceptor moieties which are organic fluorescent dyes, quenchers or polymers include traditional dyes that emit in the UV, visible, or near-infrared region. The UV emitting dyes include coumarin-, pyrene-, and naphthalene-related compounds. The visible and near-infrared dyes include xanthene-, fluorescein-, rhodol-, rhodamine-, and cyanine-related compounds. The fluorescent dyes also includes DDAO ((7-hydroxy-9H-(1,3-dichloro-9,9-dimethylacridin-2-one)), resorufin, ALEXA FLUOR and BODIPY dyes (both Molecular Probes), HILYTE Fluors (AnaSpec), ATTO dyes (Atto-Tec), DY dyes (Dyomics GmbH), TAMRA (Perkin Elmer), tetramethylrhodamine (TMR), TEXAS RED, DYLIGHT (Thermo Fisher Scientific), FAM (AnaSpec), JOE and ROX (both Applied Biosystems), and Tokyo Green.

Additional fluorescent dyes which can be used as quenchers includes: DNP, DABSYL, QSY (Molecular Probes), ATTO (Atto-Tec), BHQ (Biosearch Technologies), QXL (AnaSpec), BBQ (Berry and Associates) and CY5Q/7Q (Amersham Biosciences).

The FRET donor and acceptor moieties which comprise inorganic materials include gold (e.g., quencher), silver, copper, silicon, semiconductor nanoparticles, and fluorescence-emitting metal such as a lanthanide complex, including those of Europium and Terbium.

Suitable FRET donor/acceptor pairs include: FAM as the donor and JOE, TAMRA, and ROX as the acceptor dyes. Other suitable pairs include: CYA as the donor and R6G, TAMRA, and ROX as the donor dyes.

In one embodiment, a nucleotide can be operably linked to a suitable reporter moiety. This labeled nucleotide can bind transiently to the polymerase. The reporter moiety can be excited and the signal emitted by the reporter moiety can be detected.

In another embodiment, a polymerase can be operably linked to a suitable nanoparticle and a nucleotide can be operably linked to a suitable reporter moiety. The labeled nucleotide can bind to the polymerase. The nanoparticle can be excited and the resulting energy from the excited nanoparticle can be transferred to the reporter moiety. The transferred energy can excite the reporter moiety, which can be emitted as a detectable signal.

Provided herein are terminator nucleotides which can be incorporated onto the polymerization initiation site, in a template-dependent manner, by a nucleic acid-dependent polymerase, but the terminator nucleotide (which is incorporated) inhibits the incorporation of the next nucleotide. The terminator nucleotide can be incorporated by a naturally occurring, modified, or engineered nucleic acid-dependent polymerase.

The extending strand comprises the polymerization initiation site and a nucleotide which is incorporated at the terminal 3' end of the initiation site. The extending strand can have an extendible- or non-extendible 3' terminal end. The extendible end includes a terminal 3'-OH group. The non-extendible end is not extendible by a polymerase. The non-extendible end can include any moiety which inhibits incorporation of the next nucleotide. A terminator nucleotide, which is incorporated onto the polymerization initiation site, forms the new non-extendible end of the extending strand.

The terminator nucleotide comprises a nucleotide operably linked to an inhibitor moiety. The inhibitor moiety comprises any chemical compound or chemical group which permits incorporation of the terminator nucleotide by the polymerase but inhibits incorporation of the next nucleotide. Thus, the polymerase can incorporate one and only one terminator nucleotide, thereby advancing nucleotide incorporation by only one base. The inhibitor moiety can be operably linked to any portion of the nucleoside or nucleotide (e.g., any phosphate group, or base or sugar moiety). The same type or different types of inhibitor moieties can be operably linked to different types of nucleotides. The terminator nucleotide can be resistant to degradation by 3'-5' exonuclease activity of the polymerase.

On the terminator nucleotide, the inhibitor moiety can be modified so that the next nucleotide can be incorporated (e.g., reversible terminator nucleotide). Alternatively, the inhibitor moiety can be removed (de-blocking) to permit incorporation of the next nucleotide. Accordingly, on a polymerization initiation site which has a terminator nucleotide incorporated onto its 3' end, the inhibitor moiety can be modified or removed to permit incorporation of the next nucleotide.

In one embodiment, the terminator nucleotides can be non-labeled, or can be operably linked to at least one reporter moiety at any position of the base or sugar, or any of the phosphate groups (alpha, beta, gamma, or terminal phosphate group).

Suitable terminator nucleotides having inhibitor moieties attached to the sugar 3' position, base-linked dyes, where the linkers are cleavable under the same conditions are useful. Suitable terminator nucleotides having photocleavable linkers are also useful.

The terminator nucleotides comprise a nucleotide operably linked to at least one suitable inhibitor moiety. The inhibitor moiety comprises any chemical compound or chemical group which permits incorporation onto the polymerization initiation site, in a template-dependent manner, by a nucleic acid-dependent polymerase, but inhibits incorporation of the next nucleotide. The inhibitor moiety can modify, substitute, or protect, any portion of the nucleotide (e.g., base, sugar, or phosphate group). A suitable inhibitor moiety can be operably linked to any part of the nucleotide (or nucleoside) including the base or sugar moiety, or any phosphate group. The suitable inhibitor moiety can permit incorporation of the terminator nucleotide, in a polymerase-driven, template-dependent manner, but inhibits, stalls, or slows down incorporation of the next nucleotide by the polymerase. The suitable inhibitor moiety inhibits incorporation of the next nucleotide by physical, chemical, or charge interaction with the polymerase or incoming nucleotide.

The suitable inhibitor moiety can be operably linked to the 2' or 3' position of the sugar moiety. In one embodiment, the 2' or 3'-H or —OH group of the sugar moiety can be modified, substituted, or protected. For example, it is well known that DNA polymerases require a polymerization initiation site having a terminal 3'-OH group. Thus, the inhibitor moiety can be any chemical group or compound, which is not an —OH group, operably linked to the 3' C of the sugar moiety. In some embodiments, the suitable inhibitor moiety can be an —H group operably linked to the 3' C of the sugar moiety. Such embodiments include dideoxynucleotides and dideoxynucleotides.

The suitable inhibitor moiety can be operably linked to any position of the nitrogenous base, such as a purine group, including the C2, C4, C5, N3, or C6, of cytosine, thymine, and uracil. The suitable inhibitor moiety can be operably linked to any position of the pyrimidine group, including the C2, C6, C8, N3 and N7 of adenine and guanine.

The suitable inhibitor moiety can be operably linked to any phosphate group, such as the alpha, beta, gamma, or a terminal phosphate group.

In another embodiment, the suitable inhibitor moiety can be linked to any portion of the nucleoside or nucleotide, and sterically hinder the incoming nucleotide. In yet another embodiment, the suitable inhibitor moiety can be a charged group (positive or negative) and linked to any portion of the nucleoside or nucleotide and can inhibit the polymerase from incorporating the next nucleotide. In another embodiment, the suitable inhibitor moiety can be linked to at least one of: a sterically-hindering group, fluorophore, or quencher, in any order and in any combination.

The suitable inhibitor moiety comprises any group including: amine, alkyl, alkenyl, alkynyl, alkyl amide, aryl, ether, ester, benzyl, propargyl, propynyl, phosphate, or analog thereof. For example, the suitable inhibitor moiety can be a 3'-O-allyl moiety.

Suitable inhibitor moieties are well known in the art, and include: fluorenylmethyloxycarbonyl (FMOC), 4-(anisyl) diphenylmethyltrityl (MMTr), dimethoxytrityl (DMTr), monomethoxytrityl, trityl (Tr), benzoyl (Bz), isobutyryl (ib), pixyl (pi), ter-butyl-dimethylsilyl (TBMS), and 1-(2-fluorophenyl)-4-methoxypiperidin 4-yl (FPMP).

The suitable inhibitor moiety can be a reporter moiety (e.g., fluorescent dye) operably linked to the base or sugar moiety. For example, a fluorescent dye operably linked to the base via a 2-nitrobenzyl group, where the 2-nitrobenyl group has the alpha carbon substituted with one alkyl or aryl group. The 2-nitrobenzyl group can be photocleavable.

In another example, the suitable inhibitor moiety can be a reporter moiety (e.g., fluorescent dye, e g, ALEXA FLUOR 549) operably linked to the 5 position of pyrimidines or the 7 position of the purines, via a cleavable disulfide linker.

In yet another example, the suitable inhibitor moiety can be a rhodamine-type dyes, such as R6G, R110, ROX, or TAMRA, or dichloro-derivatives thereof, which are based-linked dyes, including the commercially-available rhodamine dye terminator nucleotides from Applied Biosystems. The suitable inhibitor moiety can be a charged group (positive or negative) or a group capable of becoming charged, including a carboxylic acid, carboxylated, phosphate, diphosphate, peptide, dipeptide, sulfate, disulfate, caproic acid, or amino acid (e.g., a negatively charged amino acid such as aspartic acid, glutamic acid, histidine, lysine, or arginine).

The suitable inhibitor moiety can be a non-incorporatable nucleotide or nucleoside which is linked to the base by a tether. The tether can be linked to a fluorescent label. The tether can include a cleavable moiety, such as a disulfide group. The suitable inhibitor moiety can be a hydrocaryldithiomethyl-modified compound. The suitable inhibitor moiety can include an ethyl dithio linker. The suitable inhibitor moiety can be an alkyl chain homologue having any chain length, which can be produced by replacing 2-bromoethanol and ethylsulfide reagents with any alkyl chain homologue. The suitable inhibitor moiety can be any phosphate, SO3, or C(O)R group, or modified groups thereof. In the C(O)R group, R can be an H, alkyl, benzyl, aryl, alkenyl, alkynyl group, any combination thereof.

In one embodiment, removal or modification of the inhibitor moiety which is attached to the 3' C of the sugar moiety, and restoration of a 3'-OH group, can permit incorporation of a subsequent nucleotide (e.g., reversible terminator nucleotide). In another embodiment, removal or modification of the inhibitor moiety which is attached to the sugar, base, or phosphate group, can permit incorporation of a subsequent nucleotide (e.g., reversible terminator nucleotide).

In one aspect, a suitable linker operably links the terminator nucleotide to the inhibitor moiety. The suitable linker does not interfere with the function or activity of the nucleotide, nucleoside, or inhibitor moiety. The suitable linker can be cleavable or fragmentable to permit removal of the inhibitor moiety. The suitable linker can be the inhibitor moiety. In one embodiment, the nucleotide can be attached directly to the inhibitor moiety without an intervening linker. Various linkers and linker chemistries for generating the terminator nucleotides are disclosed infra.

The terminator nucleotides can be linked to inhibitor moieties using any suitable linking scheme, including linking schemes using amine linkers, or primary or secondary amines, or a rigid hydrocarbon arm.

The terminator nucleotide can include more than one linker, where the linkers are the same or different. The multiple linkers can be removed, cleaved or fragmented using different temperatures, enzymatic activities, chemical agents, or different wavelengths of electromagnetic radiation.

In the terminator nucleotide, the suitable linker can be cleavable by heat, enzymatic activity, chemical agent, or electromagnetic radiation. Cleavable groups include: disulfide, amide, thioamide, ester, thioester, vicinal diol, or hemiacetal. Other cleavable bonds include enzymatically-cleavable bonds, such as peptide bonds (cleaved by peptidases), phosphate bonds (cleaved by phosphatases), nucleic acid bonds (cleaved by endonucleases), and sugar bonds (cleaved by glycosidases).

In one embodiment, the cleavable linker can be a photocleavable linker, such as a 2-nitrobenzyl linker, or others. Analogs of the 2-nitrobenzyl linker, and other photocleavable linkers can be used as cleavable blocking groups, including: 2-nitrobenzyloxycarbonyl (NBOC); nitroveratryl; 1-pyrenylmethyl; 6-nitroveratryloxycarbonyl (NVOC); dimethyldimethoxy-benzyloxycarbonyl (DDZ); 5-bromo-7-nitroindolinyl; O-hydroxy-alpha-methyl-cinnamoyl; methyl-6-nitroveratryloxycarbonyl; methyl-6-nitropiperonyloxycarbonyl; 2-oxymethylene anthraquinone; dimethoxybenzyloxy carbonyl; 5-bromo-7-nitroindolinyl; O-hydroxy-alpha-methyl cinnamoyl; t-butyl oxycarbonyl (TBOC), and 2-oxymethylene anthriquinone. The photocleavable linkers can be illuminated with an electromagnetic source at about 320-800 nm, depending on the particular linker, to achieve cleavage. For example, 1-(2-nitrophenyl) ethyl can be cleaved with light at about 300-350 nm, and 5-bromo-7-nitroindolinyl can be cleaved with light at about 420 nm. In another embodiment, the photocleavable linker can serve as the inhibitor moiety.

In another embodiment, the terminator nucleotide can include two or more cleavable linkers, each attached to a different portion of the nucleotide. For example, the terminator nucleotide can include two different photo-cleavable linkers that are cleavable with the same or different wavelengths of light.

In another embodiment, the linker can be an ethyl dithio or an alkyl chain linker. In another embodiment, the cleavable linker can be a disulfide-linker which is a chemically-cleavable linker. In yet another embodiment, the cleavable linker can be an allyl moiety which is cleavable by palladium (Pd(0)) in a deallylation reaction, or an azidomethyl group which is cleavable with Tris(2-carboxyethyl)phosphine (TCEP) in aqueous solution. In still another embodiment, the linker can be cleavable with silver nitrate (AgNO3). In another embodiment, an azidomethyl group can serve as an inhibitor moiety and a cleavable linker.

A procedure for synthesizing a terminator nucleotide having an unblocked 3'OH group and carrying a biotin molecule linked to the base moiety (N6-alkylated base) via a 2-nitrobenzyl linker can be envisaged.

In the terminator nucleotide, the suitable fragmentable linker is capable of fragmenting in an electronic cascade self-elimination reaction. In some embodiments, the fragmentable linker comprises a trigger moiety. The trigger moiety comprises a substrate that can be cleaved or "activated" by a specified trigger agent. Activation of the trigger moiety initiates a spontaneous rearrangement that results in the fragmentation of the linker and release of the enjoined compound. For example, the trigger moiety can initiate a ring closure mechanism or elimination reaction. Various elimination reactions, include 1,4-, 1,6- and 1,8-elimination reactions.

Any means of activating the trigger moiety may be used. Selection of a particular means of activation, and hence the trigger moiety, may depend, in part, on the particular fragmentation reaction desired. In some embodiments, activation is based upon cleavage of the trigger moiety. The trigger moiety can include a cleavage site that is cleavable by a chemical reagent or enzyme. For example, the trigger moiety can include a cleavage recognition site that is cleavable by a sulfatase (e.g., SO3 and analogs thereof), esterase, phosphatase, nuclease, glycosidase, lipase, esterase, protease, or catalytic antibody.

In an example, photodiodes used for detection can be implemented such that they are fully depleted. Correlated double sampling is used to eliminate thermal noise of the pixel, creating a highly sensitive pixel. Read noise can be less than a few electrons. To increase sensitivity even further, electron-multiplication (EM) gain can be used. The structure to enable EM gain can be implemented in the non-photosensitive area of the pixel. A large electric field can be created between adjacent electrodes after charge is transferred from the photodiode or CCD. As the electric field becomes large enough, impact ionization occurs and the collected electrons are multiplied. This multiplication process allows the pixel to have noise levels less than 1 electron such that the pixel is single photon sensitive. Furthermore, the pixels can be arranged near the polymerase such that no optical occlusions occur in the path of transduction, which can give a 100% fill factor, which allows for high quantum efficiency.

Figure 42:
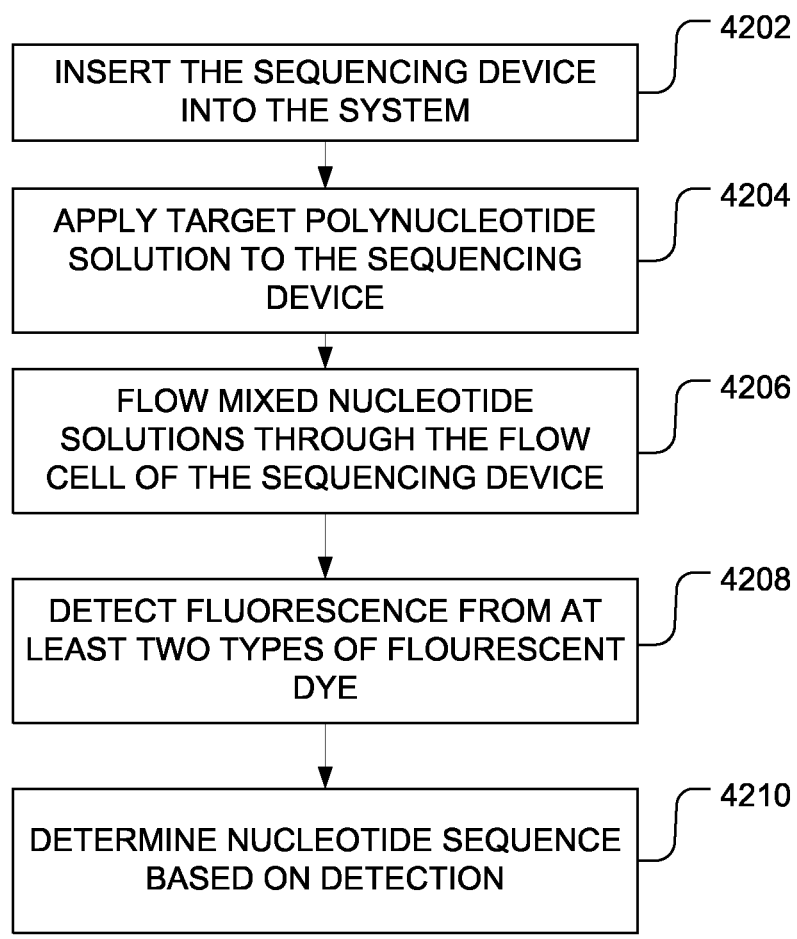
FIG. 42 and FIG. 43 include flow diagrams illustrating exemplary methods for utilizing an exemplary system.

FIG. 42 includes an illustration of exemplary method for sequencing. For example, a sequencing device is inserted into a system, as illustrated at 4202. The sequencing device can be placed in fluid communication with a fluidics system and in electrical communication with a computational system. A target polynucleotide solution can be applied to the sequencing device, as illustrated at 4204. Optionally, the target polynucleotide solution can be applied prior to inserting the sequencing device into the system. In such a case, the target polynucleotide can be localized within regions of a surface corresponding with pixels. In another example, enzymes may be localized to the surface and a target polynucleotide may be applied to the system and captured by the enzymes localized to the surface.

Once polynucleotide targets are localized within the system, solutions including at least one type of labeled nucleotide can be contacted with at least one of the targets. For example, a mixed nucleotide solution including at least two different nucleotide types, each type modified with a different dye having a different fluorescent spectrum, can flow through the flow cell of the sequencing device, as illustrated 4206. In a particular example, a nucleotide solution including four nucleotide types, each type modified with a different associated dye having different emission spectrum, can be applied to the sequencing device. As a result of incorporation of nucleotides along a target polynucleotide, fluorescence can be detected from the fluorescent dye associated with the types of nucleotides, as illustrated at 4208. For example, the solution including at least two dye modified nucleotide types is applied, incorporation of the two different types can be detected based on fluorescence at two different spectrums.

As illustrated 4210, the sequence of nucleotide incorporations associated with fluorescent emissions can be used to determine the base identities of one or more incorporated nucleotides. For example, a base calling subroutine can determine, based on the sequence of detected fluorescent signals detected by a single pixel, a sequence of nucleotide bases along a target polynucleotide.

Figure 43:
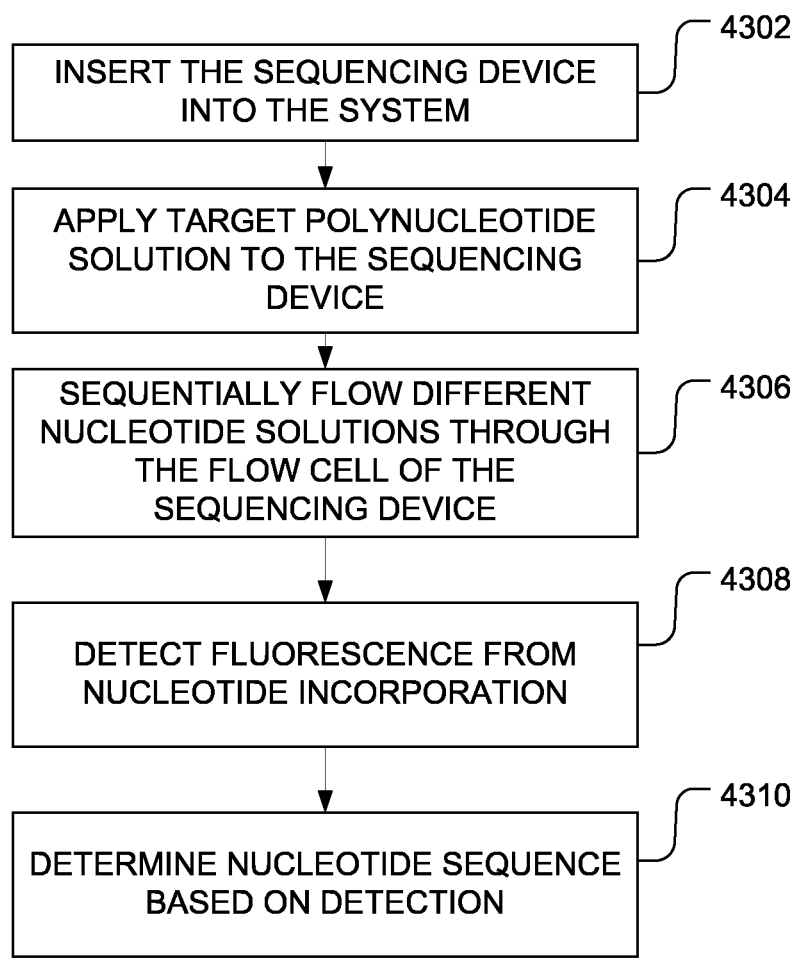

In another exemplary method illustrated in FIG. 43, a sequencing device can be inserted into the system, as illustrated at 4302. A target polynucleotide solution can be applied to a sequencing device, as illustrated at 4304. As above, the target polynucleotide can be applied prior to inserting the sequencing device in the system when the target polynucleotide is to be tethered to a surface. Alternatively, an enzyme tethered to the surface of the polynucleotide is provided prior to flowing nucleotide solutions and the sequencing device.

The nucleotide solutions each including a different type of dye-modified nucleotide can flow sequentially through the sequencing device, as illustrated at 4306. Optionally, four different nucleotide solutions each including a different type of nucleotide modified with a dye can be utilized sequentially, flowing a different nucleotide solution between flows of a wash solution. Fluorescent emissions emitted as a result of nucleotide incorporation can be detected, as illustrated 4308. In a particular example in which four different nucleotide solutions are utilized, a fluorescent emission can indicate incorporated base based on the solution flowing at the time the emitted fluorescence. As such, a single dye can be used. Alternatively, multiple dyes can be used.

As a result of the detection, a nucleotide sequence can be determined, as illustrated at 4310. The sequence of fluorescent signals associated with the nucleotide solution flowing at time of a fluorescent signal can be utilized to determine the sequence of nucleotides incorporated during template-dependent synthesis driven by a given target polynucleotide that is associated with a single pixel.

Advantageously, a system can be formed without an external microscope objective and EM-CCDs and instead with a CMOS photosensitive substrate. In particular, the system advantageously includes a high density array of incorporation detectors integrated on a CMOS substrate. Optionally, the system includes immobilization of the enzyme, such as a DNA polymerase, at each detector or immobilization of the DNA strand at each detector. Each incorporation detector can contains an integrated radiation source as well as the spectrally sensitive detector. Spectral selectivity can be obtained by multiple confinement wells placed at various depths within the same pixel, can be implemented with permanent use color filter photoresist, or can be implemented with absorption layers tuned with thickness. The excitation light source can be integrated local to each incorporation site and bound within the semiconductor substrate using hot carrier direct recombination. Data for each incorporation site may be limited to 3 bits indicating an incorporation event along with the color.

In some embodiments, the disclosure relates generally to methods, as well as related compositions, systems, apparatuses and devices, for detecting a signal, or a change in a signal, emitted by a labeled nucleotide in a nucleotide incorporation reaction.

In some embodiments, a method for sequencing a target polynucleotide, comprises the steps of: contacting a device with an enzymatic reaction, wherein the enzymatic reaction includes contacting: (i) a polymerase with (ii) at least one target polynucleotide which is base paired with a primer and with (iii) at least one type of a nucleotide having an optically detectable moiety, thereby incorporating a nucleotide onto the primer, wherein the device comprises any of the integrated devices described herein that have detectors that detect signals from a nucleotide incorporation reaction. The method further comprises the steps of: generating an optically detectable signal by exciting the optically detectable moiety with an excitation source; and detecting the optically detectable signal. The method further comprises the steps of: identifying the incorporated nucleotide.

In some embodiments, a method for sequencing a target polynucleotide further comprises a second enzymatic reaction including the steps of: contacting the device with a second enzymatic reaction, wherein the second enzymatic reaction includes contacting: (i) a second polymerase with (ii) the at least one target polynucleotide which is base paired with the primer and with (iii) at least one type of a nucleotide having an optically detectable moiety, thereby incorporating a second nucleotide onto the primer. The method can further comprise the steps of: generating a second optically detectable signal by exciting the second optically detectable moiety with an excitation source; and detecting the second optically detectable signal. The method further comprises the steps of: identifying the incorporated nucleotide.

Alternatively, the method for sequencing further comprises a different second enzymatic reaction, comprising: contacting the device with a second enzymatic reaction, wherein the second enzymatic reaction includes contacting: (i) a second polymerase with (ii) the at least one target polynucleotide which is base paired with the primer and with (iii) at least one type of a nucleotide lacking an optically detectable moiety, thereby incorporating onto the primer the at least one type of nucleotide lacking an optically detectable moiety. This embodiment is known as "dark" sequencing.

In some embodiments, a method for sequencing a target polynucleotide further comprises a third enzymatic reaction including the steps of: contacting the device with a third enzymatic reaction, which includes at least one type of a second nucleotide lacking an optically detectable moiety; and incorporating onto the primer the second nucleotide lacking the optically detectable moiety.

Alternatively, the method for sequencing further comprises a different third enzymatic reaction, comprising: contacting the device with a third enzymatic reaction, wherein the enzymatic reaction includes at least one type of a nucleotide having an optically detectable moiety; and generating a second optically detectable signal by exciting the optically detectable moiety with an excitation source; detecting the second optically detectable signal; and identifying the second incorporated nucleotide.

In some embodiments, a method for sequencing a target polynucleotide further comprises a fourth enzymatic reaction including the steps of: contacting the device with a fourth enzymatic reaction, wherein the enzymatic reaction includes at least one type of a nucleotide having an optically detectable moiety; generating a second optically detectable signal by exciting the optically detectable moiety with an excitation source; detecting the second optically detectable signal; and identifying the second incorporated nucleotide.

In some embodiments, any combination of the first, second, third and fourth nucleic sequencing reactions can be conducted with (i) at least one type of nucleotide linked to an optically-detectable moiety such as an energy transfer acceptor moiety, and (ii) a polymerase linked to an energy transfer donor moiety. In some embodiments, any combination of the first, second, third and fourth nucleic sequencing reactions can be conducted with a mutant polymerase having altered nucleotide incorporation kinetics, which include: altered polymerase binding to the target molecule, altered polymerase binding to the nucleotide, altered polymerase catalyzing nucleotide incorporation, altered the polymerase cleaving the phosphate group or substituted phosphate group, or altered polymerase releasing the cleavage product.

In some embodiments, the disclosure relates generally to methods, as well as related compositions, systems, apparatuses and devices, for generating an energy transfer signal comprising the steps of: contacting a device with an enzymatic reaction, where the enzymatic reaction includes contacting: (i) a polymerase linked to an energy transfer donor moiety with (ii) a target nucleic acid molecule which is base-paired with a primer and with (iii) at least one type of a nucleotide having an energy transfer acceptor moiety, thereby incorporating the nucleotide onto the primer, and locating the polymerase and the at least one type of nucleotide in close proximity with each other to generate an energy transfer signal, wherein the device comprises any of the integrated devices described herein that have detectors that detect signals from a nucleotide incorporation reaction.

In some embodiments, for energy transfer sequencing methods, the polymerase is a mutant polymerase having altered nucleotide incorporation kinetics. In some embodiments, the mutant polymerase has altered nucleotide incorporation kinetics, which include: altered polymerase binding to the target molecule, altered polymerase binding to the nucleotide, altered polymerase catalyzing nucleotide incorporation, altered the polymerase cleaving the phosphate group or substituted phosphate group, or altered polymerase releasing the cleavage product (see e.g., U.S. published application No. 2012/0322057, published Dec. 20, 2012, hereby incorporated by reference in its entirety). In some embodiments, the energy transfer donor moiety comprises a nanoparticle (U.S. Pat. No. 8,603,792, issued Dec. 10, 2013, to Nikiforov, hereby incorporated by reference in its entirety). In some embodiment, the sequencing reaction is conducted with a single target nucleic acid molecule (target polynucleotide). In some embodiments, the mutant polymerase comprises the amino acid sequence found in any of SEQ ID NOS:1-3 of U.S. published application No. 2012/0329042, published Dec. 27, 2012 (hereby incorporated by reference in its entirety).

In some embodiments, the disclosure relates generally to methods, as well as related compositions, systems, apparatuses and devices, for detecting a signal, or a change in a signal, emitted by a labeled nucleotide which is transiently-bound to a polymerase and the template nucleotide. The detected signal can be used to identify the transiently-bound nucleotide and deduce the identity of the bound nucleotide.

The methods can be practiced using any suitable reaction condition comprising reagents and components which mediate polymerase-dependent reactions, including: forming the complex (template molecule/initiation site/polymerase); transient-binding a labeled nucleotide to a polymerase in a template-dependent manner (without nucleotide incorporation); and detecting the signal (or change in a signal) from the transiently-bound labeled nucleotide. The methods can include a separate step for incorporating a nucleotide. In some embodiments, transiently-binding a nucleotide to a polymerase, without polymerizing, includes not forming a covalent bond between the transiently bound nucleotide and a free 3?-OH end of a primer or nucleic acid molecule. The methods can be practiced using one or more different types of polymerases. For example, the methods can be practiced using one type of polymerase for the transient-binding step, and the same or different type of polymerase for the nucleotide incorporation step. The methods can be practiced using one or more different types of nucleotides. The methods can be practiced using separate, step-wise reactions: contacting, binding, detecting, incorporating, or removing.

The transient-binding methods can be performed on any type of polymerase-dependent platform, including: single molecule, arrays of single molecules, populations of immobilized template molecules (i.e., multiple copies of the same template molecule immobilized on a device, support, solid surface or bead, etc), direct excitation/detection, FRET-based excitation/detection, fluorescence polarization, non-immobilized polymerase/template complex, or any combination thereof (see U.S. Pat. No. 8,632,975, issued on Jan. 21, 2014 to Vander Horn, hereby incorporated by reference in its entirety).

In some embodiments, methods for transiently binding a nucleotide to a polymerase can be conducted under any reaction condition which permits the polymerase to selectively bind a complementary nucleotide, but incorporation of the complementary nucleotide is perturbed, impeded, or inhibited. Such reaction conditions include utilizing: (1) any reaction conditions and reagents, such as temperature, pH, ionic strength, multivalent cations, or time; (2) any polymerase which selectively binds a complementary nucleotide but exhibits reduced nucleotide incorporation activity; (3) non-incorporatable nucleotides; or (4) a non-extendible polymerization initiation site. Any combination of these reaction conditions can be practiced in any order in the transient-binding methods provided herein.

In some embodiments, methods for detecting the presence of a transiently-bound nucleotide comprise the steps of: (a) contacting a device with an enzymatic reaction, wherein the enzymatic reaction comprises: contacting at least one type of a labeled nucleotide to a complex having a first polymerase bound to at least one target polynucleotide that is bound to a primer, under suitable conditions to transiently-bind, without polymerizing, the at least one type of labeled nucleotide to the polymerase in a nucleic acid template-dependent manner; (b) detecting the transiently-bound labeled nucleotide; and (c) identifying the labeled nucleotide transiently-bound to the polymerase, wherein the device comprises any of the integrated devices described herein that have detectors that detect signals from a nucleotide incorporation reaction. The steps (a)-(c) can be repeated at least once. In some embodiments, the method further comprises the steps of: (d) removing the transiently-bound nucleotide; and (e) contacting the complex with at least one type of a second nucleotide under suitable conditions for a second polymerase to polymerize the second nucleotide. The steps (d)-(e) can be repeated at least once. The steps (a)-(e) can be repeated at least once.

In some embodiments, the suitable conditions for transiently-binding a nucleotide include conducting the enzymatic reaction in the presence of a cation that inhibits nucleotide incorporation by the polymerase. In some embodiments, the labeled nucleotide comprises a nucleotide linked to an optically detectable moiety. In some embodiments, the methods include: generating an optically detectable signal by exciting the optically detectable moiety with an excitation source; and detecting the optically detectable signal. In some embodiments, the methods further comprise: identifying the incorporated nucleotide (the second nucleotide). In some embodiments, the incorporated nucleotide produces a nucleotide incorporation byproduct. The nucleotide incorporation byproduct includes pyrophosphate, hydrogen ions or protons. In some embodiments, the methods further comprise: detecting the nucleotide incorporation byproduct. In some embodiment, the sequencing reaction is conducted with a single target nucleic acid molecule (target polynucleotide).

In some embodiments, methods for detecting the presence of a transiently-bound nucleotide comprise the steps of: (a) contacting a device with an enzymatic reaction, wherein the enzymatic reaction comprises: contacting at least one type of a labeled nucleotide to a complex which comprises a polymerase bound to a template nucleic acid molecule which is base-paired to a primer having a polymerization initiation site, under conditions suitable to transiently-bind the labeled nucleotide to the polymerase in a template-dependent manner but inhibits incorporation of the nucleotide; (b) exciting the labeled nucleotide or the polymerase with an excitation source; and (c) detecting a signal, or a change in a signal, emitted by the transiently-bound labeled nucleotide in step (a), thereby detecting the presence of the transiently-bound nucleotide, wherein the device comprises any of the integrated devices described herein that have detectors that detect signals from a nucleotide incorporation reaction. In some embodiments, methods further comprise the step: (d) identifying the nucleotide transiently-bound to the polymerase. The steps (a)-(c) can be repeated at least once. The steps (a)-(d) can be repeated at least once.

In one embodiment, the methods for identifying a nucleotide bound to a polymerase, further comprises the steps of: (e1) removing the transiently-bound nucleotide; and (f1) contacting the complex with at least one type of nucleotide under suitable conditions for the polymerase to polymerize the nucleotide. In this embodiment, the same polymerase in step (a) is contacted in step (f1). The steps (e1)-(f1) can be repeated at least once. The steps (a)-(f1) can be repeated at least once. In some embodiments, the incorporated nucleotide produces a nucleotide incorporation byproduct. The nucleotide incorporation byproduct includes pyrophosphate, hydrogen ions or protons. In some embodiments, the methods further comprise: detecting the nucleotide incorporation byproduct.

In another embodiment, the methods for identifying a nucleotide bound to a polymerase, further comprises the steps of: (e2) removing the first polymerase and the transiently-bound nucleotide so that the template nucleic acid molecule, nucleic acid primer molecule or self-priming template nucleic acid molecule remains immobilized to the surface; (f2) binding the remaining template nucleic acid molecule with a second polymerase; and (g2) contacting the second polymerase with at least one type of nucleotide under suitable conditions for the second polymerase to polymerize the nucleotide. In this embodiment, the polymerase in step (a) is different from the polymerase in step (f2). The steps (e2)-(g2) can be repeated at least once. The steps (a)-(g2) can be repeated at least once. In some embodiments, the incorporated nucleotide produces a nucleotide incorporation byproduct. The nucleotide incorporation byproduct includes pyrophosphate, hydrogen ions or protons. In some embodiments, the methods further comprise: detecting the nucleotide incorporation byproduct.

In one embodiment, the suitable conditions to transiently bind the nucleotide to the polymerase in step (a1) or (a2) comprise: (i) reducing the levels or omission of a cation that permits nucleotide incorporation or addition of a cation that inhibits nucleotide incorporation; (ii) the polymerase selectively binds the nucleotide in a template-dependent manner and exhibits reduced nucleotide incorporation activity; (iii) the at least one type of labeled nucleotide is a labeled non-incorporatable nucleotide; or (iv) the polymerization initiation site is a non-extendible polymerization initiation site. Any combination of these suitable conditions can be practiced to identify the nucleotide bound to the polymerase.

In another embodiment, the suitable conditions in step (a) comprise: (i) cations present at a concentration that inhibits nucleotide incorporation; (ii) the polymerase selectively binds the nucleotide in a template-dependent manner and exhibits reduced nucleotide incorporation activity; (iii) the at least one type of labeled nucleotide is a labeled non-incorporatable nucleotide; or (iv) the polymerization initiation site is a non-extendible polymerization initiation site.

In one embodiment, the cation that inhibits nucleotide incorporation can be calcium, scandium, titanium, vanadium, chromium, iron, cobalt, nickel, copper, zinc, gallium, germanium, arsenic, selenium, rhodium, or strontium.

In another embodiment, the suitable conditions for polymerizing the nucleotide in step (f1) or (g2) comprise: (i) including a cation that permits nucleotide incorporation or reducing the levels or omission of a cation that inhibits nucleotide incorporation; (ii) using a polymerase which selectively binds the nucleotide in a template-dependent manner and polymerizes the bound nucleotide; (iii) using at least one type of incorporatable nucleotide; or (iv) using a polymerization initiation site having an extendible polymerization initiation site. In some embodiments, cations that permit nucleotide incorporation include magnesium and manganese.

In one embodiment, suitable conditions for incorporating the terminator nucleotide in any of steps (a) and (k) can include a manganese or magnesium compound, or the manganese or magnesium compound can be omitted. In another embodiment, the manganese compound can be $MnCl2$. In another embodiment, the magnesium compound can be $MgCl2$. In another embodiment, the amount of manganese or magnesium compound can be about 1-5 mM, or about 2-5 mM. In another embodiment, the manganese or magnesium compound can be washed away or chelated after any of the steps.

In some embodiments, the polymerase can be an RB69, Phi29, B103 polymerase, or a Klenow fragment. In some embodiments, the polymerase can exhibit exonuclease activity. In another embodiment, the polymerase can be any 9° N polymerase or derivative thereof, including THERMINATOR, THERMINATOR II, or THERMINATOR-GAMMA polymerase (New England Biolabs, catalog # s M0261L, M0266L, and M0334L, respectively). In another embodiment, the second polymerase can be the same type or a different type as the first polymerase. In some embodiments, the polymerase comprise a mutant polymerase, that can have altered nucleotide incorporation kinetics. In some embodiments, the altered nucleotide incorporation kinetics include: altered polymerase binding to the target molecule, altered polymerase binding to the nucleotide, altered polymerase catalyzing nucleotide incorporation, altered the polymerase cleaving the phosphate group or substituted phosphate group, or altered polymerase releasing the cleavage product. In some embodiments, the polymerase comprises the amino acid sequence found in any of SEQ ID NOS: 1-8 found in U.S. published application No. 2010/031114, published Dec. 9, 2010 (hereby incorporated by reference in its entirety).

In some embodiments, any of the nucleic acid sequencing methods described herein include an enzyme that catalyzes polymerization of a nucleotide in a template-dependent manner, including a DNA-dependent polymerase, RNA-dependent polymerase, or a reverse transcriptase. In some embodiments, the polymerase can be a wild-type (e.g., native) or modified/mutant polymerase. In some embodiments, the polymerase can be a thermolabile or thermostable polymerase. In some embodiments, the polymerase lacks exonuclease activity. In some embodiments, the polymerase can bind a labeled nucleotide. In some embodiments, the polymerase can bind an incorporatable or a non-incorporatable nucleotide. In some embodiments, the first or the second polymerase can be operably linked to a reporter moiety (e.g., energy transfer donor moiety).

In some embodiments, any of the nucleic acid sequencing methods described herein include an energy transfer donor moiety, such as a fluorescent dye or nanoparticle (U.S. Pat. No. 8,603,792, issued Dec. 10, 2013, to Nikiforov, hereby incorporated by reference in its entirety). In some embodiments, the nanoparticle comprises an inorganic fluorescent nanoparticle. In some embodiments, the nanoparticle is 1-20 nm in its largest dimension. In some embodiments, the nanoparticle is a non-blinking nanoparticle.

In some embodiments, any of the nucleic acid sequencing methods described herein include a template polynucleotide, which includes a DNA molecule, RNA molecule, or DNA/RNA hybrid molecule. The template polynucleotide comprises a single template nucleic acid molecule or a plurality of template nucleic acid molecules. The plurality of template nucleic acid molecules (target polynucleotides) comprises a population of nucleic acids having different sequences or having substantially identical sequences.

In some embodiments, any of the nucleic acid sequencing methods described herein include a primer having a polymerization initiation site at the 3' terminal end. The primer can be hybridized to the template polynucleotide. The primer can be a self-priming template nucleic acid molecule. In another embodiment, the polymerization initiation site can be base-paired to the template nucleic acid molecule. In another embodiment, the polymerization initiation site can be an extendible terminal 3'OH group or a non-extendible terminal group. In another embodiment, the polymerization initiation site can be a terminal 3'OH group of the nucleic acid primer molecule or a terminal 3'OH group of a self-priming template nucleic acid molecule.

In some embodiments, any of the nucleic acid sequencing methods described herein include one or more nucleic acid molecules attached (immobilized) to a device, support, surface or microsphere. For example, a template polynucleotide, nucleic acid primer molecule, or self-priming template polynucleotide, can be immobilized to a device, support, surface or microsphere. In some embodiments, the device is any integrated device described herein, including those having detectors that detect signals from a nucleotide incorporation reaction. In some embodiments, the support includes a particle or microsphere.

In some embodiments, any of the nucleic acid sequencing methods described herein include at least one type of nucleotide. The nucleotide can be adenosine, guanosine, cytosine, thymidine, uridine or inosine. In some embodiments, the nucleotide includes 3-10 phosphate groups, or more.

In some embodiments, any of the nucleic acid sequencing methods described herein can be conducted with one type of nucleotide, or no more than two different types of nucleotides, or no more than three different types of nucleotides, or no more than four different types of nucleotides, or more than four different types of nucleotides.

In some embodiments, the nucleotide can be non-labeled, or can be linked to at least one reporter moiety. The reporter moiety includes any optically detectable moiety, such as a fluorophore, energy transfer donor moiety or energy transfer acceptor moiety. In some embodiments, the optically detectable moiety is photobleachable. In some embodiments, the optically-detectable moiety is attached to any portion of the nucleotide, including the base, sugar (e.g., 2' or 3' position) or phosphate backbone. The optically detectable moiety is attached to the nucleotide by a linker. In some embodiments, the linker is cleavable with light, heat, a chemical compound or an enzyme. In some embodiments, the cleavable linker can be cleaved with light, heat, a chemical compound or an enzyme.

In some embodiments, the energy transfer donor reporter moiety can be an inorganic nanoparticle or a fluorophore. The energy transfer acceptor moiety can be a fluorophore (e.g., fluorescent dye). The energy transfer donor reporter moiety can be linked to the polymerase or nucleotide. The energy transfer acceptor reporter moiety can be linked to the polymerase or nucleotide. In conducting any of the sequencing methods described herein, as an example, a donor-labeled polymerase binds an acceptor-labeled nucleotide, thereby bringing the polymerase and nucleotide in close proximity to permit energy transfer from the donor to the acceptor and generation of an energy transfer signal. Upon excitation from an excitation source (e.g., electromagnetic energy), the acceptor moiety emits a fluorescent signal.

The nucleotide can be incorporatable or non-incorporatable by a polymerase. The non-incorporatable nucleotide can bind to the polymerase and template nucleic acid molecule which can be base-paired to a polymerization initiation site, in a template-dependent manner, but does not incorporate.

In some embodiments, any of the nucleic acid sequencing methods described herein include at least one nucleotide linked to at least one inhibitor moiety to generate a terminator nucleotide. The inhibitor moiety (e.g., blocking moiety) can permit incorporation of the terminator nucleotide but inhibits incorporation of a subsequent nucleotide. The inhibitor moiety can be linked to any portion of the nucleotide including the base, sugar (e.g., 2' or 3' position) or phosphate backbone. The inhibitor moiety can be linked to the nucleotide by a cleavable linker that is cleavable with an enzyme, heat, chemical compound, or light. In another embodiment, the inhibitor moiety can be removed via an enzymatic, heat, chemical or light cleavage reaction.

In some embodiments, any of the nucleic acid sequencing methods described herein include at least one nucleotide that is a dideoxyribonucleotide.

In some embodiments, any of the nucleic acid sequencing methods described herein can be conducted by contacting a polymerase with a mixture of nucleotides. The mixture can include different types of nucleotides that differ from each other in their base, sugar or phosphate backbone. The mixture can include only labeled nucleotides, or only non-labeled nucleotides, or at least one labeled (e.g., optically detectable moiety) and at least one non-labeled nucleotide.

The mixture can include two, three, four, or more different types of nucleotides. For example, the mixture can include: (i) one type of nucleotide having an optically detectable moiety and two or three different types of nucleotides that lack an optically detectable moiety; or (ii) two different types of nucleotides having different optically detectable moieties and one or two different types of nucleotides that lack an optically detectable moiety; or (iii) three different types of nucleotides having different optically detectable moieties and one type of nucleotide that lacks an optically detectable moiety. In conducting a nucleic acid sequencing reaction, the polymerase can be contacted with the different types of nucleotide in the mixture of nucleotides essentially simultaneously or sequentially.

In some embodiments, any of the nucleic acid sequencing methods described herein include an excitation source for exciting the optically-detectable moiety. The excitation source includes electromagnetic energy or light.

In some embodiments, any of the nucleic acid sequencing methods described herein can be conducted on a single site on a device, or at a plurality of sites on the device. The plurality of sites on the device can be arranged in an organized or random array. The plurality of sites on the device can be arranged in rectilinear or hexagonal pattern.

In some embodiments, any of the nucleic acid sequencing methods described herein can be conducted in a massively parallel manner. The nucleic acid sequencing reactions can be conducted by subjecting a plurality of target polynucleotides to the same enzymatic reaction in parallel, wherein the plurality of target polynucleotides comprises a population of nucleic acids having substantially identical sequences or different sequences.

In some embodiments, any of the nucleic acid sequencing methods described herein include nucleotide incorporation reactions which produce one or more nucleotide incorporation byproducts resulting from the polymerase catalyzing nucleotide polymerization. In some embodiments, nucleotide incorporation byproducts include pyrophosphate molecules, hydrogen ions, or protons.

In some embodiments, any of the nucleic acid sequencing methods described herein can be conducted by flowing reagents to the surface of the integrated device, where the flow contains at least one reagent for conducting nucleic acid sequencing reactions, including polymerases, one type of nucleotides or a mixture of different types of nucleotides, cations that inhibit nucleotide incorporation, cations that permit nucleotide incorporation, and cleaving agents. The flow can deliver to the surface of the device multiple different reagents sequentially or essentially simultaneously.

Each of the above sequencing techniques can be used in conjunction with embodiments of the above described devices and systems.

In a first aspect, a device includes a transparent layer defining a surface exposed to a flow volume and to secure a target polynucleotide template and a detector structure in optical communication with and secured to the transparent layer and including a plurality of detectors configured to detect a fluorescent signal emitted during nucleotide incorporation during template-dependent nucleic acid synthesis.

In an example of the first aspect, the detector structure includes a plurality of pixels, each pixel of the plurality of pixels including at least two detectors of the plurality of detectors. For example, the at least two detectors are disposed adjacent one anther within a plan view. In another example, the at least two detectors are disposed one over the other when viewed in cross-section. In a further example, each pixel includes at least three detectors. For example, each pixel can include at least four detectors.

In another example of the first aspect and the above examples, the transparent layer includes an energy propagation layer.

In a further example of the first aspect and the above examples, the device further includes an energy propagation layer disposed between the transparent layer and the detector structure. For example, the energy propagation layer includes a total internal reflection layer. In another example, the device further includes an energy emitting component to provide energy to the energy propagation layer.

In an additional example of the first aspect and the above examples, the device further includes a separator structure extending from the detector structure toward the transparent layer, the separator structure opaque to the fluorescent signal.

In another example of the first aspect and the above examples, the device further includes a filter layer disposed between the device structure and the transparent layer. For example, the filter layer is configured to limit transmission of excitation energy. In another example, the filter layer is configured to permit the transmission of a wavelength spectrum associated with a dye.

In a further example of the first aspect and the above examples, the device further includes a well structure defining wells disposed on the transparent layer opposite the detector structure.

In an additional example of the first aspect and the above examples, the device further includes a pad structure disposed on the transparent layer opposite the detector structure.

In another example of the first aspect and the above examples, the device further includes a lid, the flow volume defined between the lid and the transparent layer.

In a further example of the first aspect and the above examples, the transparent layer comprises an electrode.

In a second aspect, an apparatus includes a transparent layer defining a surface exposed to a flow volume and to secure a target polynucleotide template; an energy propagation layer disposed opposite the surface of the transparent layer to propagate photonic energy along a path parallel to the surface; an excitation filter layer secured to the energy propagation layer opposite the transparent layer, the excitation filter layer opaque to the photonic energy; and a detector structure secured to the excitation filter layer opposite the energy propagation layer, the detector structure defining a plurality of pixels, each pixel including a detector, each pixel of the plurality of pixels uniquely optically associated with a well of the plurality of wells.

In an example of the second aspect, each pixel includes at least two detectors. For example, the at least two detectors can be disposed adjacent one another within a plan view. In another example, the at least two detectors are disposed one over the other when viewed in cross-section. In an additional example, each pixel includes at least three detectors. For example, each pixel can include at least four detectors. In a further example, the energy propagation layer includes a total internal reflection layer. For example, the apparatus can further include an energy emitting component to provide energy to the energy propagation layer.

In another example of the second aspect and the above examples, the apparatus can further include a separator structure extending from the detector structure toward the transparent layer.

In a further example of the second aspect and the above examples, the apparatus can further include a filter layer disposed between the device structure and the transparent layer, wherein the filter layer is configured to permit the transmission of a wavelength spectrum associated with a dye.

In an additional example of the second aspect and the above examples, the apparatus can further include a well structure defining wells disposed on the transparent layer opposite the detector structure.

In another example of the second aspect and the above examples, the apparatus further includes a pad structure disposed on the transparent layer opposite the detector structure.

In a further example of the second aspect and the above examples, the apparatus further includes a lid, the flow volume defined between the lid and the transparent layer.

In an additional example of the second aspect and the above examples, the transparent layer comprises an electrode.

In a third aspect, an apparatus includes a transparent layer defining a surface exposed to a flow volume and to secure a target polynucleotide; a well structure defining a plurality of wells that expose the transparent layer; an energy propagation layer disposed opposite the surface of the transparent layer and the well structure; an excitation filter layer secured to the energy propagation layer opposite the transparent layer; a color filter layer secured to the excitation filter layer opposite the energy propagation layer; a detector structure secured to the color filter layer opposite the excitation filter layer, the detector structure defining a plurality of pixels, each pixel including at least two detectors, each pixel of the plurality of pixels uniquely optically associated with a well of the plurality of wells; and a plurality of opaque structures disposed between pixels and extending from the detector structure toward the transparent layer.

In a fourth aspect, a system includes a fluidics system including a valve structure and a plurality of reagent containers; a computational system including a controller; and an integrated device. The integrated device includes a transparent layer defining a surface exposed to a flow volume and to secure a target polynucleotide; and a detector structure secured to the transparent layer and including a plurality of detectors to detect a fluorescent signal emitted during nucleotide incorporation using the target polynucleotide as a template, wherein the fluidics system is in communication with the flow volume, and wherein the controller is in communication with the detector structure.

In a fifth aspect, a method of obtaining sequence information from a polynucleotide target includes applying a sequencing device to a sequencing system, the sequencing device defining a flow volume and including a transparent layer including a surface exposed to the flow volume and a detector structure disposed on an opposite side of the transparent layer from the flow volume; applying a polynucleotide to the sequencing device; incorporating at least one nucleotide into a nascent nucleic acid molecule using the polynucleotide as a template; and detecting a fluorescent signal with the detector structure, the fluorescent signal indicative of nucleotide incorporation.

In an example of the fifth aspect, the nucleotide solution includes at least two dye modified nucleotide types.

In another example of the fifth aspect or the above examples, the nucleotide solution includes four different dye modified nucleotide types.

In a further example of the fifth aspect or the above examples, applying the nucleotide solution includes sequentially applying at least two different nucleotide solutions.

In a sixth aspect, a method for sequencing a target polynucleotide includes contacting the device of any one of the first, second, or third aspects or examples thereof with an enzymatic reaction, wherein the enzymatic reaction includes contacting: (i) a polymerase with (ii) at least one target polynucleotide which is base paired with a primer and with (iii) at least one type of a nucleotide having an optically detectable moiety, thereby incorporating a nucleotide onto the primer.

In an example of the sixth aspect, the method further includes a) generating an optically detectable signal by exciting the optically detectable moiety with an excitation source; and b) detecting the optically detectable signal.

In another example of the sixth aspect and the above examples, the method further includes identifying the incorporated nucleotide.

In a further example of the sixth aspect and the above examples, the method further includes contacting the device with a second enzymatic reaction, wherein the second enzymatic reaction includes contacting: (i) a second polymerase with (ii) the at least one target polynucleotide which is base paired with the primer and with (iii) at least one type of a nucleotide having an optically detectable moiety, thereby incorporating a second nucleotide onto the primer.

In an additional example of the sixth aspect and the above examples, the method further includes a) generating a second optically detectable signal by exciting the second optically detectable moiety with an excitation source; and b) detecting the second optically detectable signal.

In another example of the sixth aspect and the above examples, the method further includes identifying the second incorporated nucleotide.

In a further example of the sixth aspect and the above examples, the method further includes contacting the device with a second enzymatic reaction, wherein the second enzymatic reaction includes contacting: (i) a second polymerase with (ii) the at least one target polynucleotide which is base paired with the primer and with (iii) at least one type of a nucleotide lacking an optically detectable moiety, thereby incorporating onto the primer the at least one type of nucleotide lacking an optically detectable moiety. For example, the method further includes a) contacting the device with a third enzymatic reaction, which includes at least one type of a second nucleotide lacking an optically detectable moiety; and b) incorporating onto the primer the second nucleotide lacking the optically detectable moiety.

In an additional example of the sixth aspect and the above examples, the method further includes a) repeating the step of contacting the device with a third enzymatic reaction, wherein the enzymatic reaction includes at least one type of a nucleotide having an optically detectable moiety; b) generating a second optically detectable signal by exciting the optically detectable moiety with an excitation source; c) detecting the second optically detectable signal; and d) identifying the second incorporated nucleotide.

In another example of the sixth aspect and the above examples, the method further includes a) contacting the device with a third enzymatic reaction, wherein the enzymatic reaction includes at least one type of a nucleotide having an optically detectable moiety; b) generating a second optically detectable signal by exciting the optically detectable moiety with an excitation source; c) detecting the second optically detectable signal; and d) identifying the second incorporated nucleotide.

In a seventh aspect, a method for generating an energy transfer signal includes contacting the above devices with a enzymatic reaction, wherein the enzymatic reaction includes contacting: (i) a mutant polymerase having altered nucleotide incorporation kinetics and linked to an energy transfer donor moiety with (ii) a target polynucleotide which is base paired with a primer and with (iii) at least one type of a nucleotide having an energy transfer acceptor moiety, thereby incorporating a nucleotide onto the primer, and locating the polymerase and the at least one type of nucleotide in close proximity with each other to generate the energy transfer signal, wherein the altered nucleotide incorporation kinetics includes altered polymerase binding to the target molecule, altered polymerase binding to the nucleotide, altered polymerase catalyzing nucleotide incorporation, altered the polymerase cleaving the phosphate group or substituted phosphate group, or altered polymerase releasing the cleavage product.

In an example of the sixth and seventh aspects, the associated examples, and the above examples, the first polymerase and the second polymerase are the same type or different types of polymerases.

In another example of the sixth and seventh aspects, the associated examples, and the above examples, the second polymerase and the third polymerase are the same type or different types of polymerases. For example, the third polymerase and the fourth polymerase are the same type or different types of polymerases.

In a further example of the sixth and seventh aspects, the associated examples, and the above examples, the first, second, third or fourth polymerase is a DNA-dependent polymerase, RNA-dependent polymerase, or reverse transcriptase. For example, the first, second, third or fourth polymerase is a mutant polymerase. In another example, the first, second, third or fourth polymerase has altered nucleotide incorporation kinetics. For example, the altered nucleotide incorporation kinetics includes altered polymerase binding to the target molecule, altered polymerase binding to the nucleotide, altered polymerase catalyzing nucleotide incorporation, altered the polymerase cleaving the phosphate group or substituted phosphate group, or altered polymerase releasing the cleavage product.

In an additional example of the sixth and seventh aspects, the associated examples, and the above examples, the first, second, third or fourth polymerase is linked to an energy transfer donor moiety. For example, the energy transfer donor moiety is a nanoparticle or a fluorescent dye. In a particular example, the nanoparticle is an inorganic fluorescent nanoparticle.

In another example of the sixth and seventh aspects, the associated examples, and the above examples, the at least one target polynucleotide is a single nucleic acid molecule or a plurality of target polynucleotides. For example, the plurality of target polynucleotides comprises a population of nucleic acids having different sequences or having substantially identical sequences.

In a further example of the sixth and seventh aspects, the associated examples, and the above examples, the at least one target polynucleotide is RNA or DNA.

In an additional example of the sixth and seventh aspects, the associated examples, and the above examples, the at least one target polynucleotide or the primer is attached to the device. For example, the at least one target polynucleotide or the primer is attached the transparent layer.

In another example of the sixth and seventh aspects, the associated examples, and the above examples, the at least one target polynucleotide or the primer is attached to a support. For example, the support is a particle or microsphere. In another example, the plurality of nucleic acid molecules have different sequences or have substantially identical sequences.

In a further example of the sixth and seventh aspects, the associated examples, and the above examples, the at least one type of nucleotide comprises one type of nucleotide, or no more than two different types of nucleotides, or no more than three different types of nucleotides, or no more than four different types of nucleotides.

In an additional example of the sixth and seventh aspects, the associated examples, and the above examples, the at least one type of second nucleotide comprises one type of nucleotide, or no more than two different types of nucleotides, or no more than three different types of nucleotides, or no more than four different types of nucleotides.

In another example of the sixth and seventh aspects, the associated examples, and the above examples, the at least one type of nucleotide is adenosine, guanosine, cytosine, thymidine, uridine or inosine.

In a further example of the sixth and seventh aspects, the associated examples, and the above examples, the at least one type of nucleotide is adenosine, guanosine, cytosine, thymidine, uridine or inosine.

In an additional example of the sixth and seventh aspects, the associated examples, and the above examples, the at least one type of nucleotide comprises 3-10 or more phosphate groups.

In another example of the sixth and seventh aspects, the associated examples, and the above examples, the at least one type of nucleotide comprises 3-10 or more phosphate groups. For example, the different types of nucleotides differ from each other in their base, sugar or phosphate backbone.

In a further example of the sixth and seventh aspects, the associated examples, and the above examples, the at least one type of nucleotide comprises a non-incorporatable nucleotide.

In an additional example of the sixth and seventh aspects, the associated examples, and the above examples, the optically detectable moiety is linked to any one of the phosphate groups, the base or the sugar of the at least one type of nucleotide.

In another example of the sixth and seventh aspects, the associated examples, and the above examples, the optically detectable moiety is linked to the nucleotide via a linker that is cleavable with light, a chemical compound or an enzyme. For example, the method further includes removing the optically detectable moiety by cleaving the cleavable linker with light, a chemical compound or an enzyme.

In a further example of the sixth and seventh aspects, the associated examples, and the above examples, the optically detectable moiety is a fluorophore.

In an additional example of the sixth and seventh aspects, the associated examples, and the above examples, the optically detectable signal comprises a fluorescent signal.

In another example of the sixth and seventh aspects, the associated examples, and the above examples, the at least one type of a nucleotide is linked to an optically detectable moiety comprising an energy transfer acceptor moiety.

In a further example of the sixth and seventh aspects, the associated examples, and the above examples, the at least one type of a nucleotide is linked to an energy transfer acceptor moiety and the first, second or third polymerase is linked to an energy transfer donor moiety, and incorporating the at least one type of nucleotide onto the primer, brings the first, second or third polymerase and the at least one type of a nucleotide into close proximity with each other to generate an energy transfer signal. For example, the energy transfer signal comprises a fluorescent signal.

In an additional example of the sixth and seventh aspects, the associated examples, and the above examples, the at least one type of nucleotide is linked to at least one inhibitor moiety that inhibits incorporation of a subsequent nucleotide. For example, the inhibitor moiety is linked to the nucleotide at any position of the base, or any position of the sugar. In another example, the inhibitor moiety is linked to the nucleotide via a linker that is cleavable with light, a chemical compound or an enzyme. For example, the method further includes removing the inhibitor moiety by cleaving the cleavable linker with light, a chemical compound or an enzyme.

In another example of the sixth and seventh aspects, the associated examples, and the above examples, the at least one type of a nucleotide having an optically detectable moiety comprises a mixture of different types of nucleotides containing at least one type of a nucleotide having an optically detectable moiety and at least one type of nucleotide lacking an optically detectable moiety. For example, the mixture of different types of nucleotides includes two, three, four or more different types of nucleotides. In an example, the different nucleotides in the mixture of nucleotides are contacted sequentially with the first, second or third polymerase. For example, the different nucleotides in the mixture of nucleotides are contacted essentially simultaneously with the first, second or third polymerase. In a further example, the mixture of different types of nucleotides includes: (iv) one type of nucleotide having an optically detectable moiety and two or three different types of nucleotides that lack an optically detectable moiety; or (v) two different types of nucleotides having different optically detectable moieties and one or two different types of nucleotides that lack an optically detectable moiety; or (vi) three different types of nucleotides having different optically detectable moieties and one type of nucleotide that lacks an optically detectable moiety. In another example, the mixture of different types of nucleotides includes a non-incorporatable nucleotide.

In a further example of the sixth and seventh aspects, the associated examples, and the above examples, the excitation source is electromagnetic energy. For example, the electromagnetic energy is light.

In an additional example of the sixth and seventh aspects, the associated examples, and the above examples, the device comprises a plurality of sites on the device arranged in an organized or random array.

In another example of the sixth and seventh aspects, the associated examples, and the above examples, the device comprises a plurality of sites on the device arranged in a rectilinear or hexagonal pattern.

In a further example of the sixth and seventh aspects, the associated examples, and the above examples, the method further includes subjecting a plurality of target polynucleotides to the same enzymatic reaction in parallel, wherein the plurality of target polynucleotides comprises a population of nucleic acids having substantially identical sequences or different sequences.

In an example of the sixth and seventh aspects, the associated examples, and the above examples, the target polynucleotide comprises a single nucleic acid molecule.

In an eighth aspect, a method for sequencing a target polynucleotide includes contacting the device of any one of the first, second, or third aspects with an enzymatic reaction, wherein the enzymatic reaction includes: contacting at least one type of a labeled nucleotide to a complex having a first polymerase bound to at least one target polynucleotide that is bound to a primer, under suitable conditions to transiently-bind, without polymerizing, the at least one type of labeled nucleotide to the polymerase in a nucleic acid template-dependent manner; detecting the transiently-bound labeled nucleotide; and identifying the labeled nucleotide transiently-bound to the polymerase, In an example of the eighth aspect, the method further includes removing the transiently-bound nucleotide; and contacting the complex with at least one type of a second nucleotide under suitable conditions for a second polymerase to polymerize the nucleotide.

In another example of the eighth aspect and the above examples, the at least one target polynucleotide comprises a single nucleic acid molecule.

In a further example of the eighth aspect and the above examples, the suitable conditions in the first step include: (i) reducing the levels or omission of a cation that permits nucleotide incorporation or addition of a cation that inhibits nucleotide incorporation; (ii) the polymerase selectively binds the nucleotide in a template-dependent manner and exhibits reduced nucleotide incorporation activity; (iii) the at least one type of labeled nucleotide is a labeled non-incorporatable nucleotide; or (iv) the primer includes a non-extendible polymerization initiation site.

In an additional example of the eighth aspect and the above examples, the suitable conditions in step (a) comprise: (i) cations present at a concentration that inhibits nucleotide incorporation; (ii) the polymerase selectively binds the nucleotide in a template-dependent manner and exhibits reduced nucleotide incorporation activity; (iii) the at least one type of labeled nucleotide is a labeled non-incorporatable nucleotide; or (iv) the primer includes a non-extendible polymerization initiation site. For example, the cation that inhibits nucleotide incorporation is calcium, scandium, titanium, vanadium, chromium, iron, cobalt, nickel, copper, zinc, gallium, germanium, arsenic, selenium, rhodium, or strontium.

In a ninth aspect, a method for nucleic acid sequencing includes contacting the device of any one of the first, second, and third aspects with an enzymatic reaction, wherein the enzymatic reaction includes: transiently binding, without polymerizing, at least a first type of a labeled nucleotide to a first polymerase in the presence of a cation that inhibits nucleotide incorporation by the polymerase, wherein the first polymerase is bound to at least one target polynucleotide that is bound to a primer, and wherein the first type of nucleotide includes an optically detectable moiety; detecting the first type of transiently-bound nucleotide; and identifying the first type of transiently-bound nucleotide, In an example of the ninth aspect, the method further includes removing the transiently-bound first type of nucleotide; and contacting the complex with at least one type of a second nucleotide under suitable conditions for a second polymerase to polymerize the second type of nucleotide in a template-dependent manner.

In another example of the ninth aspect and the above examples, the at least one target polynucleotide comprises a single nucleic acid molecule.

In a further example of the ninth aspect and the above examples, the suitable conditions in the second step further include any one or more of the following: (i) including a cation that permits nucleotide incorporation or reducing the levels or omission of a cation that inhibits nucleotide incorporation; (ii) the first polymerase selectively binds the second type of nucleotide in a template-dependent manner and polymerizes the bound second type of nucleotide; (iii) the second type of nucleotide is an incorporatable nucleotide; and (iv) the primer is an extendible polymerization initiation site. For example, the cation that inhibits nucleotide incorporation is calcium, scandium, titanium, vanadium, chromium, iron, cobalt, nickel, copper, zinc, gallium, germanium, arsenic, selenium, rhodium, or strontium.

In an additional example of the ninth aspect and the above examples, the first and second polymerases are the same polymerase, or different polymerases of the same type, or different types of polymerases.

In another example of the ninth aspect and the above examples, the first or second polymerase is a DNA-dependent polymerase, RNA-dependent polymerase, or reverse transcriptase.

In a further example of the ninth aspect and the above examples, the first or second polymerase is a mutant polymerase.

In an additional example of the ninth aspect and the above examples, the first or second polymerase has altered nucleotide incorporation kinetics. For example, the altered nucleotide incorporation kinetics includes altered polymerase binding to the target molecule, altered polymerase binding to the nucleotide, altered polymerase catalyzing nucleotide incorporation, altered the polymerase cleaving the phosphate group or substituted phosphate group, or altered polymerase releasing the cleavage product.

In another example of the ninth aspect and the above examples, the first or second polymerase comprises an RB69 polymerase, phi29 polymerase, B103 polymerase, or Klenow fragment polymerase.

In a further example of the ninth aspect and the above examples, the first or second polymerase is linked to an energy transfer donor moiety. For example, the energy transfer donor moiety is a nanoparticle or a fluorescent dye. In an example, the nanoparticle is an inorganic fluorescent nanoparticle.

In an additional example of the ninth aspect and the above examples, the at least one target polynucleotide is a single nucleic acid molecule or a plurality of target polynucleotides. For example, the plurality of target polynucleotides comprises a population of nucleic acids having different sequences or having substantially identical sequences.

In another example of the ninth aspect and the above examples, the at least one target polynucleotide is RNA or DNA.

In a further example of the ninth aspect and the above examples, the at least one target polynucleotide or the primer is attached to the device. For example, the at least one target polynucleotide or the primer is attached the transparent layer of the device.

In an additional example of the ninth aspect and the above examples, the at least one target polynucleotide or the primer is attached to a support.

In another example of the ninth aspect and the above examples, the support is a particle or microsphere.

In a further example of the ninth aspect and the above examples, the labeled nucleotide comprises one type of nucleotide, or no more than two different types of nucleotides, or no more than three different types of nucleotides, or no more than four different types of nucleotides.

In an additional example of the ninth aspect and the above examples, the at least one type of second nucleotide comprises one type of nucleotide, or no more than two different types of nucleotides, or no more than three different types of nucleotides, or no more than four different types of nucleotides.

In another example of the ninth aspect and the above examples, the labeled nucleotide is adenosine, guanosine, cytosine, thymidine, uridine or inosine.

In a further example of the ninth aspect and the above examples, at least one type of a second nucleotide is adenosine, guanosine, cytosine, thymidine, uridine or inosine.

In an additional example of the ninth aspect and the above examples, the labeled nucleotide comprises 3-10 or more phosphate groups.

In another example of the ninth aspect and the above examples, at least one type of a second nucleotide comprises 3-10 or more phosphate groups.

In a further example of the ninth aspect and the above examples, the nucleotide comprises a non-incorporatable nucleotide.

In an additional example of the ninth aspect and the above examples, the labeled nucleotide is linked to at least one optically detectable moiety.

In another example of the ninth aspect and the above examples, the at least one type of a second nucleotide is linked to at least one optically detectable moiety In a further example of the ninth aspect and the above examples, the at least one optically detectable moiety is linked to any one of the phosphate groups, the base or the sugar of the nucleotide.

In an additional example of the ninth aspect and the above examples, the optically detectable moiety is linked to the nucleotide via a linker that is cleavable with light, a chemical compound or an enzyme. For example, the optically detectable moiety is a fluorophore. In another example, the optically detectable moiety emits a fluorescent signal. In a further example, the optically detectable moiety comprises an energy transfer acceptor moiety.

In another example of the ninth aspect and the above examples, the labeled nucleotide is linked to an energy transfer acceptor moiety and the first polymerase is linked to an energy transfer donor moiety, and the transient binding the nucleotide to the polymerase brings the first polymerase and the labeled nucleotide in close proximity with each other to generate an energy transfer signal. For example, the energy transfer signal comprises a fluorescent signal.

In a further example of the ninth aspect and the above examples, the labeled nucleotide is linked to at least one inhibitor moiety that inhibits incorporation of a subsequent nucleotide. For example, the inhibitor moiety is linked to the nucleotide at any position of the base or the sugar. In an example, the inhibitor moiety is linked to the nucleotide via a linker that is cleavable with light, a chemical compound or an enzyme.

In an additional example of the ninth aspect and the above examples, the labeled nucleotide comprises a mixture of different types of nucleotides containing at least one type of a nucleotide having an optically detectable moiety and at least one type of nucleotide lacking an optically detectable moiety. For example, the mixture of different types of nucleotides includes two, three, four or more different types of nucleotides. In an example, the different nucleotides in the mixture of nucleotides are contacted sequentially with the first polymerase. In another example, the different nucleotides in the mixture of nucleotides are contacted essentially simultaneously with the first polymerase. In an additional example, the mixture of different types of nucleotides includes: (iv) one type of nucleotide having an optically detectable moiety and two or three different types of nucleotides that lack an optically detectable moiety; or (v) two different types of nucleotides having different optically detectable moieties and one or two different types of nucleotides that lack an optically detectable moiety; or (vi) three different types of nucleotides having different optically detectable moieties and one type of nucleotide that lacks an optically detectable moiety. In a further example, the mixture of different types of nucleotides includes a non-incorporatable nucleotide.

In another example of the ninth aspect and the above examples, the method further includes a) generating an optically detectable signal by exciting the optically detectable moiety with an excitation source; and b) detecting the optically detectable signal. For example, the excitation source is electromagnetic energy. In an example, the electromagnetic energy is light.

In a further example of the ninth aspect and the above examples, the device comprises a plurality of sites on the device arranged in an organized or random array.

In an additional example of the ninth aspect and the above examples, the device comprises a plurality of sites on the device arranged in a rectilinear or hexagonal pattern.

In another example of the ninth aspect and the above examples, the method further includes subjecting a plurality of target polynucleotides to the same enzymatic reaction in parallel, wherein the plurality of target polynucleotides comprises a population of nucleic acids having substantially identical sequences or different sequences.

In an tenth aspect, a method for sequencing a target polynucleotide includes contacting the device of any one of the first, second or third aspects with an enzymatic reaction, wherein the enzymatic reaction includes: forming a reaction mixture containing a polymerase and a target polynucleotide, wherein the reaction mixture includes a concentration of cation at which nucleotide polymerization by the polymerase is inhibited; contacting, within the reaction mixture, a first type of nucleotide containing a detectable moiety with the polymerase and transiently binding the first type of nucleotide to the polymerase in a template-dependent manner without polymerizing the transiently bound nucleotide at the primer by the polymerase; detecting a signal generated by the detectable moiety while the first type of nucleotide is transiently bound to the polymerase; removing the transiently bound nucleotide from the polymerase; and contacting the polymerase with a second type of nucleotide and polymerizing the second type of nucleotide at the primer using the polymerase.

In an example of the tenth aspect, wherein the forming in the first step includes any one or more of the following: (i) reducing the levels or omission of a cation that permits nucleotide incorporation or addition of a cation that inhibits nucleotide incorporation.

In another example of the tenth aspect and the above examples, the suitable conditions in step comprise any one or more of the following: (i) including a cation that permits nucleotide incorporation or reducing the levels or omission of a cation that inhibits nucleotide incorporation; (ii) using a first polymerase which selectively binds the second type of nucleotide in a template-dependent manner and polymerizes the bound second type of nucleotide; (iii) using a second type of nucleotide which includes an incorporatable nucleotide; or (iv) using a primer having an extendible polymerization initiation site In a further example of the tenth aspect and the above examples, the cation that inhibits nucleotide incorporation is calcium, scandium, titanium, vanadium, chromium, iron, cobalt, nickel, copper, zinc, gallium, germanium, arsenic, selenium, rhodium, or strontium.

In an additional example of the tenth aspect and the above examples, the transiently binding in step (b) includes contacting the polymerase with a sufficient amount of a divalent cation to inhibit nucleotide incorporation by the first polymerase. For example, the divalent cation includes calcium.

In another example of the tenth aspect and the above examples, the method further includes repeating the first three steps at least once.

In a further example of the tenth aspect and the above examples, the method includes repeating the fourth and fifth steps at least once.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A device comprising:
   a transparent layer defining a surface exposed to a flow volume and including a plurality of regions, each region to secure a target polynucleotide template; and
   a detector structure in optical communication with the transparent layer and including a plurality of detectors configured to detect a fluorescent signal emitted during nucleotide incorporation during template-dependent nucleic acid synthesis, wherein the detector structure includes a plurality of pixels, each pixel of the plurality of pixels including a set of detectors of the plurality of detectors, the set of detectors disposed in a semiconductor structure, each detector of the set of detectors disposed at a different depth within the semiconductor structure when viewed in cross-section, a detector of the set of detectors overlapping another detector of the set of detectors when viewed in a plan view; wherein a pixel is in optical communication with a region;
   wherein the set of detectors within the semiconductor structure include a p-type substrate, a deep n-type implant, a shallow n-type implant, and a p-type implant disposed over the shallow n-type implant.

2. The device of claim 1, wherein the set of detectors includes at least two detectors.

3. The device of claim 2, wherein each pixel includes at least three detectors.

4. The device of claim 3, wherein each pixel includes at least four detectors.

5. The device of claim 1, wherein the transparent layer includes an energy propagation layer.

6. The device of claim 1, further comprising an energy propagation layer disposed between the transparent layer and the detector structure.

7. The device of claim 6, wherein the energy propagation layer includes a total internal reflection layer.

8. The device of claim 6, further comprising an energy emitting component to provide energy to the energy propagation layer.

9. The device of claim 1, further comprising a separator structure extending from the detector structure toward the transparent layer, the separator structure opaque to the fluorescent signal.

10. The device of claim 1, further comprising a filter layer disposed between the device structure and the transparent layer.

11. The device of claim 10, wherein the filter layer is configured to limit transmission of excitation energy.

12. The device of claim 10, wherein the filter layer is configured to permit the transmission of a wavelength spectrum associated with a dye.

13. The device of claim 1, further comprising a well structure defining wells disposed on the transparent layer opposite the detector structure.

14. The device of claim 1, further comprising a pad structure disposed on the transparent layer opposite the detector structure.

15. The device of claim 1, further comprising a lid, the flow volume defined between the lid and the transparent layer.

16. The device of claim 1, wherein the transparent layer comprises an electrode.

17. An apparatus comprising:
   a transparent layer defining a surface exposed to a flow volume and including a plurality of surface wells, each surface well to secure a target polynucleotide template, the plurality of wells defined by a well structure;
   an energy propagation layer disposed opposite the surface of the transparent layer to propagate photonic energy along a path parallel to the surface;
   an excitation filter layer secured to the energy propagation layer opposite the transparent layer, the excitation filter layer opaque to the photonic energy;
   a microlens layer secured between the excitation filter layer and the detector structure, the microlens layer including a plurality of microlenses, each microlens of the plurality of microlenses aligned between a well of the plurality of wells and a pixel of the plurality of pixels; and
   a detector structure secured to the microlens layer opposite the energy propagation layer, the detector structure defining a plurality of pixels, each pixel including a plurality of detectors, each pixel of the plurality of pixels uniquely optically associated with a well of the plurality of wells, the plurality of detectors disposed in a semiconductor structure, each detector of the plurality of detectors disposed at a different depth within the semiconductor structure when viewed in cross-section, a detector of the plurality of detectors overlapping another detector of the plurality of detectors when viewed in a plan view, wherein the set of detectors in the semiconductor structure include a p-type substrate, a deep n-type implant, a shallow n-type implant, and a p-type implant disposed over the shallow n-type implant.

18. The apparatus of claim 17, wherein each pixel includes at least two detectors.

19. The device of claim 1, wherein the semiconductor structure comprises a silicon substrate, and wherein the each pixel comprises a set of oppositely charged implants disposed in the silicon substrate.

20. The device of claim 1, further comprising circuitry associated with each pixel to selectively detect charge within layers forming the plurality of detectors.

\* \* \* \* \*

SEQUENCE LISTING

<160> NUMBER OF SEQ ID NOS: 14

<210> SEQ ID NO 1
<211> LENGTH: 572
<212> TYPE: PRT
<213> ORGANISM: Bacillus phage B103

<400> SEQUENCE: 1

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ala Glu Arg Pro Val Gly His Glu Ile Thr Pro Glu Glu Tyr
145                 150                 155                 160

Glu Tyr Ile Lys Asn Ala Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Arg Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
        355                 360                 365

```
Thr His Glu Lys Gly Ala Lys Lys Gln Leu Ala Lys Leu Met Leu Asn
    370             375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
                435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Thr Lys Phe Ser Val Lys Cys Ala
                515                 520                 525

Gly Met Thr Asp Thr Ile Lys Lys Lys Val Thr Phe Asp Asn Phe Arg
530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 2
<211> LENGTH: 572
<212> TYPE: PRT
<213> ORGANISM: Bacillus phage B103

<400> SEQUENCE: 2

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
            115                 120                 125

Lys Ile Ala Lys Asp Phe Gln Leu Pro Leu Leu Lys Gly Asp Ile Asp
    130                 135                 140

Tyr His Ala Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175
```

```
Gln Phe Lys Gln Gly Leu Asp Arg Met Thr Ala Gly Ser Asp Ser Leu
                180                 185                 190

Lys Gly Phe Lys Asp Ile Leu Ser Thr Lys Lys Phe Asn Lys Val Phe
            195                 200                 205

Pro Lys Leu Ser Leu Pro Met Asp Lys Glu Ile Arg Arg Ala Tyr Arg
        210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
        355                 360                 365

Thr His Glu Lys Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Lys Phe Ser Val Lys Cys Ala
        515                 520                 525

Gly Met Thr Asp Thr Ile Lys Lys Val Thr Phe Asp Asn Phe Arg
    530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 3
<211> LENGTH: 608
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

Met Ser His His His His His His Ser Met Ser Gly Leu Asn Asp Ile
1               5                   10                  15

Phe Glu Ala Gln Lys Ile Glu Trp His Glu Gly Ala Pro Gly Ala Arg
            20                  25                  30

Gly Ser Lys His Met Pro Arg Lys Met Phe Ser Cys Asp Phe Glu Thr
        35                  40                  45

Thr Thr Lys Leu Asp Asp Cys Arg Val Trp Ala Tyr Gly Tyr Met Glu
    50                  55                  60

Ile Gly Asn Leu Asp Asn Tyr Lys Ile Gly Asn Ser Leu Asp Glu Phe
65                  70                  75                  80

Met Gln Trp Val Met Glu Ile Gln Ala Asp Leu Tyr Phe His Asn Leu
                85                  90                  95

Lys Phe Asp Gly Ala Phe Ile Val Asn Trp Leu Glu His His Gly Phe
            100                 105                 110

Lys Trp Ser Asn Glu Gly Leu Pro Asn Thr Tyr Asn Thr Ile Ile Ser
        115                 120                 125

Lys Met Gly Gln Trp Tyr Met Ile Asp Ile Cys Phe Gly Tyr Lys Gly
    130                 135                 140

Lys Arg Lys Leu His Thr Val Ile Tyr Asp Ser Leu Lys Lys Leu Pro
145                 150                 155                 160

Phe Pro Val Lys Lys Ile Ala Lys Asp Phe Gln Leu Pro Leu Leu Lys
                165                 170                 175

Gly Asp Ile Asp Tyr His Ala Glu Arg Pro Val Gly His Glu Ile Thr
            180                 185                 190

Pro Glu Glu Tyr Glu Tyr Ile Lys Asn Ala Ile Glu Ile Ile Ala Arg
        195                 200                 205

Ala Leu Asp Ile Gln Phe Lys Gln Gly Leu Asp Arg Met Thr Ala Gly
    210                 215                 220

Ser Asp Ser Leu Lys Gly Phe Lys Asp Ile Leu Ser Thr Lys Lys Phe
225                 230                 235                 240

Asn Lys Val Phe Pro Lys Leu Ser Leu Pro Met Asp Lys Glu Ile Arg
                245                 250                 255

Arg Ala Tyr Arg Gly Gly Phe Thr Trp Leu Asn Asp Lys Tyr Lys Glu
            260                 265                 270

Lys Glu Ile Gly Glu Gly Met Val Phe Asp Val Asn Ser Leu Tyr Pro
        275                 280                 285

Ser Gln Met Tyr Ser Arg Pro Leu Pro Tyr Gly Ala Pro Ile Val Phe
    290                 295                 300

Gln Gly Lys Tyr Glu Lys Asp Glu Gln Tyr Pro Leu Tyr Ile Gln Arg
305                 310                 315                 320

Ile Arg Phe Glu Phe Glu Leu Lys Glu Gly Tyr Ile Pro Thr Ile Gln
                325                 330                 335

Ile Lys Lys Asn Pro Phe Phe Lys Gly Asn Glu Tyr Leu Lys Asn Ser
            340                 345                 350

Gly Ala Glu Pro Val Glu Leu Tyr Leu Thr Asn Val Asp Leu Glu Leu
        355                 360                 365

Ile Gln Glu His Tyr Glu Met Tyr Asn Val Glu Tyr Ile Asp Gly Phe
    370                 375                 380

-continued

```
Lys Phe Arg Glu Lys Thr Gly Leu Phe Lys Glu Phe Ile Asp Lys Trp
385                 390                 395                 400

Thr Tyr Val Lys Thr Arg Glu Lys Gly Ala Lys Lys Gln Leu Ala Lys
                405                 410                 415

Leu Met Leu Asn Ser Leu Tyr Gly Lys Phe Ala Ser Asn Pro Asp Val
            420                 425                 430

Thr Gly Lys Val Pro Tyr Leu Lys Glu Asp Gly Ser Leu Gly Phe Arg
        435                 440                 445

Val Gly Asp Glu Glu Tyr Lys Asp Pro Val Tyr Thr Pro Met Gly Val
    450                 455                 460

Phe Ile Thr Ala Trp Ala Arg Phe Thr Thr Ile Thr Ala Ala Gln Ala
465                 470                 475                 480

Cys Tyr Asp Arg Ile Ile Tyr Cys Asp Thr Asp Ser Ile His Leu Thr
                485                 490                 495

Gly Thr Glu Val Pro Glu Ile Ile Lys Asp Ile Val Asp Pro Lys Lys
            500                 505                 510

Leu Gly Tyr Trp Ala His Glu Ser Thr Phe Lys Arg Ala Lys Tyr Leu
        515                 520                 525

Arg Gln Lys Thr Tyr Ile Gln Asp Ile Tyr Ala Lys Glu Val Asp Gly
    530                 535                 540

Lys Leu Ile Glu Cys Ser Pro Asp Glu Ala Thr Thr Thr Lys Phe Ser
545                 550                 555                 560

Val Lys Cys Ala Gly Met Thr Asp Thr Ile Lys Lys Val Thr Phe
                565                 570                 575

Asp Asn Phe Arg Val Gly Phe Ser Ser Thr Gly Lys Pro Lys Pro Val
                580                 585                 590

Gln Val Asn Gly Gly Val Val Leu Val Asp Ser Val Phe Thr Ile Lys
            595                 600                 605

<210> SEQ ID NO 4
<211> LENGTH: 575
<212> TYPE: PRT
<213> ORGANISM: Bacillus phage phi29

<400> SEQUENCE: 4

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
```

-continued

```
            145                 150                 155                 160
        Glu Glu Tyr Ala Tyr Ile Lys Asn Asp Ile Gln Ile Ile Ala Glu Ala
                        165                 170                 175
        Leu Leu Ile Gln Phe Lys Gln Gly Leu Asp Arg Met Thr Ala Gly Ser
                        180                 185                 190
        Asp Ser Leu Lys Gly Phe Lys Asp Ile Ile Thr Thr Lys Lys Phe Lys
                        195                 200                 205
        Lys Val Phe Pro Thr Leu Ser Leu Gly Leu Asp Lys Glu Val Arg Tyr
                210                 215                 220
        Ala Tyr Arg Gly Gly Phe Thr Trp Leu Asn Asp Arg Phe Lys Glu Lys
        225                 230                 235                 240
        Glu Ile Gly Glu Gly Met Val Phe Asp Val Asn Ser Leu Tyr Pro Ala
                        245                 250                 255
        Gln Met Tyr Ser Arg Leu Leu Pro Tyr Gly Glu Pro Ile Val Phe Glu
                        260                 265                 270
        Gly Lys Tyr Val Trp Asp Glu Asp Tyr Pro Leu His Ile Gln His Ile
                        275                 280                 285
        Arg Cys Glu Phe Glu Leu Lys Glu Gly Tyr Ile Pro Thr Ile Gln Ile
                        290                 295                 300
        Lys Arg Ser Arg Phe Tyr Lys Gly Asn Glu Tyr Leu Lys Ser Ser Gly
        305                 310                 315                 320
        Gly Glu Ile Ala Asp Leu Trp Leu Ser Asn Val Asp Leu Glu Leu Met
                        325                 330                 335
        Lys Glu His Tyr Asp Leu Tyr Asn Val Glu Tyr Ile Ser Gly Leu Lys
                        340                 345                 350
        Phe Lys Ala Thr Thr Gly Leu Phe Lys Asp Phe Ile Asp Lys Trp Thr
                        355                 360                 365
        Tyr Ile Lys Thr Thr Ser Glu Gly Ala Ile Lys Gln Leu Ala Lys Leu
                        370                 375                 380
        Met Leu Asn Ser Leu Tyr Gly Lys Phe Ala Ser Asn Pro Asp Val Thr
        385                 390                 395                 400
        Gly Lys Val Pro Tyr Leu Lys Glu Asn Gly Ala Leu Gly Phe Arg Leu
                        405                 410                 415
        Gly Glu Glu Glu Thr Lys Asp Pro Val Tyr Thr Pro Met Gly Val Phe
                        420                 425                 430
        Ile Thr Ala Trp Ala Arg Tyr Thr Thr Ile Thr Ala Ala Gln Ala Cys
                        435                 440                 445
        Tyr Asp Arg Ile Ile Tyr Cys Asp Thr Asp Ser Ile His Leu Thr Gly
        450                 455                 460
        Thr Glu Ile Pro Asp Val Ile Lys Asp Ile Val Asp Pro Lys Lys Leu
        465                 470                 475                 480
        Gly Tyr Trp Ala His Glu Ser Thr Phe Lys Arg Ala Lys Tyr Leu Arg
                        485                 490                 495
        Gln Lys Thr Tyr Ile Gln Asp Ile Tyr Met Lys Glu Val Asp Gly Lys
                        500                 505                 510
        Leu Val Glu Gly Ser Pro Asp Asp Tyr Thr Asp Ile Lys Phe Ser Val
                        515                 520                 525
        Lys Cys Ala Gly Met Thr Asp Lys Ile Lys Lys Glu Val Thr Phe Glu
                        530                 535                 540
        Asn Phe Lys Val Gly Phe Ser Arg Lys Met Lys Pro Lys Pro Val Gln
        545                 550                 555                 560
        Val Pro Gly Gly Val Val Leu Val Asp Asp Thr Phe Thr Ile Lys
                        565                 570                 575
```

<210> SEQ ID NO 5
<211> LENGTH: 600
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Asn His Leu Val His His His His His Ile Glu Gly Arg His
1               5                   10                  15

Met Glu Leu Gly Thr Leu Glu Gly Ser Met Lys His Met Pro Arg Lys
            20                  25                  30

Met Tyr Ser Cys Ala Phe Glu Thr Thr Thr Lys Val Glu Asp Cys Arg
        35                  40                  45

Val Trp Ala Tyr Gly Tyr Met Asn Ile Glu Asp His Ser Glu Tyr Lys
    50                  55                  60

Ile Gly Asn Ser Leu Asp Glu Phe Met Ala Trp Val Leu Lys Val Gln
65                  70                  75                  80

Ala Asp Leu Tyr Phe His Asn Leu Lys Phe Ala Gly Ala Phe Ile Ile
                85                  90                  95

Asn Trp Leu Glu Arg Asn Gly Phe Lys Trp Ser Ala Asp Gly Leu Pro
            100                 105                 110

Asn Thr Tyr Asn Thr Ile Ile Ser Arg Met Gly Gln Trp Tyr Met Ile
        115                 120                 125

Asp Ile Cys Leu Gly Tyr Lys Gly Lys Arg Lys Ile His Thr Val Ile
    130                 135                 140

Tyr Asp Ser Leu Lys Lys Leu Pro Phe Pro Val Lys Lys Ile Ala Lys
145                 150                 155                 160

Asp Phe Lys Leu Thr Val Leu Lys Gly Asp Ile Asp Tyr His Lys Glu
                165                 170                 175

Arg Pro Val Gly Tyr Lys Ile Thr Pro Glu Glu Tyr Ala Tyr Ile Lys
            180                 185                 190

Asn Asp Ile Gln Ile Ile Ala Glu Ala Leu Leu Ile Gln Phe Lys Gln
        195                 200                 205

Gly Leu Asp Arg Met Thr Ala Gly Ser Asp Ser Leu Lys Gly Phe Lys
    210                 215                 220

Asp Ile Ile Thr Thr Lys Lys Phe Lys Lys Val Phe Pro Thr Leu Ser
225                 230                 235                 240

Leu Gly Leu Asp Lys Glu Val Arg Tyr Ala Tyr Arg Gly Gly Phe Thr
                245                 250                 255

Trp Leu Asn Asp Arg Phe Lys Glu Lys Glu Ile Gly Glu Gly Met Val
            260                 265                 270

Phe Asp Val Asn Ser Leu Tyr Pro Ala Gln Met Tyr Ser Arg Leu Leu
        275                 280                 285

Pro Tyr Gly Glu Pro Ile Val Phe Glu Gly Lys Tyr Val Trp Asp Glu
    290                 295                 300

Asp Tyr Pro Leu His Ile Gln His Ile Arg Cys Glu Phe Glu Leu Lys
305                 310                 315                 320

Glu Gly Tyr Ile Pro Thr Ile Gln Ile Lys Arg Ser Arg Phe Tyr Lys
                325                 330                 335

Gly Asn Glu Tyr Leu Lys Ser Ser Gly Gly Glu Ile Ala Asp Leu Trp
            340                 345                 350

Leu Ser Asn Val Asp Leu Glu Leu Met Lys Glu His Tyr Asp Leu Tyr
```

```
        355                 360                 365
Asn Val Glu Tyr Ile Ser Gly Leu Lys Phe Lys Ala Thr Thr Gly Leu
370                 375                 380

Phe Lys Asp Phe Ile Asp Lys Trp Thr Tyr Ile Lys Thr Thr Ser Glu
385                 390                 395                 400

Gly Ala Ile Lys Ala Leu Ala Lys Leu Met Leu Asn Ser Leu Tyr Gly
                405                 410                 415

Lys Phe Ala Ser Asn Pro Asp Val Thr Gly Lys Val Pro Tyr Leu Lys
                420                 425                 430

Glu Asn Gly Ala Leu Gly Phe Arg Leu Gly Glu Glu Thr Lys Asp
                435                 440                 445

Pro Val Tyr Thr Pro Met Gly Val Phe Ile Thr Ala Trp Ala Arg Tyr
                450                 455                 460

Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Ile Pro Asp Val Ile
                485                 490                 495

Lys Asp Ile Val Asp Pro Lys Lys Leu Gly Tyr Trp Ala His Glu Ser
                500                 505                 510

Thr Phe Lys Arg Ala Lys Tyr Leu Arg Gln Lys Thr Tyr Ile Gln Asp
                515                 520                 525

Ile Tyr Met Lys Glu Val Asp Gly Lys Leu Val Glu Gly Ser Pro Asp
530                 535                 540

Asp Tyr Thr Asp Ile Lys Phe Ser Val Lys Cys Ala Gly Met Thr Asp
545                 550                 555                 560

Lys Ile Lys Lys Glu Val Thr Phe Glu Asn Phe Lys Val Gly Phe Ser
                565                 570                 575

Arg Lys Met Lys Pro Lys Pro Val Gln Val Pro Gly Gly Val Val Leu
                580                 585                 590

Val Asp Asp Thr Phe Thr Ile Lys
                595                 600

<210> SEQ ID NO 6
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asn His Leu Val His His His His His Ile Glu Gly Arg His
1               5                   10                  15

Met Glu Leu Gly Thr Leu Glu Gly Ser Met Lys His Met Pro Arg Lys
                20                  25                  30

Met Tyr Ser Cys Ala Phe Glu Thr Thr Thr Lys Val Glu Asp Cys Arg
            35                  40                  45

Val Trp Ala Tyr Gly Tyr Met Asn Ile Glu Asp His Ser Glu Tyr Lys
        50                  55                  60

Ile Gly Asn Ser Leu Asp Glu Phe Met Ala Trp Val Leu Lys Val Gln
65                  70                  75                  80

Ala Asp Leu Tyr Phe His Asn Leu Lys Phe Ala Gly Ala Phe Ile Ile
                85                  90                  95

Asn Trp Leu Glu Arg Asn Gly Phe Lys Trp Ser Ala Asp Gly Leu Pro
                100                 105                 110
```

```
Asn Thr Tyr Asn Thr Ile Ile Ser Arg Met Gly Gln Trp Tyr Met Ile
            115                 120                 125

Asp Ile Cys Leu Gly Tyr Lys Gly Lys Arg Lys Ile His Thr Val Ile
    130                 135                 140

Tyr Asp Ser Leu Lys Lys Leu Pro Phe Pro Val Lys Lys Ile Ala Lys
145                 150                 155                 160

Asp Phe Lys Leu Thr Val Leu Lys Gly Asp Ile Asp Tyr His Lys Glu
                165                 170                 175

Arg Pro Val Gly Tyr Lys Ile Thr Pro Glu Glu Tyr Ala Tyr Ile Lys
            180                 185                 190

Asn Asp Ile Gln Ile Ile Ala Glu Ala Leu Leu Ile Gln Phe Lys Gln
            195                 200                 205

Gly Leu Asp Arg Met Thr Ala Gly Ser Asp Ser Leu Lys Gly Phe Lys
210                 215                 220

Asp Ile Ile Thr Thr Lys Lys Phe Lys Lys Val Phe Pro Thr Leu Ser
225                 230                 235                 240

Leu Gly Leu Asp Lys Glu Val Arg Tyr Ala Tyr Arg Gly Gly Phe Thr
                245                 250                 255

Trp Leu Asn Asp Arg Phe Lys Glu Lys Glu Ile Gly Glu Gly Met Val
            260                 265                 270

Phe Asp Val Asn Ser Leu Tyr Pro Ala Gln Met Tyr Ser Arg Leu Leu
            275                 280                 285

Pro Tyr Gly Glu Pro Ile Val Phe Glu Gly Lys Tyr Val Trp Asp Glu
            290                 295                 300

Asp Tyr Pro Leu His Ile Gln His Ile Arg Cys Glu Phe Glu Leu Lys
305                 310                 315                 320

Glu Gly Tyr Ile Pro Thr Ile Gln Ile Lys Arg Ser Arg Phe Tyr Lys
                325                 330                 335

Gly Asn Glu Tyr Leu Lys Ser Ser Gly Gly Glu Ile Ala Asp Leu Trp
            340                 345                 350

Leu Ser Asn Val Asp Leu Glu Leu Met Lys Glu His Tyr Asp Leu Tyr
            355                 360                 365

Asn Val Glu Tyr Ile Ser Gly Leu Lys Phe Lys Ala Thr Thr Gly Leu
370                 375                 380

Phe Lys Asp Phe Ile Asp Lys Trp Thr Tyr Ile Lys Thr Thr Ser Glu
385                 390                 395                 400

Gly Ala Ile Lys Gln Leu Ala Lys Leu Met Leu Asn Gly Leu Tyr Gly
                405                 410                 415

Lys Phe Ala Ser Asn Pro Asp Val Thr Gly Lys Val Pro Tyr Leu Lys
            420                 425                 430

Glu Asn Gly Ala Leu Gly Phe Arg Leu Gly Glu Glu Thr Lys Asp
            435                 440                 445

Pro Val Tyr Thr Pro Met Gly Val Phe Ile Thr Ala Trp Ala Arg Tyr
    450                 455                 460

Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Ile Pro Asp Val Ile
                485                 490                 495

Lys Asp Ile Val Asp Pro Lys Lys Leu Gly Tyr Trp Ala His Glu Ser
            500                 505                 510

Thr Phe Lys Arg Ala Lys Tyr Leu Arg Gln Lys Thr Tyr Ile Gln Asp
            515                 520                 525

Ile Tyr Met Lys Glu Val Asp Gly Lys Leu Val Glu Gly Ser Pro Asp
```

```
            530                 535                 540
Asp Tyr Thr Asp Ile Lys Phe Ser Val Lys Cys Ala Gly Met Thr Asp
545                 550                 555                 560

Lys Ile Lys Lys Glu Val Thr Phe Glu Asn Phe Lys Val Gly Phe Ser
                565                 570                 575

Arg Lys Met Lys Pro Lys Pro Val Gln Val Pro Gly Gly Val Val Leu
                580                 585                 590

Val Asp Asp Thr Phe Thr Ile Lys
                595                 600

<210> SEQ ID NO 7
<211> LENGTH: 903
<212> TYPE: PRT
<213> ORGANISM: Unknown
<220> FEATURE:
<223> OTHER INFORMATION: Description of Unknown: Enterobacteria phage
      RB69 polypeptide

<400> SEQUENCE: 7

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
                20                  25                  30

Tyr Lys Pro Ser Leu Phe Ala His Cys Pro Glu Ser Gln Ala Thr Lys
            35                  40                  45

Tyr Phe Asp Ile Tyr Gly Lys Pro Cys Thr Arg Lys Leu Phe Ala Asn
        50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Asp Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285
```

-continued

```
Ser Leu Asp Tyr Ile Ser Glu Phe Glu Leu Asn Val Gly Lys Leu Lys
    290                 295                 300

Tyr Asp Gly Pro Ile Ser Lys Leu Arg Glu Ser Asn His Gln Arg Tyr
305                 310                 315                 320

Ile Ser Tyr Asn Ile Ile Asp Val Tyr Arg Val Leu Gln Ile Asp Ala
                325                 330                 335

Lys Arg Gln Phe Ile Asn Leu Ser Leu Asp Met Gly Tyr Tyr Ala Lys
            340                 345                 350

Ile Gln Ile Gln Ser Val Phe Ser Pro Ile Lys Thr Trp Asp Ala Ile
        355                 360                 365

Ile Phe Asn Ser Leu Lys Glu Gln Asn Lys Val Ile Pro Gln Gly Arg
370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
                405                 410                 415

Pro Ser Ile Ile Arg Gln Val Asn Ile Ser Pro Glu Thr Ile Ala Gly
            420                 425                 430

Thr Phe Lys Val Ala Pro Leu His Asp Tyr Ile Asn Ala Val Ala Glu
        435                 440                 445

Arg Pro Ser Asp Val Tyr Ser Cys Ser Pro Asn Gly Met Met Tyr Tyr
450                 455                 460

Lys Asp Arg Asp Gly Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
            500                 505                 510

Pro Leu Asp Val Asp Tyr Arg Phe Asp Phe Ser Asp Glu Ile Lys Glu
        515                 520                 525

Lys Ile Lys Lys Leu Ser Ala Lys Ser Leu Asn Glu Met Leu Phe Arg
530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
        595                 600                 605

Cys Gly Thr Glu Gly Glu Ala Phe Val Leu Tyr Gly Asp Thr Asp Ser
610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
        675                 680                 685

Ala Gly Pro Pro Leu Gly Ser Lys Gly Ile Gly Gly Phe Trp Thr Gly
690                 695                 700

Lys Lys Arg Tyr Ala Leu Asn Val Trp Asp Met Glu Gly Thr Arg Tyr
```

```
                705                 710                 715                 720
Ala Glu Pro Lys Leu Lys Ile Met Gly Leu Glu Thr Gln Lys Ser Ser
                    725                 730                 735

Thr Pro Lys Ala Val Gln Lys Ala Leu Lys Glu Cys Ile Arg Arg Met
            740                 745                 750

Leu Gln Glu Gly Glu Ser Leu Gln Glu Tyr Phe Lys Glu Phe Glu
                755                 760                 765

Lys Glu Phe Arg Gln Leu Asn Tyr Ile Ser Ile Ala Ser Val Ser Ser
            770                 775                 780

Ala Asn Asn Ile Ala Lys Tyr Asp Val Gly Phe Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Lys Val Tyr Val
                820                 825                 830

Leu Pro Leu Arg Glu Gly Asn Pro Phe Gly Asp Lys Cys Ile Ala Trp
            835                 840                 845

Pro Ser Gly Thr Glu Ile Thr Asp Leu Ile Lys Asp Val Leu His
            850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
                900
```

<210> SEQ ID NO 8
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
                20                  25                  30

Tyr Lys Pro Ser Leu Phe Ala His Cys Pro Glu Ser Gln Ala Thr Lys
            35                  40                  45

Tyr Phe Asp Ile Tyr Gly Lys Pro Cys Thr Arg Lys Leu Phe Ala Asn
        50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
                100                 105                 110

Phe Asp Ile Glu Val Thr Ser Pro Asp Gly Phe Pro Glu Pro Ser Gln
            115                 120                 125

Ala Lys His Pro Ile Asp Ala Ile Thr His Tyr Asp Ser Ile Asp Asp
        130                 135                 140

Arg Phe Tyr Val Phe Asp Leu Leu Asn Ser Pro Tyr Gly Asn Val Glu
145                 150                 155                 160
```

-continued

Glu Trp Ser Ile Glu Ile Ala Ala Lys Leu Gln Glu Gln Gly Gly Asp
              165                 170                 175
Glu Val Pro Ser Glu Ile Ile Asp Lys Ile Ile Tyr Met Pro Phe Asp
          180                 185                 190
Asn Glu Lys Glu Leu Leu Met Glu Tyr Leu Asn Phe Trp Gln Gln Lys
          195                 200                 205
Thr Pro Val Ile Leu Thr Gly Trp Asn Val Glu Ser Phe Ala Ile Pro
      210                 215                 220
Tyr Val Tyr Asn Arg Ile Lys Asn Ile Phe Gly Glu Ser Thr Ala Lys
225                 230                 235                 240
Arg Leu Ser Pro His Arg Lys Thr Arg Val Lys Val Ile Glu Asn Met
              245                 250                 255
Tyr Gly Ser Arg Glu Ile Ile Thr Leu Phe Gly Ile Ser Val Leu Asp
              260                 265                 270
Tyr Ile Asp Leu Tyr Lys Lys Phe Ser Phe Thr Asn Gln Pro Ser Tyr
      275                 280                 285
Ser Leu Asp Tyr Ile Ser Glu Phe Glu Leu Asn Val Gly Lys Leu Lys
          290                 295                 300
Tyr Asp Gly Pro Ile Ser Lys Leu Arg Glu Ser Asn His Gln Arg Tyr
305                 310                 315                 320
Ile Ser Tyr Asn Ile Ile Ala Val Tyr Arg Val Leu Gln Ile Asp Ala
              325                 330                 335
Lys Arg Gln Phe Ile Asn Leu Ser Leu Asp Met Gly Tyr Tyr Ala Lys
              340                 345                 350
Ile Gln Ile Gln Ser Val Phe Ser Pro Ile Lys Thr Trp Asp Ala Ile
          355                 360                 365
Ile Phe Asn Ser Leu Lys Glu Gln Asn Lys Val Ile Pro Gln Gly Arg
      370                 375                 380
Ser His Pro Val Gln Pro Tyr Pro Gly Ala Phe Val Lys Glu Pro Ile
385                 390                 395                 400
Pro Asn Arg Tyr Lys Tyr Val Met Ser Phe Asp Leu Thr Ser Ser Ala
              405                 410                 415
Val Ser Ile Ile Arg Gln Val Asn Ile Ser Pro Glu Thr Ile Ala Gly
              420                 425                 430
Thr Phe Lys Val Ala Pro Leu His Asp Tyr Ile Asn Ala Val Ala Glu
          435                 440                 445
Arg Pro Ser Asp Val Tyr Ser Cys Ser Pro Asn Gly Met Met Tyr Tyr
      450                 455                 460
Lys Asp Arg Asp Gly Val Val Pro Thr Glu Ile Thr Lys Val Phe Asn
465                 470                 475                 480
Gln Arg Lys Glu His Lys Gly Tyr Met Leu Ala Ala Gln Arg Asn Gly
              485                 490                 495
Glu Ile Ile Lys Glu Ala Leu His Asn Pro Asn Leu Ser Val Asp Glu
          500                 505                 510
Pro Leu Asp Val Asp Tyr Arg Phe Asp Phe Ser Asp Glu Ile Lys Glu
      515                 520                 525
Lys Ile Lys Lys Leu Ser Ala Lys Ser Leu Asn Glu Met Leu Phe Arg
530                 535                 540
Ala Gln Arg Thr Glu Val Ala Gly Met Thr Ala Gln Ile Asn Arg Lys
545                 550                 555                 560
Leu Leu Ile Asn Ser Leu Tyr Gly Ala Leu Gly Asn Val Trp Phe Arg
              565                 570                 575
Tyr Tyr Asp Leu Arg Asn Ala Thr Ala Ile Thr Thr Phe Gly Gln Met

```
            580                 585                 590
Ala Leu Gln Trp Ile Glu Arg Lys Val Asn Glu Tyr Leu Asn Glu Val
        595                 600                 605

Cys Gly Thr Glu Gly Glu Ala Phe Val Leu Tyr Gly Asp Thr Asp Ser
        610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
        675                 680                 685

Ala Gly Pro Pro Leu Gly Ser Lys Gly Ile Gly Gly Phe Trp Thr Gly
        690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735

Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
        755                 760                 765

Lys Glu Phe Arg Gln Leu Asn Tyr Ile Ser Ile Ala Ser Val Ser Ser
        770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Glu Lys Val Tyr Val
            820                 825                 830

Leu Pro Leu Arg Glu Gly Asn Pro Phe Gly Asp Lys Cys Ile Ala Trp
        835                 840                 845

Pro Ser Gly Thr Glu Ile Thr Asp Leu Ile Lys Asp Asp Val Leu His
        850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
            900
```

```
<210> SEQ ID NO 9
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30
```

```
Tyr Lys Pro Ser Leu Phe Ala His Cys Pro Glu Ser Gln Ala Thr Lys
         35                  40                  45

Tyr Phe Asp Ile Tyr Gly Lys Pro Cys Thr Arg Lys Leu Phe Ala Asn
 50                  55                  60

Met Arg Asp Ala Ser Gln Trp Ile Lys Arg Met Glu Asp Ile Gly Leu
 65                  70                  75                  80

Glu Ala Leu Gly Met Asp Asp Phe Lys Leu Ala Tyr Leu Ser Asp Thr
                 85                  90                  95

Tyr Asn Tyr Glu Ile Lys Tyr Asp His Thr Lys Ile Arg Val Ala Asn
                100                 105                 110

Phe Asp Ile Glu Val Thr Ser Pro Asp Gly Phe Pro Glu Pro Ser Gln
             115                 120                 125

Ala Lys His Pro Ile Asp Ala Ile Thr His Tyr Asp Ser Ile Asp Asp
 130                 135                 140

Arg Phe Tyr Val Phe Asp Leu Leu Asn Ser Pro Tyr Gly Asn Val Glu
 145                 150                 155                 160

Glu Trp Ser Ile Glu Ile Ala Ala Lys Leu Gln Glu Gln Gly Gly Asp
                 165                 170                 175

Glu Val Pro Ser Glu Ile Ile Asp Lys Ile Ile Tyr Met Pro Phe Asp
             180                 185                 190

Asn Glu Lys Glu Leu Leu Met Glu Tyr Leu Asn Phe Trp Gln Gln Lys
                 195                 200                 205

Thr Pro Val Ile Leu Thr Gly Trp Asn Val Glu Ser Phe Asp Ile Pro
         210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                 245                 250                 255

Tyr Gly Ser Arg Glu Ile Ile Thr Leu Phe Gly Ile Ser Val Leu Asp
             260                 265                 270

Tyr Ile Asp Leu Tyr Lys Lys Phe Ser Phe Thr Asn Gln Pro Ser Tyr
         275                 280                 285

Ser Leu Asp Tyr Ile Ser Glu Phe Glu Leu Asn Val Gly Lys Leu Lys
         290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                 325                 330                 335

Lys Arg Gln Phe Ile Asn Leu Ser Leu Asp Met Gly Tyr Tyr Ala Lys
                 340                 345                 350

Ile Gln Ile Gln Ser Val Phe Ser Pro Ile Lys Thr Trp Asp Ala Ile
             355                 360                 365

Ile Phe Asn Ser Leu Lys Glu Gln Asn Lys Val Ile Pro Gln Gly Arg
         370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
                 405                 410                 415

Pro Ser Ile Ile Arg Gln Val Asn Ile Ser Pro Glu Thr Ile Ala Gly
             420                 425                 430

Thr Phe Lys Val Ala Pro Leu His Asp Tyr Ile Asn Ala Val Ala Glu
         435                 440                 445

Arg Pro Ser Asp Val Tyr Ser Cys Ser Pro Asn Gly Met Met Tyr Tyr
```

-continued

```
            450                 455                 460
Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
                500                 505                 510

Pro Leu Asp Val Asp Tyr Arg Phe Asp Phe Ser Asp Glu Ile Lys Glu
                515                 520                 525

Lys Ile Lys Lys Leu Ser Ala Lys Ser Leu Asn Glu Met Leu Phe Arg
530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
                580                 585                 590

Ala Leu Gln Trp Ile Glu Arg Lys Val Asn Glu Tyr Leu Asn Glu Val
                595                 600                 605

Cys Gly Thr Glu Gly Glu Ala Phe Val Leu Tyr Gly Asp Thr Asp Ser
                610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                        645                 650                 655

Glu Arg Met Glu Pro Ala Ile Asp Arg Gly Phe Arg Glu Met Cys Glu
                660                 665                 670

Tyr Met Asn Asn Lys Gln His Leu Met Phe Met Asp Arg Glu Ala Ile
                675                 680                 685

Ala Gly Pro Pro Leu Gly Ser Lys Gly Ile Gly Gly Phe Trp Thr Gly
                690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735

Thr Pro Lys Ala Val Gln Lys Ala Leu Lys Glu Cys Ile Arg Arg Met
                740                 745                 750

Leu Gln Glu Gly Glu Glu Ser Leu Gln Glu Tyr Phe Lys Glu Phe Glu
                755                 760                 765

Lys Glu Phe Arg Gln Leu Asn Tyr Ile Ser Ile Ala Ser Val Ser Ser
                770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Glu Lys Val Tyr Val
                820                 825                 830

Leu Pro Leu Arg Glu Gly Asn Pro Phe Gly Asp Lys Cys Ile Ala Trp
                835                 840                 845

Pro Ser Gly Thr Glu Ile Thr Asp Leu Ile Lys Asp Asp Val Leu His
                850                 855                 860

Trp Met Asp Tyr Thr Val Leu Leu Glu Lys Thr Phe Ile Lys Pro Leu
865                 870                 875                 880
```

Glu Gly Phe Thr Ser Ala Ala Lys Leu Asp Tyr Glu Lys Lys Ala Ser
            885                 890                 895

Leu Phe Asp Met Phe Asp Phe
            900

<210> SEQ ID NO 10
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
                20                  25                  30

Tyr Lys Pro Ser Leu Phe Ala His Cys Pro Glu Ser Gln Ala Thr Lys
            35                  40                  45

Tyr Phe Asp Ile Tyr Gly Lys Pro Cys Thr Arg Lys Leu Phe Ala Asn
        50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Ala Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala

-continued

```
                325                 330                 335
Lys Arg Gln Phe Ile Asn Leu Ser Leu Asp Met Gly Tyr Tyr Ala Lys
            340                 345                 350
Ile Gln Ile Gln Ser Val Phe Ser Pro Ile Lys Thr Trp Asp Ala Ile
            355                 360                 365
Ile Phe Asn Ser Leu Lys Glu Gln Asn Lys Val Ile Pro Gln Gly Arg
            370                 375                 380
Ser His Pro Val Gln Pro Tyr Pro Gly Ala Phe Val Lys Glu Pro Ile
385                 390                 395                 400
Pro Asn Arg Tyr Lys Tyr Val Met Ser Phe Asp Leu Thr Ser Leu Tyr
                405                 410                 415
Pro Ser Ile Ile Arg Gln Val Asn Ile Ser Pro Glu Thr Ile Ala Gly
                420                 425                 430
Thr Phe Lys Val Ala Pro Leu His Asp Tyr Ile Asn Ala Val Ala Glu
            435                 440                 445
Arg Pro Ser Asp Val Tyr Ser Cys Ser Pro Asn Gly Met Met Tyr Tyr
            450                 455                 460
Lys Asp Arg Asp Gly Val Val Pro Thr Glu Ile Thr Lys Val Phe Asn
465                 470                 475                 480
Gln Arg Lys Glu His Lys Gly Tyr Met Leu Ala Ala Gln Arg Asn Gly
                485                 490                 495
Glu Ile Ile Lys Glu Ala Leu His Asn Pro Asn Leu Ser Val Asp Glu
                500                 505                 510
Pro Leu Asp Val Asp Tyr Arg Phe Asp Phe Ser Asp Glu Ile Lys Glu
            515                 520                 525
Lys Ile Lys Lys Leu Ser Ala Lys Ser Leu Asn Glu Met Leu Phe Arg
530                 535                 540
Ala Gln Arg Thr Glu Val Ala Gly Met Thr Ala Gln Ile Asn Arg Lys
545                 550                 555                 560
Leu Leu Ile Asn Ser Leu Tyr Gly Ala Leu Gly Asn Val Trp Phe Arg
                565                 570                 575
Tyr Tyr Asp Leu Arg Asn Ala Thr Ala Ile Thr Thr Phe Gly Gln Met
            580                 585                 590
Ala Leu Gln Trp Ile Glu Arg Lys Val Asn Glu Tyr Leu Asn Glu Val
            595                 600                 605
Cys Gly Thr Glu Gly Glu Ala Phe Val Leu Tyr Gly Asp Thr Asp Ser
            610                 615                 620
Ile Tyr Val Ser Ala Asp Lys Ile Ile Asp Lys Val Gly Glu Ser Lys
625                 630                 635                 640
Phe Arg Asp Thr Asn His Trp Val Asp Phe Leu Asp Lys Phe Ala Arg
                645                 650                 655
Glu Arg Met Glu Pro Ala Ile Asp Arg Gly Phe Arg Glu Met Cys Glu
            660                 665                 670
Tyr Met Asn Asn Lys Gln His Leu Met Phe Met Asp Arg Glu Ala Ile
            675                 680                 685
Ala Gly Pro Pro Leu Gly Ser Lys Gly Ile Gly Gly Phe Trp Thr Gly
            690                 695                 700
Lys Lys Arg Tyr Ala Leu Asn Val Trp Asp Met Glu Gly Thr Arg Tyr
705                 710                 715                 720
Ala Glu Pro Lys Leu Lys Ile Met Gly Leu Glu Thr Gln Lys Ser Ser
                725                 730                 735
Thr Pro Lys Ala Val Gln Lys Ala Leu Lys Glu Cys Ile Arg Arg Met
            740                 745                 750
```

```
Leu Gln Glu Gly Glu Glu Ser Leu Gln Glu Tyr Phe Lys Glu Phe
        755                 760                 765

Lys Glu Phe Arg Gln Leu Asn Tyr Ile Ser Ile Ala Ser Val Ser Ser
    770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Lys Val Tyr Val
                820                 825                 830

Leu Pro Leu Arg Glu Gly Asn Pro Phe Gly Asp Lys Cys Ile Ala Trp
                835                 840                 845

Pro Ser Gly Thr Glu Ile Thr Asp Leu Ile Lys Asp Val Leu His
        850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
            900

<210> SEQ ID NO 11
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
```

```
            195                 200                 205
Thr Pro Val Ile Leu Thr Gly Trp Asn Val Glu Ser Phe Ala Ile Pro
210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                    245                 250                 255

Tyr Gly Ser Arg Glu Ile Ile Thr Leu Phe Gly Ile Ser Val Leu Asp
                260                 265                 270

Tyr Ile Asp Leu Tyr Lys Lys Phe Ser Phe Thr Asn Gln Pro Ser Tyr
                275                 280                 285

Ser Leu Asp Tyr Ile Ser Glu Phe Glu Leu Asn Val Gly Lys Leu Lys
290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                    325                 330                 335

Lys Arg Gln Phe Ile Asn Leu Ser Leu Asp Met Gly Tyr Tyr Ala Lys
                340                 345                 350

Ile Gln Ile Gln Ser Val Phe Ser Pro Ile Lys Thr Trp Asp Ala Ile
                355                 360                 365

Ile Phe Asn Ser Leu Lys Glu Gln Asn Lys Val Ile Pro Gln Gly Arg
370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
                    405                 410                 415

Pro Ser Ile Ile Arg Gln Val Asn Ile Ser Pro Glu Thr Ile Ala Gly
                420                 425                 430

Thr Phe Lys Val Ala Pro Leu His Asp Tyr Ile Asn Ala Val Ala Glu
                435                 440                 445

Arg Pro Ser Asp Val Tyr Ser Cys Ser Pro Asn Gly Met Met Tyr Tyr
                450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                    485                 490                 495

Glu Ile Ile Lys Glu Ala Leu His Asn Pro Asn Leu Ser Val Asp Glu
                500                 505                 510

Pro Leu Asp Val Asp Tyr Arg Phe Asp Phe Ser Asp Glu Ile Lys Glu
                515                 520                 525

Lys Ile Lys Lys Leu Ser Ala Lys Ser Leu Asn Glu Met Leu Phe Arg
530                 535                 540

Ala Gln Arg Thr Glu Val Ala Gly Met Thr Ala Gln Ile Leu Arg Lys
545                 550                 555                 560

Leu Leu Ile Asn Ser Leu Tyr Gly Ala Leu Gly Asn Val Trp Phe Arg
                    565                 570                 575

Tyr Tyr Asp Leu Arg Asn Ala Thr Ala Ile Thr Thr Phe Gly Gln Met
                580                 585                 590

Ala Leu Gln Trp Ile Glu Arg Lys Val Asn Glu Tyr Leu Asn Glu Val
                595                 600                 605

Cys Gly Thr Glu Gly Glu Ala Phe Val Leu Tyr Gly Asp Thr Asp Ser
                610                 615                 620
```

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
            645                 650                 655

Glu Arg Met Glu Pro Ala Ile Asp Arg Gly Phe Arg Glu Met Cys Glu
        660                 665                 670

Tyr Met Asn Asn Lys Gln His Leu Met Phe Met Asp Arg Glu Ala Ile
            675                 680                 685

Ala Gly Pro Pro Leu Gly Ser Lys Gly Ile Gly Gly Phe Trp Thr Gly
    690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735

Thr Pro Lys Ala Val Gln Lys Ala Leu Lys Glu Cys Ile Arg Arg Met
        740                 745                 750

Leu Gln Glu Gly Glu Glu Ser Leu Gln Glu Tyr Phe Lys Glu Phe Glu
            755                 760                 765

Lys Glu Phe Arg Gln Leu Asn Tyr Ile Ser Ile Ala Ser Val Ser Ser
770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Gly Glu Lys Val Tyr Val
                820                 825                 830

Leu Pro Leu Arg Glu Gly Asn Pro Phe Gly Asp Lys Cys Ile Ala Trp
            835                 840                 845

Pro Ser Gly Thr Glu Ile Thr Asp Leu Ile Lys Asp Val Leu His
    850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Ala Ser
                885                 890                 895

Leu Phe Asp Met Phe Asp Phe
            900

<210> SEQ ID NO 12
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu

-continued

```
                65                  70                  75                  80
            Glu Ala Leu Gly Met Asp Asp Phe Lys Leu Ala Tyr Leu Ser Asp Thr
                            85                  90                  95
            Tyr Asn Tyr Glu Ile Lys Tyr Asp His Thr Lys Ile Arg Val Ala Asn
                           100                 105                 110
            Phe Asp Ile Glu Val Thr Ser Pro Asp Gly Phe Pro Glu Pro Ser Gln
                           115                 120                 125
            Ala Lys His Pro Ile Asp Ala Ile Thr His Tyr Asp Ser Ile Asp Asp
                           130                 135                 140
            Arg Phe Tyr Val Phe Asp Leu Leu Asn Ser Pro Tyr Gly Asn Val Glu
            145                 150                 155                 160
            Glu Trp Ser Ile Glu Ile Ala Ala Lys Leu Gln Glu Gln Gly Gly Asp
                           165                 170                 175
            Glu Val Pro Ser Glu Ile Ile Asp Lys Ile Ile Tyr Met Pro Phe Asp
                           180                 185                 190
            Asn Glu Lys Glu Leu Leu Met Glu Tyr Leu Asn Phe Trp Gln Gln Lys
                           195                 200                 205
            Thr Pro Val Ile Leu Thr Gly Trp Asn Val Glu Ser Phe Ala Ile Pro
            210                 215                 220
            Tyr Val Tyr Asn Arg Ile Lys Asn Ile Phe Gly Glu Ser Thr Ala Lys
            225                 230                 235                 240
            Arg Leu Ser Pro His Arg Lys Thr Arg Val Lys Val Ile Glu Asn Met
                           245                 250                 255
            Tyr Gly Ser Arg Glu Ile Ile Thr Leu Phe Gly Ile Ser Val Leu Asp
                           260                 265                 270
            Tyr Ile Asp Leu Tyr Lys Lys Phe Ser Phe Thr Asn Gln Pro Ser Tyr
                           275                 280                 285
            Ser Leu Asp Tyr Ile Ser Glu Phe Glu Leu Asn Val Gly Lys Leu Lys
                           290                 295                 300
            Tyr Asp Gly Pro Ile Ser Lys Leu Arg Glu Ser Asn His Gln Arg Tyr
            305                 310                 315                 320
            Ile Ser Tyr Asn Ile Ile Ala Val Tyr Arg Val Leu Gln Ile Asp Ala
                           325                 330                 335
            Lys Arg Gln Phe Ile Asn Leu Ser Leu Asp Met Gly Tyr Tyr Ala Lys
                           340                 345                 350
            Ile Gln Ile Gln Ser Val Phe Ser Pro Ile Lys Thr Trp Asp Ala Ile
                           355                 360                 365
            Ile Phe Asn Ser Leu Lys Glu Gln Asn Lys Val Ile Pro Gln Gly Arg
                           370                 375                 380
            Ser His Pro Val Gln Pro Tyr Pro Gly Ala Phe Val Lys Glu Pro Ile
            385                 390                 395                 400
            Pro Asn Arg Tyr Lys Tyr Val Met Ser Phe Asp Leu Thr Ser Leu Ala
                           405                 410                 415
            Pro Ser Ile Ile Arg Gln Val Asn Ile Ser Pro Glu Thr Ile Ala Gly
                           420                 425                 430
            Thr Phe Lys Val Ala Pro Leu His Asp Tyr Ile Asn Ala Val Ala Glu
                           435                 440                 445
            Arg Pro Ser Asp Val Tyr Ser Cys Ser Pro Asn Gly Met Met Tyr Tyr
                           450                 455                 460
            Lys Asp Arg Asp Gly Val Val Pro Thr Glu Ile Thr Lys Val Phe Asn
            465                 470                 475                 480
            Gln Arg Lys Glu His Lys Gly Tyr Met Leu Ala Ala Gln Arg Asn Gly
                           485                 490                 495
```

-continued

Glu Ile Ile Lys Glu Ala Leu His Asn Pro Asn Leu Ser Val Asp Glu
            500                 505                 510

Pro Leu Asp Val Asp Tyr Arg Phe Asp Phe Ser Asp Glu Ile Lys Glu
            515                 520                 525

Lys Ile Lys Lys Leu Ser Ala Lys Ser Leu Asn Glu Met Leu Phe Arg
            530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
            595                 600                 605

Cys Gly Thr Glu Gly Glu Ala Phe Val Leu Tyr Gly Asp Thr Asp Ser
            610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
            675                 680                 685

Ala Gly Pro Pro Leu Gly Ser Lys Gly Ile Gly Gly Phe Trp Thr Gly
            690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
            725                 730                 735

Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
            755                 760                 765

Lys Glu Phe Arg Gln Leu Asn Tyr Ile Ser Ile Ala Ser Val Ser Ser
            770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Glu Lys Val Tyr Val
            820                 825                 830

Leu Pro Leu Arg Glu Gly Asn Pro Phe Gly Asp Lys Cys Ile Ala Trp
            835                 840                 845

Pro Ser Gly Thr Glu Ile Thr Asp Leu Ile Lys Asp Asp Val Leu His
            850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
                900

<210> SEQ ID NO 13
<211> LENGTH: 903
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Ala Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                325                 330                 335

Lys Arg Gln Phe Ile Asn Leu Ser Leu Asp Met Gly Tyr Tyr Ala Lys
            340                 345                 350

Ile Gln Ile Gln Ser Val Phe Ser Pro Ile Lys Thr Trp Asp Ala Ile
        355                 360                 365
```

-continued

```
Ile Phe Asn Ser Leu Lys Glu Gln Asn Lys Val Ile Pro Gln Gly Arg
    370                 375                 380
Ser His Pro Val Gln Pro Tyr Pro Gly Ala Phe Val Lys Glu Pro Ile
385                 390                 395                 400
Pro Asn Arg Tyr Lys Tyr Val Met Ser Phe Asp Leu Thr Ser Leu Ala
                405                 410                 415
Pro Ser Ile Ile Arg Gln Val Asn Ile Ser Pro Glu Thr Ile Ala Gly
                420                 425                 430
Thr Phe Lys Val Ala Pro Leu His Asp Tyr Ile Asn Ala Val Ala Glu
            435                 440                 445
Arg Pro Ser Asp Val Tyr Ser Cys Ser Pro Asn Gly Met Met Tyr Tyr
    450                 455                 460
Lys Asp Arg Asp Gly Val Val Pro Thr Glu Ile Thr Lys Val Phe Asn
465                 470                 475                 480
Gln Arg Lys Glu His Lys Gly Tyr Met Leu Ala Ala Gln Arg Asn Gly
                485                 490                 495
Glu Ile Ile Lys Glu Ala Leu His Asn Pro Asn Leu Ser Val Asp Glu
                500                 505                 510
Pro Leu Asp Val Asp Tyr Arg Phe Asp Phe Ser Asp Glu Ile Lys Glu
            515                 520                 525
Lys Ile Lys Lys Leu Ser Ala Lys Ser Leu Asn Glu Met Leu Phe Arg
    530                 535                 540
Ala Gln Arg Thr Glu Val Ala Gly Met Thr Ala Gln Ile Leu Arg Lys
545                 550                 555                 560
Leu Leu Ile Asn Ser Leu Tyr Gly Ala Leu Gly Asn Val Trp Phe Arg
                565                 570                 575
Tyr Tyr Asp Leu Arg Asn Ala Thr Ala Ile Thr Thr Phe Gly Gln Met
                580                 585                 590
Ala Leu Gln Trp Ile Glu Arg Lys Val Asn Glu Tyr Leu Asn Glu Val
            595                 600                 605
Cys Gly Thr Glu Gly Glu Ala Phe Val Leu Tyr Gly Asp Thr Asp Ser
    610                 615                 620
Ile Tyr Val Ser Ala Asp Lys Ile Ile Asp Lys Val Gly Glu Ser Lys
625                 630                 635                 640
Phe Arg Asp Thr Asn His Trp Val Asp Phe Leu Asp Lys Phe Ala Arg
                645                 650                 655
Glu Arg Met Glu Pro Ala Ile Asp Arg Gly Phe Arg Glu Met Cys Glu
                660                 665                 670
Tyr Met Asn Asn Lys Gln His Leu Met Phe Met Asp Arg Glu Ala Ile
            675                 680                 685
Ala Gly Pro Pro Leu Gly Ser Lys Gly Ile Gly Gly Phe Trp Thr Gly
    690                 695                 700
Lys Lys Arg Tyr Ala Leu Asn Val Trp Asp Met Glu Gly Thr Arg Tyr
705                 710                 715                 720
Ala Glu Pro Lys Leu Lys Ile Met Gly Leu Glu Thr Gln Lys Ser Ser
                725                 730                 735
Thr Pro Lys Ala Val Gln Lys Ala Leu Lys Glu Cys Ile Arg Arg Met
                740                 745                 750
Leu Gln Glu Gly Glu Glu Ser Leu Gln Glu Tyr Phe Lys Glu Phe Glu
            755                 760                 765
Lys Glu Phe Arg Gln Leu Asn Tyr Ile Ser Ile Ala Ser Val Ser Ser
    770                 775                 780
```

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
            805                 810                 815

Gly Asn Ile Asp Ala Pro Gln Val Val Glu Gly Glu Lys Val Tyr Val
        820                 825                 830

Leu Pro Leu Arg Glu Gly Asn Pro Phe Gly Asp Lys Cys Ile Ala Trp
    835                 840                 845

Pro Ser Gly Thr Glu Ile Thr Asp Leu Ile Lys Asp Asp Val Leu His
850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
            885                 890                 895

Leu Phe Asp Met Phe Asp Phe
            900

<210> SEQ ID NO 14
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
            85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
            165                 170                 175

Glu Val Pro Ser Glu Ile Ile Asp Lys Ile Ile Tyr Met Pro Phe Asp
        180                 185                 190

Asn Glu Lys Glu Leu Leu Met Glu Tyr Leu Asn Phe Trp Gln Gln Lys
    195                 200                 205

Thr Pro Val Ile Leu Thr Gly Trp Asn Val Glu Ser Phe Ala Ile Pro
210                 215                 220

Tyr Val Tyr Asn Arg Ile Lys Asn Ile Phe Gly Glu Ser Thr Ala Lys
225                 230                 235                 240

```
Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                325                 330                 335

Lys Arg Gln Phe Ile Asn Leu Ser Leu Asp Met Gly Tyr Tyr Ala Lys
                340                 345                 350

Ile Gln Ile Gln Ser Val Phe Ser Pro Ile Lys Thr Trp Asp Ala Ile
            355                 360                 365

Ile Phe Asn Ser Leu Lys Glu Gln Asn Lys Val Ile Pro Gln Gly Arg
        370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Ser Ala
                405                 410                 415

Val Ser Ile Ile Arg Gln Val Asn Ile Ser Pro Glu Thr Ile Ala Gly
                420                 425                 430

Thr Phe Lys Val Ala Pro Leu His Asp Tyr Ile Asn Ala Val Ala Glu
            435                 440                 445

Arg Pro Ser Asp Val Tyr Ser Cys Ser Pro Asn Gly Met Met Tyr Tyr
        450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
            500                 505                 510

Pro Leu Asp Val Asp Tyr Arg Phe Asp Phe Ser Asp Glu Ile Lys Glu
        515                 520                 525

Lys Ile Lys Lys Leu Ser Ala Lys Ser Leu Asn Glu Met Leu Phe Arg
    530                 535                 540

Ala Gln Arg Thr Glu Val Ala Gly Met Thr Ala Gln Ile Leu Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
        595                 600                 605

Cys Gly Thr Glu Gly Glu Ala Phe Val Leu Tyr Gly Asp Thr Asp Ser
    610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655
```

-continued

```
Glu Arg Met Glu Pro Ala Ile Asp Arg Gly Phe Arg Glu Met Cys Glu
            660                 665                 670
Tyr Met Asn Asn Lys Gln His Leu Met Phe Met Asp Arg Glu Ala Ile
        675                 680                 685
Ala Gly Pro Pro Leu Gly Ser Lys Gly Ile Gly Gly Phe Trp Thr Gly
    690                 695                 700
Lys Lys Arg Tyr Ala Leu Asn Val Trp Asp Met Glu Gly Thr Arg Tyr
705                 710                 715                 720
Ala Glu Pro Lys Leu Lys Ile Met Gly Leu Glu Thr Gln Lys Ser Ser
                725                 730                 735
Thr Pro Lys Ala Val Gln Lys Ala Leu Lys Glu Cys Ile Arg Arg Met
                740                 745                 750
Leu Gln Glu Gly Glu Glu Ser Leu Gln Glu Tyr Phe Lys Glu Phe Glu
            755                 760                 765
Lys Glu Phe Arg Gln Leu Asn Tyr Ile Ser Ile Ala Ser Val Ser Ser
    770                 775                 780
Ala Asn Asn Ile Ala Lys Tyr Asp Val Gly Gly Phe Pro Gly Pro Lys
785                 790                 795                 800
Cys Pro Phe His Ile Arg Gly Ile Leu Thr Tyr Asn Arg Ala Ile Lys
                805                 810                 815
Gly Asn Ile Asp Ala Pro Gln Val Val Glu Gly Glu Lys Val Tyr Val
            820                 825                 830
Leu Pro Leu Arg Glu Gly Asn Pro Phe Gly Asp Lys Cys Ile Ala Trp
        835                 840                 845
Pro Ser Gly Thr Glu Ile Thr Asp Leu Ile Lys Asp Asp Val Leu His
850                 855                 860
Trp Met Asp Tyr Thr Val Leu Leu Glu Lys Thr Phe Ile Lys Pro Leu
865                 870                 875                 880
Glu Gly Phe Thr Ser Ala Ala Lys Leu Asp Tyr Glu Lys Lys Ala Ser
                885                 890                 895
Leu Phe Asp Met Phe Asp Phe
                900
```